US011141166B2

(12) United States Patent
Itoh et al.

(10) Patent No.: US 11,141,166 B2
(45) Date of Patent: Oct. 12, 2021

(54) CLIP TREATMENT TOOL

(71) Applicant: FUJIFILM Corporation, Tokyo (JP)

(72) Inventors: Koji Itoh, Kanagawa (JP); Issei Suzuki, Kanagawa (JP); Toshihiko Izaki, Kanagawa (JP); Syuji Tsuchiya, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 174 days.

(21) Appl. No.: 16/574,106

(22) Filed: Sep. 18, 2019

(65) Prior Publication Data

US 2020/0008811 A1    Jan. 9, 2020

Related U.S. Application Data

(63) Continuation of application No. PCT/JP2018/002345, filed on Jan. 25, 2018.

(30) Foreign Application Priority Data

Mar. 22, 2017 (JP) .............................. JP2017-055405
Jun. 21, 2017 (JP) .............................. JP2017-121206

(51) Int. Cl.
*A61B 17/128* (2006.01)
*A61B 17/122* (2006.01)
(Continued)

(52) U.S. Cl.
CPC ...... *A61B 17/1285* (2013.01); *A61B 17/1227* (2013.01); *A61B 2017/0034* (2013.01);
(Continued)

(58) Field of Classification Search
CPC . A61B 17/122; A61B 17/128; A61B 17/1285; A61B 2017/00818; A61B 2017/12004
See application file for complete search history.

(56) References Cited

U.S. PATENT DOCUMENTS 3,958,576 A * 5/1976 Komiya ............... A61B 17/083
                                                    606/142
5,156,609 A * 10/1992 Nakao ................ A61B 17/0682
                                                    227/179.1
(Continued)

FOREIGN PATENT DOCUMENTS

EP       2327364       6/2011
JP       2004073634    3/2004
(Continued)

OTHER PUBLICATIONS

"International Search Report (Form PCT/ISA/210) of PCT/JP2018/002345", dated Apr. 3, 2018, with English translation thereof, pp. 1-4.

(Continued)

*Primary Examiner* — Ryan J. Severson
(74) *Attorney, Agent, or Firm* — JCIPRNET

(57) ABSTRACT

In a clip treatment tool, a clip locking part brings arms into a closed state after the arms are brought into a closed state in a state where distal ends of the arms of the clip brought into an open state is pressed against a treatment part and the treatment part is ligated to the distal ends of the arms brought into the closed state. After the clip in which the arms are locked to the closed state is separated from the sheath part and indwelled in the treatment part, the clip removal part is indwelled in the treatment part, the locking of the arms locked to the closed state is released, the arms are brought into the open state as the locking is released, and the clip removed from the treatment part is maintained and taken out.

19 Claims, 31 Drawing Sheets

(51) Int. Cl.
*A61B 17/00* (2006.01)
*A61B 17/12* (2006.01)

(52) U.S. Cl.
CPC ............... *A61B 2017/00818* (2013.01); *A61B 2017/12004* (2013.01)

(56) References Cited

U.S. PATENT DOCUMENTS

| | | | | |
|---|---|---|---|---|
| 5,766,189 A * | 6/1998 | Matsuno | .............. | A61B 17/122 606/139 |
| 6,391,035 B1 * | 5/2002 | Appleby | .............. | A61B 17/128 606/142 |
| 6,814,742 B2 * | 11/2004 | Kimura | .............. | A61B 17/1285 606/151 |
| 7,041,118 B2 * | 5/2006 | Muramatsu | ........ | A61B 17/1227 606/207 |
| 7,131,977 B2 * | 11/2006 | Fowler | ............... | A61B 17/1285 606/138 |
| 7,452,327 B2 | 11/2008 | Durgin et al. | | |
| 8,083,668 B2 | 12/2011 | Durgin et al. | | |
| 8,551,119 B2 * | 10/2013 | Kogiso | ................ | A61B 17/122 606/142 |
| 8,974,371 B2 | 3/2015 | Durgin et al. | | |
| 9,339,270 B2 | 5/2016 | Martinez et al. | | |
| 9,370,371 B2 | 6/2016 | Durgin et al. | | |
| 9,795,390 B2 * | 10/2017 | Jin | ..................... | A61B 17/1285 |
| 9,949,740 B2 | 4/2018 | Satake et al. | | |
| 9,980,725 B2 | 5/2018 | Durgin et al. | | |
| 10,820,904 B2 * | 11/2020 | Ryan | .................. | A61B 17/1285 |
| 10,842,351 B2 * | 11/2020 | Osaka | ............... | A61B 1/00087 |
| 10,842,500 B2 * | 11/2020 | Satake | ................ | A61B 17/122 |
| 10,905,434 B2 * | 2/2021 | Estevez | ............. | A61B 17/1222 |
| 2004/0044363 A1 * | 3/2004 | Fowler | .............. | A61B 17/1285 606/205 |
| 2004/0176784 A1 * | 9/2004 | Okada | ................ | A61B 17/1285 606/142 |
| 2005/0107809 A1 * | 5/2005 | Litscher | ............. | A61B 17/1285 606/142 |
| 2007/0021777 A1 * | 1/2007 | Fowler | ................... | A61B 17/29 606/205 |
| 2008/0140089 A1 | 6/2008 | Kogiso et al. | | |
| 2008/0255427 A1 * | 10/2008 | Satake | ................ | A61B 17/083 600/204 |
| 2009/0326558 A1 | 12/2009 | Cui et al. | | |
| 2011/0054498 A1 * | 3/2011 | Monassevitch | .... | A61B 17/1285 606/142 |
| 2011/0245855 A1 * | 10/2011 | Matsuoka | .......... | A61B 17/1285 606/157 |
| 2015/0230799 A1 | 8/2015 | Satake et al. | | |
| 2016/0346074 A1 * | 12/2016 | Tafti | ......................... | A61F 2/01 |
| 2016/0367258 A1 | 12/2016 | Jin et al. | | |
| 2018/0193022 A1 | 7/2018 | Satake et al. | | |
| 2018/0235608 A1 | 8/2018 | Durgin et al. | | |
| 2020/0008811 A1 * | 1/2020 | Itoh | .................... | A61B 17/1227 |

FOREIGN PATENT DOCUMENTS

| | | |
|---|---|---|
| JP | 2007125264 A * | 5/2007 |
| JP | 2007244826 | 9/2007 |
| JP | 4921173 | 4/2012 |
| JP | 5750619 | 7/2015 |
| WO | 2006068242 | 6/2006 |
| WO | 2012126477 | 9/2012 |
| WO | 2014181675 | 11/2014 |

OTHER PUBLICATIONS

"Written Opinion of the International Searching Authority (Form PCT/ISA/237) of PCT/JP2018/002345", dated Apr. 3, 2018, with English translation thereof, pp. 1-9.

Office Action of Japan Counterpart Application, with English translation thereof, dated Jun. 9, 2020, pp. 1-5.

"Search Report of Europe Counterpart Application", dated Feb. 20, 2020, p. 1-p. 9.

* cited by examiner

FIG. 19
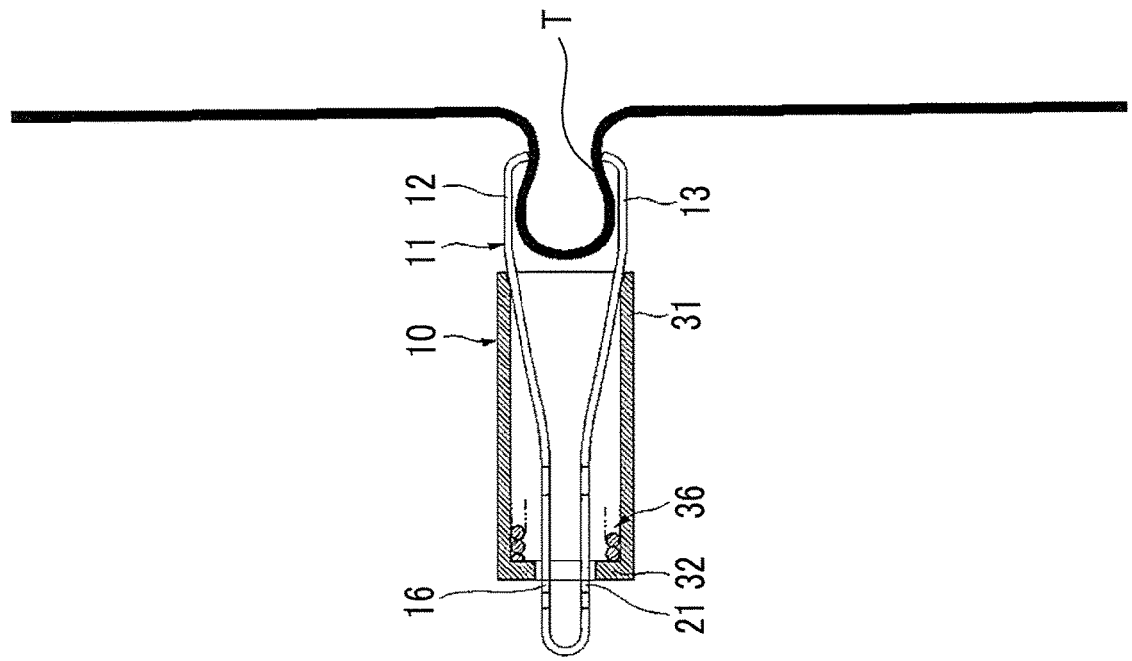
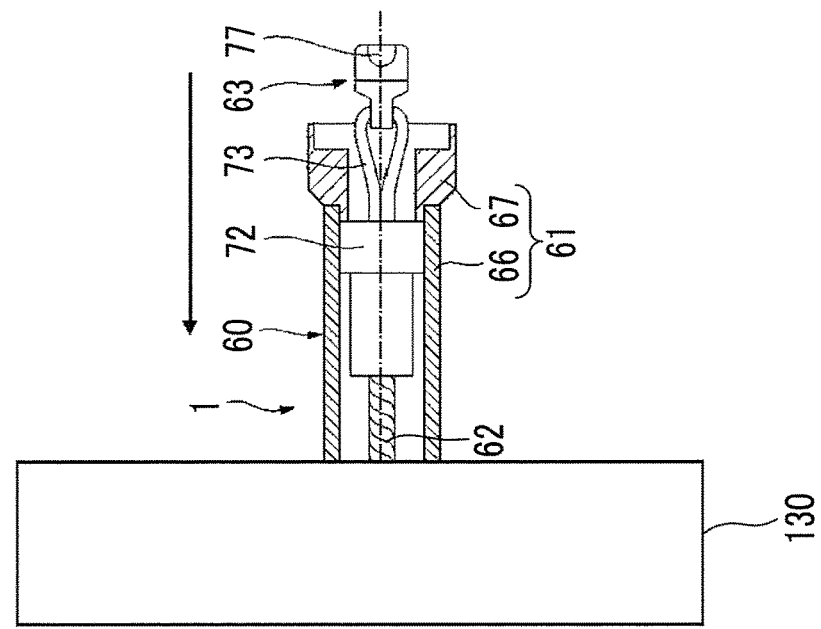

FIG. 21
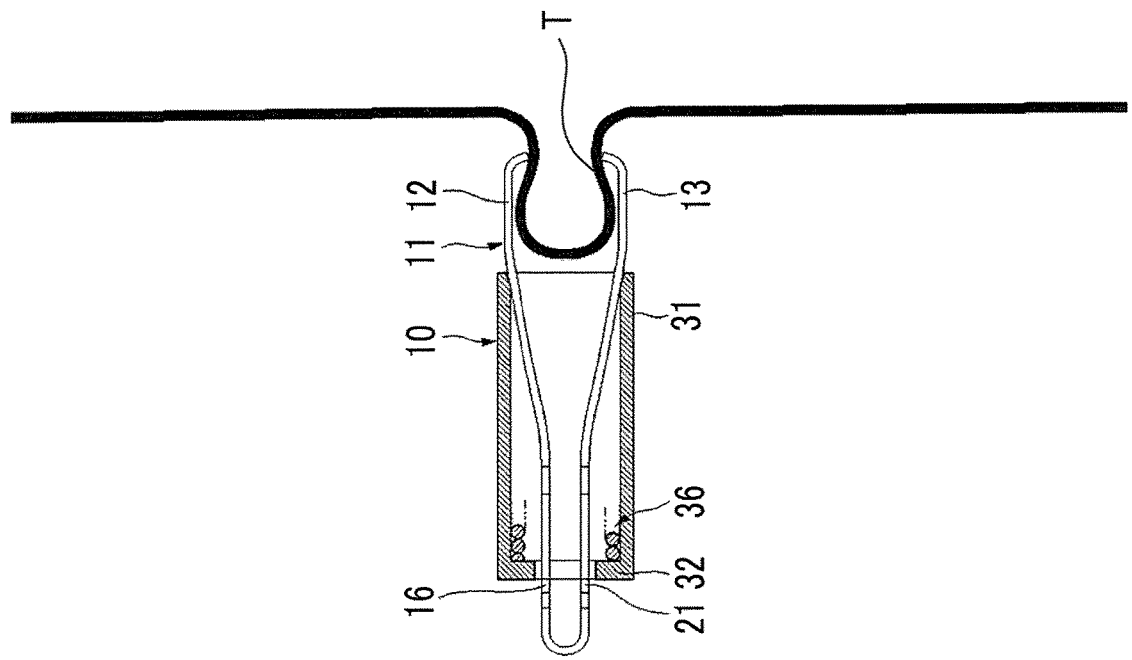
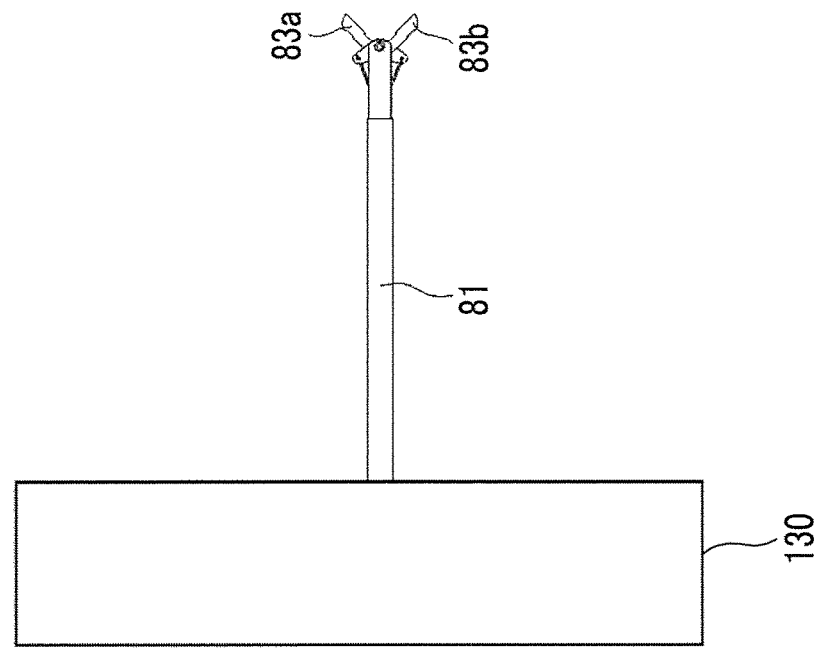

CLIP TREATMENT TOOL

CROSS-REFERENCE TO RELATED APPLICATIONS

This application is a Continuation of PCT International Application No. PCT/JP2018/002345 filed on Jan. 25, 2018, which claims priority under 35 U.S.C § 119(a) to Japanese Patent Applications No. 2017-055405 filed on Mar. 22, 2017 and No. 2017-121206 filed on Jun. 21, 2017. Each of the above application(s) is hereby expressly incorporated by reference, in its entirety, into the present application.

BACKGROUND OF THE INVENTION

1. Field of the Invention

The present invention relates to a lip treatment tool for an endoscope to be used for occlusion, hemostasis, and the like of a wound in a living body.

2. Description of the Related Art

Clip treatment tools for endoscopes are used to perform occlusion, hemostasis, and the like of wounds by protruding arms of a clip from a distal end of an endoscope inserted into a living body, and ligating treatment parts, such as a wound and a bleeding spot, at distal ends of the arms of the clip.

As such clip treatment tools, as in JP5750619B, JP4921173B, U.S. Pat. No. 9,339,270B, and US2016/0367258A, clip treatment tools capable of freely opening and closing arms of a clip are well-known. By utilizing techniques of JP5750619B, JP4921173B, U.S. Pat. No. 9,339,270B, and US2016/0367258A, for example, the arms of the clip can be freely opened and closed within a patient's body to re-grab a treatment part. Therefore, it is possible to perform treatment, such as hemostasis, by applying the clip at an exact position of the treatment part.

SUMMARY OF THE INVENTION

However, the clip is indwelled in the patient's body once the clip is ligated to the treatment part. For that reason, in a case where the position of the ligation by the clip is shifted from a position to be ligated and indwelled due to an operation error or the like, in a case where the indwelled clip becomes unnecessary after hemostasis or the like is sufficiently completed enough, or the like, there is a problem in that the clip is left behind in the living body, patient's body tissue changes, and the patient has to wait for the clip to come off naturally, that is, the clip cannot be removed at any timing.

An object of the invention is to provide a clip treatment tool capable of reliably maintaining its state once a clip has been applied and removing the clip indwelled in a living body at any timing.

In order to achieve the above object, a clip treatment tool comprises an operating part; a clip; a sheath part; and a clip removal part. The clip is attachably and detachably disposed at a distal end of the sheath part and the operating part is attached to a proximal end of the sheath part. The clip includes a clip body having two or more arms that are opened and closed, and a clip locking part that locks the two or more arms to a closed state after the two or more arms of the clip body are brought into an open state by an operation of the operating part, the two or more arms are brought into the closed state in a state where distal ends of the two or more arms brought into the open state are pressed against a treatment part, and the treatment part is ligated by the distal ends of the two or more arms brought into the closed state. The clip removal part releases the locking to the closed state of the two or more arms of the clip indwelled in the treatment part after the clip of which the two or more arms are locked to the closed state by the clip locking part are separated from the sheath part and indwelled in the treatment part by the operation of the operating part, to bring the two or more arms into the open state as the locking is released, and holds and removes the clip removed from the treatment part.

Here, it is preferable that the clip further includes a tubular retaining pipe that houses a proximal end of the clip body, the two or more arms are protruded from a distal end of the retaining pipe to be in the open state, and the two or more arms protruded from the distal end of the retaining pipe are housed within the retaining pipe to be in the closed state by the operation of the operating part, the clip locking part has protruding parts provided in the two or more arms, and an opening part provided in a proximal end of the retaining pipe, and in a case where the clip body is relatively moved to a proximal side of the retaining pipe, and an external diameter of the protruding parts that is a diameter of a circumscribed circle circumscribed on distal ends of the protruding parts of the two or more arms becomes smaller than an internal diameter of the opening part that is a diameter of an inscribed circle inscribed on an opening of the opening part, so that the protruding parts exceeds the opening part, the external diameter of the protruding parts becomes larger than the internal diameter of the opening part, and the protruding parts and the opening part are engaged with each other, so that the two or more arms are locked to the closed state.

Additionally, it is preferable that the clip further includes a spring member that biases the clip body housed within the retaining pipe to a distal side of the retaining pipe, the spring member is compressed as the clip body is relatively moved to the proximal side of the retaining pipe, and the two or more arms is locked to the closed state in a state where the clip body is biased to the distal side of the retaining pipe by the spring member, and the spring member is extended to relatively move the clip body to the distal side of the retaining pipe in a case where the locking is released, and the two or more arms are protruded from the distal end of the retaining pipe to be in the open state.

Additionally, it is preferable that the clip removal part reduces the external diameter of the protruding parts to be equal to or less than the internal diameter of the opening part and releases the locking by releasing the engagement between the protruding parts and the opening part, and the spring member is extended to relatively move the clip body to the distal side of the retaining pipe in a case where the locking is released and the two or more arms are protruded from the distal end of the retaining pipe to be in the open state.

Additionally, it is preferable that the clip removal part has a snare-like member including a loop that is enlarged or reduced in diameter by the operation of the operating part, and reduces the external diameter of the protruding parts to be equal to or less than the internal diameter of the opening part by surrounding and clamping the protruding parts by the loop.

Additionally, it is preferable that the clip removal part has gripping forceps including a gripping part that is opened and closed by the operation of the operating part, and reduces the external diameter of the protruding parts to be equal to or less than the internal diameter of the opening part by sandwiching and pressing the protruding parts by the gripping part.

Additionally, it is preferable that wherein the clip further includes a movement regulating part that restricting the clip body from jumping out of the distal end of the retaining pipe in a case where the clip removal part releases the locking and the spring member is extended to relatively move the clip body to the distal side of the retaining pipe.

Additionally, it is preferable that the clip body has a connecting part that connects proximal ends of the two or more arms to each other, the movement regulating part has a pin-shaped member, and the pin-shaped member has both ends fixed to an inner peripheral surface of the retaining pipe and is inserted between the two or more arms, to extend in a direction orthogonal to an opening/closing direction of the two or more arms, and in a case where the locking is released and the clip body has relatively moved to the distal side of the retaining pipe, the pin-shaped member and the connecting part abut against each other to restrict the clip body from jumping out of the distal end of the retaining pipe.

Additionally, it is preferable that the clip body has a connecting part that connects proximal ends of the two or more arms to each other, the movement regulating part has one or more cantilever beam members, and the one or more cantilever beam members have one end fixed to the distal end of the retaining pipe, and is inserted between the two or more arms to extend in a direction orthogonal to an opening/closing direction of the two or more arms from the distal end of the retaining pipe, and, in a case where the locking is released and the clip body has relatively moved to the distal side of the retaining pipe, the cantilever beam member and the connecting part abut against each other to restrict the clip body from jumping out of the distal end of the retaining pipe.

Additionally, it is preferable that the clip body has a connecting part that connects proximal ends of the two or more arms to each other, the movement regulating part has a pin-shaped member, and the pin-shaped member has both ends fixed to the distal end of the retaining pipe, and is inserted between the two or more arms, to extend in a direction orthogonal to an opening/closing direction of the two or more arms, and in a case where the locking is released and the clip body has relatively moved to the distal side of the retaining pipe, the pin-shaped member and the connecting part abut against each other to restrict the clip body from jumping out of the distal end of the retaining pipe.

Additionally, it is preferable that the clip body has a connecting part that connects proximal ends of the two or more arms to each other, the movement regulating part has two or more protrusions that are provided on an inner peripheral surface of the retaining pipe, are inserted between the two or more arms, and protrude in a direction orthogonal to an opening/closing direction of the two or more arms from the inner peripheral surface of the retaining pipe, and in a case where the locking is released and the clip body has been relatively moved to the distal side of the retaining pipe, the two or more protrusions and the connecting part abut against each other to restrict the clip body from jumping out of the distal end of the retaining pipe.

Additionally, it is preferable that the movement regulating part has a second protrusion that protrudes from each of the two or more arms toward a wall face of the retaining pipe and two or more slits that are formed in the wall face of the retaining pipe in correspondence with the second protrusion of each of the two or more arms and are engaged with the second protrusion of each of the two or more arms, and in a case where the locking is released and the clip body has relatively moved to the distal side of the retaining pipe, the second protrusion of each of the two or more arms abuts against a distal end of each of the two or more slits of the retaining pipe to restrict the clip body from jumping out of the distal end of the retaining pipe.

Additionally, it is preferable that the clip treatment tool further comprises pressed parts that are provided on both sides of the protruding parts in a pressing direction in which the protruding parts are pressed, in an outer end surface of the proximal end of the retaining pipe, and are moved toward the protruding parts by being pressed from the both sides in the pressing direction, and the clip removal part moves the pressed parts toward the protruding parts by pressing the pressed parts from the both sides in the pressing direction, reduces the external diameter of the protruding parts to be equal to or less than the internal diameter of the opening part by pressing the protruding parts, and releases the locking by releasing the engagement between the protruding parts and the opening part.

Additionally, it is preferable that the retaining pipe has two or more second opening parts that respectively expose portions of the two or more arms in a case where the arm is locked to the closed state, at proximal-side positions of side surfaces that respectively face the two or more arms, and the clip removal part presses the two or more arms exposed from the two or more second opening parts of the side surfaces of the retaining pipe to reduce the external diameter of the protruding parts to be equal to or less than the internal diameter of the opening part, and releases the locking by releasing the engagement between the protruding parts and the opening part.

Additionally, it is preferable that each of the two or more arms has a third protrusion that protrudes from a central axis of the retaining pipe toward each of the two or more second opening parts in a case where the two or more arms are locked to the closed state.

Additionally, it is preferable that the clip treatment tool further comprises an operating wire that is inserted so as to be movable forward and backward within the sheath part by the operation of the operating part; and a coupling member that couples the clip body and the operating wire to each other, the clip further includes a tubular retaining pipe and a biasing member, the clip body has two arms, and the two arms face each other, and extend so as to be separated from each other from the proximal side toward the distal side, as the clip body moves to the distal side or the proximal side, the retaining pipe functions to open and close the two arms, and houses the clip body therein by the movement of the clip body from the distal side to the proximal side, the clip locking part has a locking part provided on proximal sides of the two arms, and a locked part provided on the proximal side of the retaining pipe, the coupling member is housed inside the retaining pipe, and is attachably and detachably engaged with the two arms, and couples the clip body and the operating wire to each other by connecting a distal end of the operating wire to a proximal end thereof, the biasing member is housed inside the retaining pipe, and biases the clip body from the proximal side to the distal side with respect to the retaining pipe, and as the operating wire moves from the distal side to the proximal side by the operation of the operating part, the coupling member moves from the distal side to the proximal side, the clip body moves from the distal side to the proximal side, the locking part is locked to the locked part, and the clip body is locked to the retaining pipe.

Additionally, it is preferable that as the coupling member moves from the distal side to the proximal side, the two arms are pressed by the distal end of the retaining pipe in a direction in which the two arms approach each other, and the two arms are gradually closed from the open state and brought into the closed state.

Additionally, it is preferable that the locking part has two plate-shaped members which each include an inclined part provided at an end, on the proximal side, of each of the two arms and a top part provided on the distal side from the inclined part and having an end on the distal side serving as a corner, and in which the end of the top part on the distal side serve as the corner, and the top parts of the two plate-shaped members are formed so as to face each other in an opening/closing direction of the two arms, the locked part has a locking part that is formed as an end of the retaining pipe on the proximal side is reduced in diameter and has an internal diameter smaller than a length between the two top parts that face each other, and as the coupling member moves from the distal side to the proximal side, the two inclined parts are pressed by a distal end of the locking hole in a direction in which the inclined parts approach each other and pass through the locking hole, the corners of the two top parts move to positions exceeding the locking hole of the locked part, the corners of the two top parts are locked to a proximal end surface of the locked part by separating the two inclined parts from each other by an elastic force, and the coupling member is locked to the retaining pipe in a state where the two arms are in the closed state.

Additionally, it is preferable that an external diameter of the coupling member is smaller than an internal diameter of the locking hole, and as the operating wire moves from the distal side to the proximal side in a state where the coupling member is locked to the retaining pipe, the engagement between the two arms and the coupling member is released, the coupling member passes through the locking hole, a distal end of the coupling member moves to a position exceeding a proximal end of the locking part, and the clip body and the coupling member are separated from each other.

Additionally, it is preferable that in a case where the two top parts are pressed from both outsides and an external diameter in the corners of the two top parts on the distal side becomes smaller than the internal diameter of the locking hole in a state where the clip body and the coupling member are separated from each other, the clip body is biased by the biasing member, to be moved from the proximal side to the distal side, and the two arms are gradually opened from the closed state and returns to the open state as the clip body moves from the proximal side to the distal side.

Additionally, it is preferable that each of the two plate-shaped members is formed such that a portion, in a width direction, of a proximal end of each of the two arms is bent in the direction orthogonal to the opening/closing direction of the two arms, each of the two top parts has a recess that is recessed in the opening/closing direction of the two arms, and the recess of each of the two top parts is pressed from both outsides in the opening/closing direction of the two arms.

Additionally, it is preferable that each of the two arms has a projection part that protrudes in a width direction, the retaining pipe has a narrowed part having an internal diameter narrower than an internal diameter at both ends, at a central part thereof in an axial direction, and the biasing member is disposed between the projection part and the narrowed part, and the locking part is movable nearer to the proximal side than the narrowed part.

Additionally, it is preferable that the clip treatment tool comprises a first treatment tool that has at least a first operating part serving as the operating part, and the sheath part; and a second treatment tool that has at least a second operating part serving as the operating part, and the clip removal part, and the first treatment tool and the second treatment tool are separately configured.

In the invention, the treatment part can be re-grabbed by the clip until the clip is ligated to the treatment part, and a state where the arms of the clip are locked to the closed state and the clip is ligated to the treatment part can be reliably maintained, once the clip is ligated to the treatment part. Additionally, after the clip is indwelled in the treatment part within the living body, the locking of the arms of the indwelled clip can be released at any timing, and the clip can be removed.

BRIEF DESCRIPTION OF THE DRAWINGS

FIG. 19 is a conceptual diagram view illustrating a state where the clip is separated from the treatment tool body and is indwelled in the treatment part.

FIG. 21 is a conceptual diagram view illustrating a state where a distal end of an insertion part of the second treatment tool is protruded from the treatment tool delivery port of the endoscope.

DESCRIPTION OF THE PREFERRED EMBODIMENTS

Hereinafter, a clip treatment tool related to the invention will be described in detail on the basis of preferable embodiments illustrated in the attached drawings.

In addition, in all the drawings, in order to facilitate understanding, dimensions, such as the thickness and length of respective components in the present embodiments, are appropriately changed from actual dimensions as needed.

Figure 1:
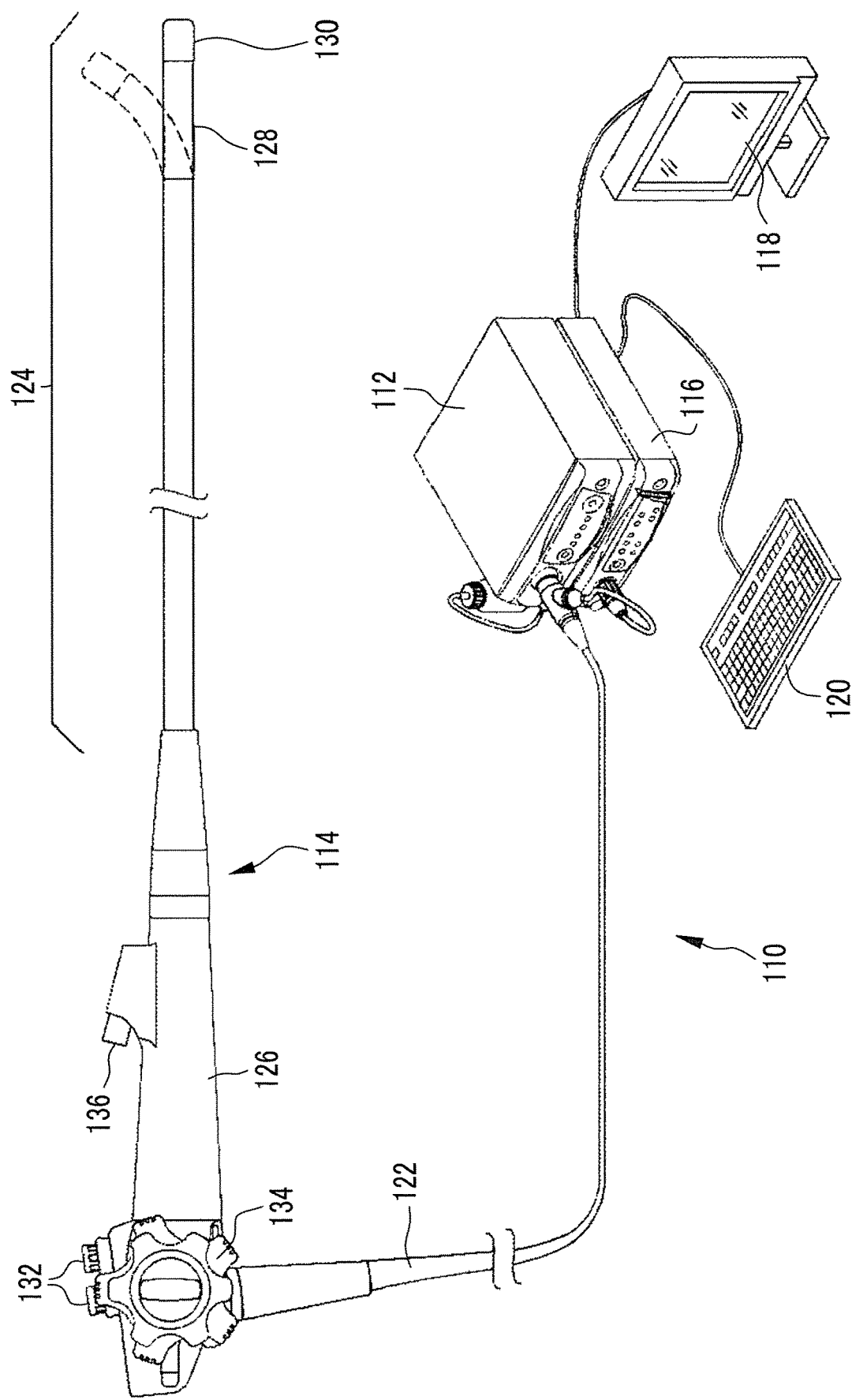
FIG. 1 is an external view illustrating the configuration of an embodiment of an endoscope system used for treatment by a clip treatment tool related to the invention.

FIG. 1 is an external view illustrating the configuration of an embodiment of the endoscope system used for carrying out treatment by a clip treatment tool related to the invention. An endoscope system 110 illustrated in FIG. 1 comprises a light source device 112, an endoscope 114, a processor device 116, a monitor (display device) 118, and a console (input device) 120.

The endoscope 114 is optically connected to the light source device 112 via a universal cord 122 and is electrically connected to the processor device 116. Additionally, the monitor 118 and the console 120 are connected to the processor device 116.

The endoscope 114 captures images an endoscope image of a patient's (subject) region to be observed, using light emitted from the light source device 112, and comprises an insertion part 124 to be inserted into a patient's body, and an operating part 126 that is provided at a proximal end of the insertion part 124 to perform a bending operation of the insertion part, an operation for observation, and the like. Additionally, the insertion part 124 comprises a bending part 128 and a distal end 130 that are provided on a distal side of the insertion part 124.

The operating part 126 is provided with a button 132 that operates imaging operation, an angle knob 134 that operates the bending operation of the bending part 128, and the like. Additionally, the operating part 126 is provided with a treatment tool insertion port 136 into which treatment tools, such as a clip treatment tool to be described below, are inserted.

The bending part 128 performs the bending operation by a rotational movement operation of the angle knob 134 provided in the operating part 126. The bending part 128 is bent in optional directions and at optional angles, and the distal end 130 is oriented in a desired direction by this bending operation.

Figure 2:
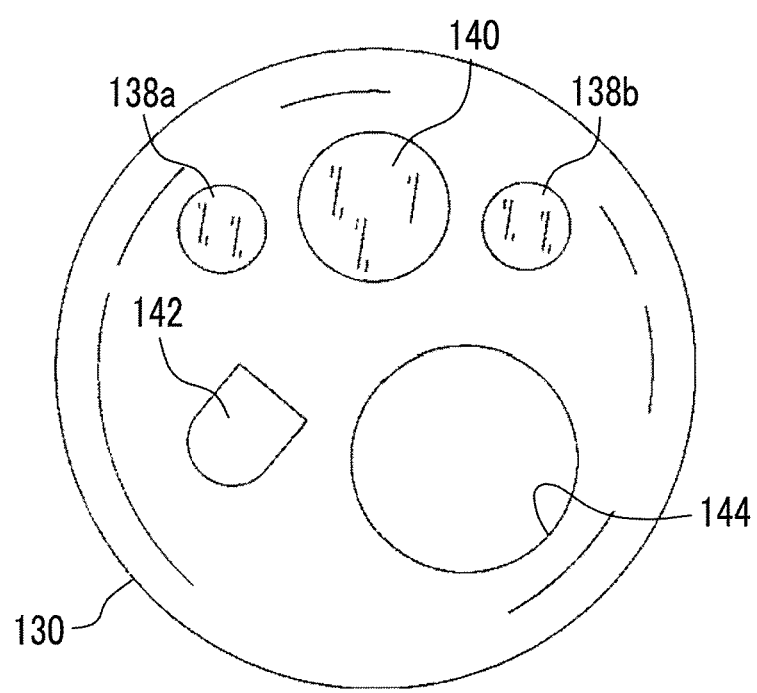
FIG. 2 is a front view of a distal end surface of a distal end of an insertion part of an endoscope illustrated in FIG. 1.

Units for illumination and image formation, an imaging element that images the patient's region to be observed, and the like are provided inside the distal end 130. Additionally, as illustrated in FIG. 2, illumination windows 138a and 138b for irradiating the region to be observed with illumination light, an observation window 140 for imaging the region to be observed, an air/water supply port 142 used as an outlet of an air/water supply channel, a treatment tool delivery port 144 serving as an outlet of a treatment tool, and the like are disposed on a distal end surface of the distal end 130.

The processor device 116 image-processes image signals of the endoscope image captured by the endoscope 114, and controls the operation of the light source device 112, the imaging element, and the like on the basis of instructions or the like input from the button 132 and the console 120 that are provided in the operating part 126 of the endoscope 114.

The light guided from the light source device 112 is radiated from the distal end 130 of the insertion part 124 of the endoscope 114 toward the patient's region to be observed. The appearance of the region to be observed, which is irradiated with the illumination light, is photoelectrically converted and imaged by the imaging element via a lens unit. The image signals of the endoscope image of the patient's region to be observed that has been imaged are image-processed by the processor device 116, and the endoscope image after the image processing is displayed on the monitor 118.

Next, the clip treatment tool of the invention will be described.

The clip treatment tool of the present embodiment comprises a first treatment tool and a second treatment tool. First, the first treatment tool will be described.

Figure 3:
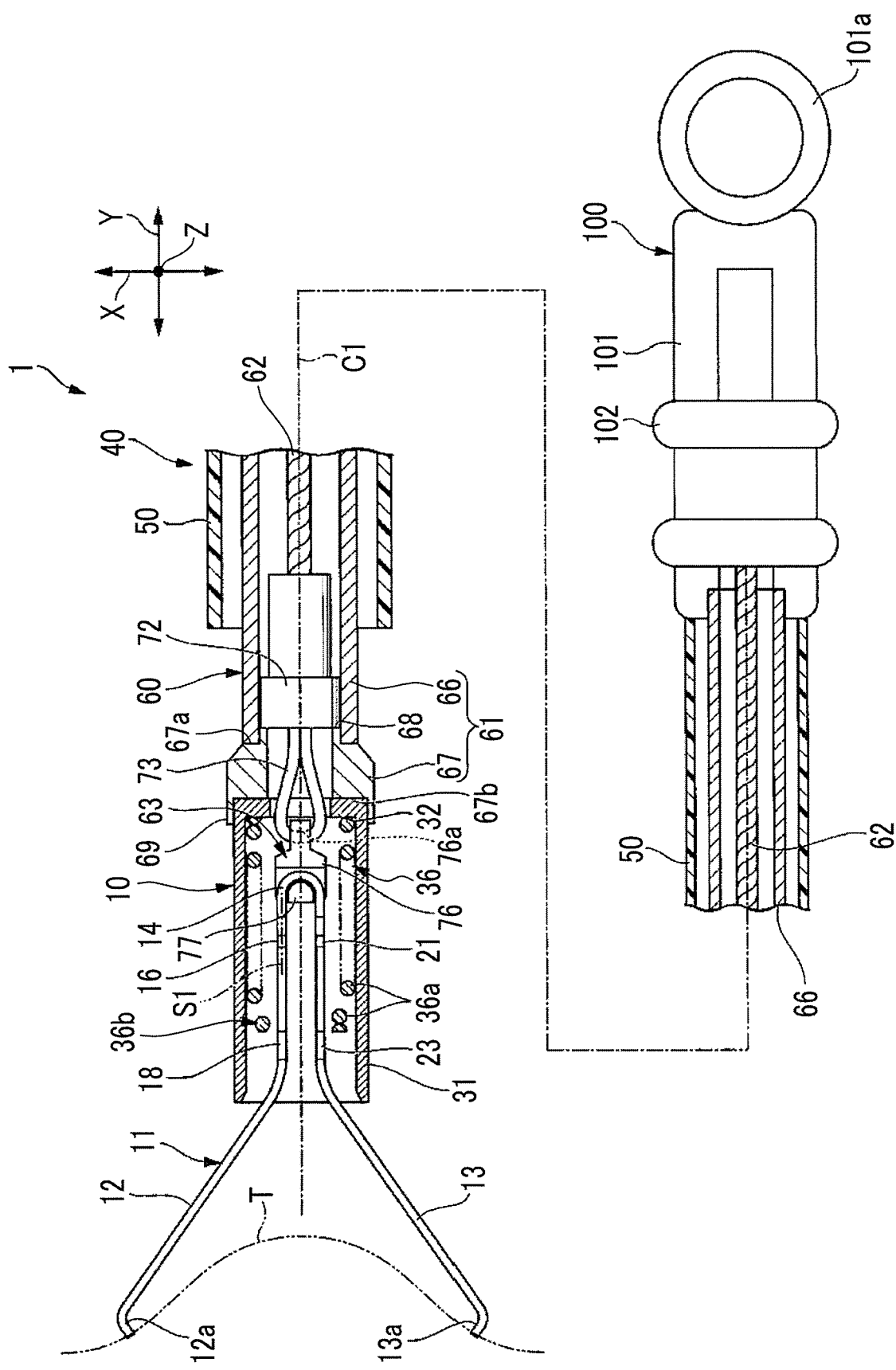
FIG. 3 is a cross-sectional view illustrating a side surface of an embodiment of a first treatment tool of a clip treatment tool related to the invention.
Figure 4:
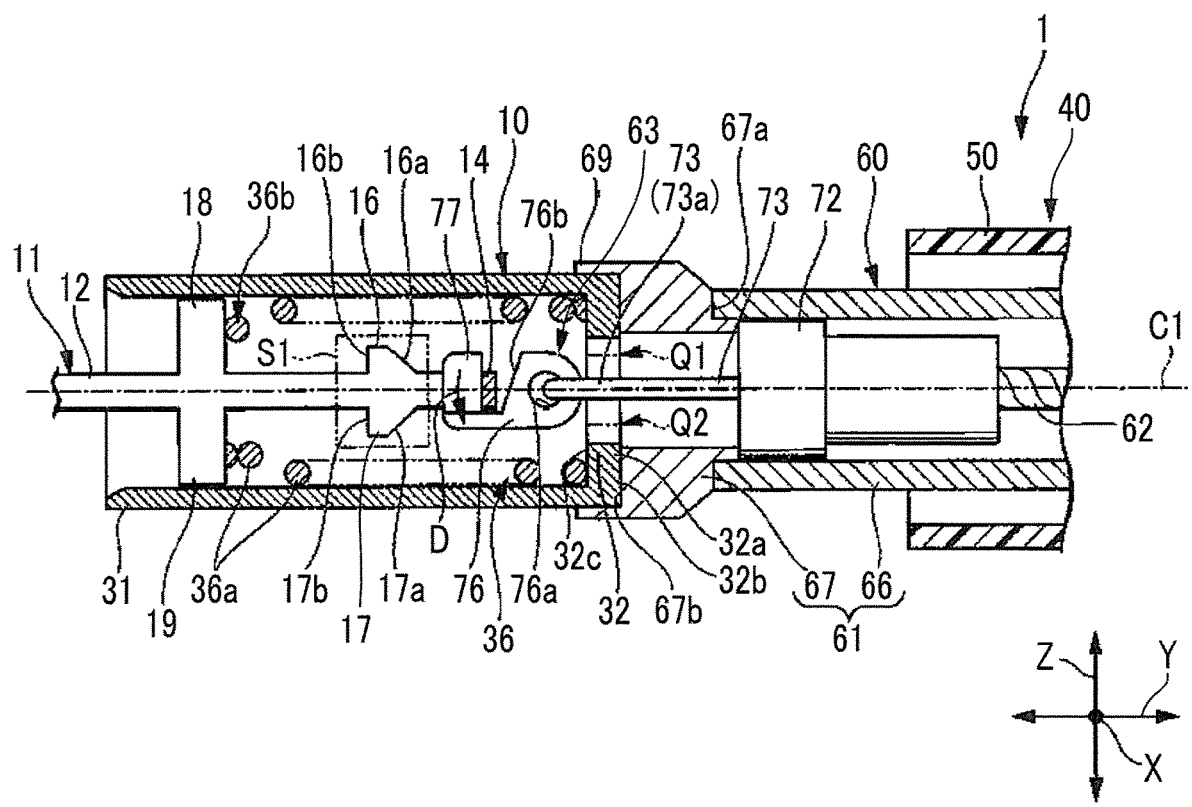
FIG. 4 is a cross-sectional view illustrating a plane of the first treatment tool illustrated in FIG. 3.

FIG. 3 is a cross-sectional view illustrating a side surface of an embodiment of the first treatment tool of the clip treatment tool related to the invention, and FIG. 4 is a cross-sectional view illustrating a plane of the first treatment tool illustrated in FIG. 3.

The first treatment tool 1 illustrated in FIGS. 3 and 4 is inserted the patient's body from the treatment tool insertion port 136 of the endoscope 114, is protruded from the treatment tool delivery port 144 to ligate a treatment part T with a clip, and comprises a clip 10 and a treatment tool body 40. The clip 10 is attachably and detachably attached to a distal end of the treatment tool body 40. In addition, in the clip treatment tool of the invention, the side of the treatment part is a distal side and the side of an operator is a proximal side.

(Configuration of Clip 10)

First, the configuration of the clip 10 will be described.

As illustrated in FIGS. 3 and 4, the clip 10 comprises the clip body 11, a retaining pipe 31, and a helical spring (a spring member of the invention) 36. That is, the clip 10 is configured as a clip unit in which the clip body 11, the retaining pipe 31, and the helical spring 36 are unitized.

Constituent members of the clip 10 are formed from materials, such as cobalt chrome alloys, titanium, and stainless steel, and a patient is able to receive MRI (nuclear magnetic resonance image method) even after the clip 10 is indwelled within the patient's body.

(Configuration of Clip Body 11)

The clip body 11 constitutes an arm of the invention, and comprises a first arm 12, a second arm 13, and a central part 14.

The first arm 12 and the second arm 13 are disposed side by side so as to extend from the proximal side toward the distal side and face each other. Additionally, the first arm 12 and the second arm 13 are formed so as to be separated from each other from the proximal side toward the distal side in a natural state. The central part 14 is located between a proximal end of the first arm 12 and a proximal end of the second arm 13. The first arm 12 and the second arm 13 are connected to each other via the central part 14 and are capable of being opened and closed. A claw 12a extending toward the second arm 13 side is formed at a distal end of the first arm 12. A claw 13a extending toward the first arm 12 side is formed in the distal end of the second arm 13.

Here, as illustrated in FIG. 3, a facing direction X in which the first arm 12 and the second arm 13 face each other, an axial direction Y parallel to an axis C1 of the retaining pipe 31, and an orthogonal direction Z orthogonal to the facing direction X and the axial direction Y, respectively, are defined.

As illustrated in FIG. 4, a proximal end of the first arm 12 is provided with two first locked parts 16 and 17. The first locked parts 16 and 17 are provided to protrude in the orthogonal direction Z from a side surface of the first arm 12 on a reference surface S1 parallel to an axis (central axis) C1 of the retaining pipe 31. The first locked parts 16 and 17 protrude in directions opposite to each other. That is, the proximal end of the first arm 12 is provided with two protruding parts serving as the two first locked parts 16 and 17.

FIG. 4 is a view as seen in the direction orthogonal to the reference surface S1 illustrated in FIG. 3. In a plan view illustrated in FIG. 4, the first locked part 16 and the first locked part 17 are formed so as to be line symmetrical to the axis C1 of the retaining pipe 31. A proximal end surface 16a of the first locked part 16 is inclined so as to be separated from the first arm 12 (central axis C1) toward the distal side. A distal end surface 16b of the first locked part 16 is orthogonal to the axial direction Y. The proximal end surface 17a and the distal end surface 17b of the first locked part 17 are respectively formed so as to be line symmetrical to the proximal end surface 16a and the distal end surface 16b of the first locked part 16 with respect to the axis C1.

As illustrated in FIGS. 3 and 4, two protrusions 18 and 19 are provided on the distal side of the first locked parts 16 and 17 in the first arm 12. The protrusions 18 and 19 protrude in the orthogonal direction Z from the side surface of the first arm 12. The protrusion 18 and the protrusion 19 are formed so as to be line symmetrical to the axis C1 in a plan view. The length by which the protrusions 18 and 19 protrude from the first arm 12 is longer than the length by which the first locked parts 16 and 17 protrudes in the orthogonal direction Z from the first arm 12.

Figure 5:
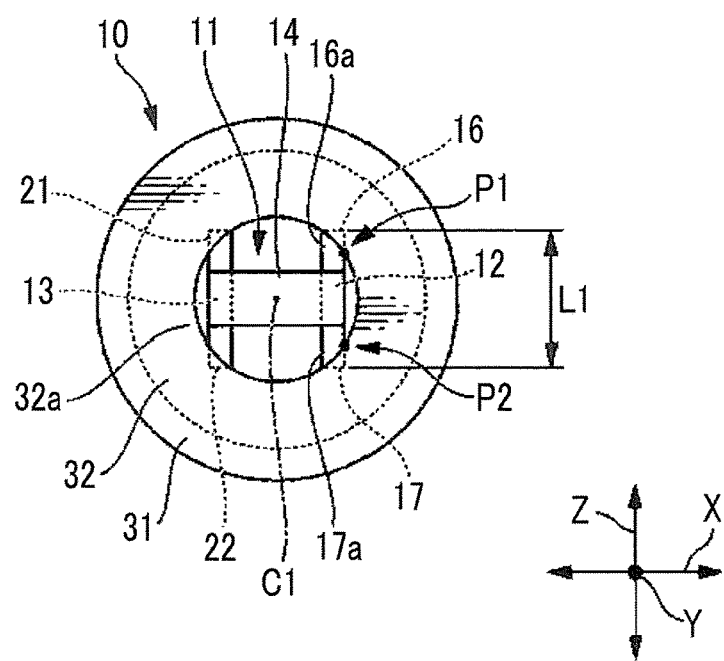
FIG. 5 is a front view of the proximal end surface of the clip in an initial state.

As illustrated in FIGS. 3 to 5, the second arm 13 is provided with second locked parts 21 and 22 (refer to FIG. 5 for the second locked part 22) and protrusions 23 and 24 that are formed similarly to the first locked parts 16 and 17 of the first arm 12 and protrusions 18 and 19 (refer to FIG. 5 for the protrusion 24). That is, the proximal end of the second arm 13 is provided with two protruding parts serving as two second locked parts 21 and 22, and the second locked parts 21 and 22 protrude in the orthogonal direction Z from a side surface of the second arm 13. The second locked parts 21 and 22 protrude in directions opposite to each other.

The protrusions 23 and 24 are provided on a distal side of the second locked parts 21 and 22 in the second arm 13 so as to protrude in the orthogonal direction Z from the side surface of the second arm 13. The second locked parts 21 and 22 and the protrusions 23 and 24, and the first locked parts 16 and 17 and the protrusions 18 and 19 are disposed side by side in the facing direction X, respectively. That is, in a plan view illustrated in FIG. 4, the second locked parts 21 and 22 overlap the first locked parts 16 and 17, and the protrusions 23 and 24 are disposed so as to overlap the protrusions 18 and 19.

The first locked parts 16 and 17 of the first arm 12 and the second locked parts 21 and 22 of the second arm 13 constitute protruding parts of a clip locking part of the invention.

In the side view illustrated in FIG. 3, the first arm 12 and the second arm 13 are formed at positions that are line symmetrical to the axis C1.

Additionally, the clip body 11 is bent at a connecting part between the first arm 12 and the central part 14 and a connecting part between the second arm 13 and the central part 14, and is integrally formed such that the central part 14 is C-shaped in the side view.

(Configuration of Retaining Pipe 31)

The retaining pipe 31 is formed in a cylindrical shape, and houses a proximal end of the clip body 11.

As illustrated in FIGS. 4 and 5, a locking part 32 protrudes over the entire circumference on an inner peripheral surface of the proximal end of the retaining pipe 31. The retaining pipe 31 and the locking part 32 are integrally formed.

As seen from the axial direction Y illustrated in FIG. 5, an edge part 32a on the axis C1 side in the locking part 32 is formed as a hole part in a circular shape that is coaxial with of the retaining pipe 31. That is, the edge part 32a formed at a proximal end of the retaining pipe 31 constitutes an opening part of the clip locking part of the invention. In the following, the edge part 32a of the locking part 32 is also referred to as an opening part 32a. Hence, the locking part 32 can be referred to as a disk member that has the opening part 32a serving as the circular hole part at a center thereof.

As illustrated in FIG. 4, a proximal end surface 32b (proximal side end surface) and a distal end surface 32c (distal side end surface) of the locking part 32 are orthogonal to the axial direction Y As illustrated in FIG. 5, the length in the orthogonal direction Z from an end of the first locked part 16 of the first arm 12 to an end of the first locked part 17 and a length L1 in the orthogonal direction Z from an end of the second locked part 21 of the second arm 13 to an end of the second locked part 22 are smaller than the internal diameter of the locking part 32. In contrast, the length in the orthogonal direction Z from an end of the protrusion 18 of the first arm 12 to an end of the protrusion 19 and the length in the orthogonal direction Z from an end of the protrusion 23 of the second arm 13 to an end of the protrusion 24 are larger than the internal diameter of the locking part 32. Hence, the portion of the first arm 12 on the proximal side of the protrusions 18 and 19, the portion of the second arm 13 on the proximal side of the protrusions 23 and 24, and the central part 14 are insertable into the opening part 32a of the locking part 32.

As illustrated in FIG. 5, the length L1 in the orthogonal direction Z from the first locked part 16 to the first locked part 17 of the first arm 12 is smaller than the internal diameter of the opening part 32a of the locking part 32, as described above. Additionally, in an initial state to be described below, as seen from the axial direction Y, a portion of each of the first locked parts 16 and 17 are set so as to overlap the locking part 32. That is, in a state illustrated in FIG. 5, the opening part 32a faces the first locked parts 16 and 17 at positions P1 and P2, and the length L1 of the first locked parts 16 and 17 is set so as to be longer than the height (the length of a line segment that connects the position P1 and the position P2 in FIG. 5 to each other) of the positions P1 and P2 of the opening part 32a in the orthogonal direction Z. In a case of the second locked parts 21 and 22 of the second arm 13, similarly, the length L1 of the second locked parts 21 and 22 is set so as to be longer than the length of the line segment that connects the position P1 and the position P2 to each other. In other words, the external diameter of the protruding parts defined as the diameter of a circumscribed circle circumscribed on the first locked parts 16 and 17 of the first arm 12 and the second locked parts 21 and 22 of the second arm 13 is larger than the internal diameter of the opening part 32a.

In addition, in the invention, the clip body may have two or more arms and the distal ends of the protruding parts are equal to or more than four on both sides. Thus, the external diameter of the protruding parts is defined as the diameter of a circumscribed circle circumscribed on distal ends of protruding parts of the two or more arms. Additionally, in the invention, the opening part of the locking part of the retaining pipe may be an opening of any shape. Thus, the internal diameter of the opening part is defined as the diameter of an inscribed circle inscribed on the opening of the opening part.

First, in the clip body 11 of the clip 10, the arms 12 and 13 of the clip body 11 are brought into the open state, next, the arms 12 and 13 of the clip body 11 are brought into the closed state in a state where the distal ends of the arms 12 and 13 brought into the open state in the clip body 11 are pressed against the treatment part T, and subsequently, the treatment part T is ligated by the claws 12a and 13a of the distal ends of the arms 12 and 13 brought into the closed state in the clip body 11. Thereafter, the first locked parts 16 and 17 of the first arm 12, the second locked parts 21 and 22 of the second arm 13, and the opening part 32a of the locking part 32 of the retaining pipe 31 that constitute the clip locking part of the invention lock the arms 12 and 13 of the clip in the closed state.

In a case where the clip body 11 is relatively moved to the proximal side of the retaining pipe 31, the first locked parts 16 and 17 of the first arm 12 and the second locked parts 21 and 22 of the second arm 13, that is, the protruding parts constituting the clip locking part of the invention have a smaller external diameter than the internal diameter of the opening part 32a of the locking part 32 and exceeds the opening part 32a of the retaining pipe 31, the external diameter of the protruding parts becomes larger than the internal diameter of the opening part 32a, the protruding parts and the opening part 32 are engaged with each other, and thereby, the arms 12 and 13 of the clip 10 are locked to each other in the closed state.

Namely, as illustrated in FIG. 5, in a case where the first arm 12 and the second arm 13 approach the central axis C1 from a state where P1, P2, and the like abut against the opening part 32a of the locking part 32 in the distal end surface 32c of the locking part 32 of the retaining pipe 31, and the like, the external diameter of the protruding parts equal to the length L1 of each of the first locked parts 16 and 17 and the second locked parts 21 and 22 becomes smaller than the internal diameter of the opening part 32a of the locking part 32 of the retaining pipe 31.

As a result, in a case where the first locked parts 16 and 17 and the second locked parts 21 and 22 exceed the opening part 32a, the first arm 12 and the second arm 13 will separate from the central axis C1 mutually, the external diameter of the protruding parts will become larger than the internal diameter of the opening part 32a, and the above length L1 will become larger than the length between P1 and P2. As a result, as the first locked parts 16 and 17 and the second locked parts 21 and 22, and the opening part 32a are engaged with each other, the arms 12 and 13 of the clip body 11 are locked to the closed state.

(Configuration of Helical Spring 36)

The helical spring 36 biases the clip body 11 housed within the retaining pipe 31 to a distal side of the retaining pipe 31. As illustrated in FIGS. 3 and 4, a seat winding part 36b is provided at a distal end of the helical spring 36.

The helical spring 36 is housed within the retaining pipe 31, has a distal end (seat winding part 36b) locked to the protrusions 18 and 19 and the protrusions 23 and 24, and has a proximal end locked to the distal end surface 32c of the locking part 32.

The portion of the first arm 12 on the proximal side of the protrusions 18 and 19, the portion of the second arm 13 on the proximal side of the protrusions 23 and 24, and the central part 14 are insertable into the helical spring 36. In a case where protrusions 18, 19, 23, and 24 have moved to the proximal side, the protrusions 18, 19, 23, and 24 are locked to the seat winding part 36b of the helical spring 36.

The helical spring 36 is compressed as the clip body 11 is relatively moved to the proximal side of the retaining pipe 31. The arms 12 and 13 of the clip 10 are locked to the closed state after the clip body 11 is biased to the distal side of the retaining pipe 31 by the helical spring 36.

On the other hand, the helical spring 36 is extended and relatively moves the clip body 11 to the distal side of the retaining pipe 31 in a case where the locking of the arms 12 and 13 of the clip 10 is released. The arms 12 and 13 of the clip 10 are brought into the open state as the arms 12 and 13 are protruded from the distal end of the retaining pipe 31.

In the initial state of the clip 10 illustrated in FIGS. 3 and 4, the proximal end of the first arm 12, the proximal end of the second arm 13, and the central part 14 are housed on the distal side of than the locking part 32 within the retaining pipe 31. The first locked parts 16 and 17 and the second locked parts 21 and 22 are not in contact with the locking part 32 of the retaining pipe 31. Bare wires 36a adjacent to each other in the axial direction Y of the helical spring 36 are spaced apart from each other, and the helical spring 36 is compressed in the axial direction Y slightly more than in the natural state. The distal end of the first arm 12 and the distal end of the second arm 13 in the clip body 11 are in a relatively spaced open state.

(Relationship Between Clip Body 11 and Retaining Pipe 31)

In the clip 10 configured as described above, the first arm 12 and the second arm 13 are spaced apart from each other in the facing direction X in the initial state. For this reason, in a case where the first locked part 16 is projected to the proximal side as illustrated in FIG. 5, the first locked part 16 overlaps the portion of the edge part 32a of the position P1 in the locking part 32.

In a case where the first arm 12 is moved to the proximal side with respect to the retaining pipe 31 in a state where the positions of the first arm 12 in the facing direction X and the orthogonal direction Z with respect to the retaining pipe 31 in the initial state are maintained, the proximal end surface 16a of the first locked part 16 comes into point contact with the portion of the position P1 of the edge part 32a. Similarly, in a case where the first arm 12 is moved to the proximal side with respect to the retaining pipe 31, the proximal end surface 17a of the first locked part 17 comes into point contact with the portion of the position P2 of the edge part 32a. The positions of the edge part 32a in the orthogonal direction Z corresponding to the positions P1 and P2 are illustrated as positions Q1 and Q2 in FIG. 4.

In a case where the first arm 12 is moved to the proximal side with respect to the retaining pipe 31, the second arm 13 formed integrally with the first arm 12 also moves to the proximal side with respect to the retaining pipe 31. In this case, similarly to the first locked parts 16 and 17 of the first arm 12, respective inclined proximal end surfaces (not illustrated) of that the second locked parts 21 and 22 are in contact with the edge part 32a of the locking part 32 of the retaining pipe 31.

(Configuration of Treatment Tool Body 40)

Subsequently, the, the configuration of the treatment tool body 40 will be described.

As illustrated in FIGS. 3 and 4, the treatment tool body 40 comprises an overtube 50, an insertion part 60 inserted through the overtube 50 so as to be movable forward and backward, and an operating part 100 (a first operating part of the invention) attached to a proximal end of the insertion part 60.

(Configuration of Insertion Part 60)

The insertion part 60 comprises a sheath part 61, an operating wire 62, and a coupling member 63.

The operating wire 62 is inserted through the sheath part 61 so as to be movable forward and backward. The coupling member 63 is disposed within the retaining pipe 31. The coupling member 63 is connected to a distal end of the operating wire 62, and is provided so as to be rotationally movable about an axis parallel to the facing direction X with respect to the operating wire 62.

The sheath part 61 comprises a coiled sheath 66, and a distal end member (stopper part) 67 fixed to a distal end of the coiled sheath 66.

The distal end member 67 is formed in a cylindrical shape, and the internal diameter thereof is smaller than the internal diameter of the coiled sheath 66. The external diameter of the distal end member 67 is larger than the coiled sheath 66 or the retaining pipe 31. A recess 67a is formed in an outer peripheral surface of a proximal end of the distal end member 67 by reducing the external diameter of the proximal end. The distal end member 67 and the coiled sheath 66 are fixed to each other in a state where the recess 67a is engaged with the distal end of the coiled sheath 66.

In this way, a stepped part 68 is formed at a connection portion between the coiled sheath 66 and the distal end member 67 on the inner peripheral surface of the distal end of the sheath part 61 by reducing the internal diameter of the distal end member 67 on the distal side of the coiled sheath 66 with respect to the coiled sheath 66. The internal diameter of the distal end member 67 is formed to be large enough to prevent the distal end member 67 from meshing with the first locked parts 16 and 17 and the second locked parts 21 and 22 in a case where the clip 10 is brought into a locked state as will be described below.

A recess is formed over the entire circumference of an inner peripheral surface of a distal end of the distal end member 67. A distal side of this recess is a supporting member 69. In this example, the supporting member 69 is formed in a cylindrical shape. The internal diameter of the supporting member 69 is slightly larger than the external diameter of the retaining pipe 31, and is capable of receiving the proximal end of the retaining pipe 31. In the recess of the inner peripheral surface of the supporting member 69, a surface facing forward becomes a distal end support surface (distal end surface) 67b. The distal end support surface 67b is capable of abutting against a proximal end surface of the retaining pipe 31. The supporting member 69 can support an outer peripheral surface of the retaining pipe 31 that has abutted against the distal end support surface 67b. In this example, the clip 10, more specifically, the retaining pipe 31 is attachably and detachably disposed at the distal end of the sheath part 61.

A loop part 73 is provided via a diameter-enlarged part 72 at the distal end of the operating wire 62.

The diameter-enlarged part 72 is formed in a cylindrical shape. The external diameter of the diameter-enlarged part 72 is smaller than the internal diameter of the coiled sheath 66, and is larger than the internal diameter of the distal end member 67. As a distal end surface of the diameter-enlarged part 72 abuts against the stepped part 68, the amount of protrusion of the loop part 73 with respect to the sheath part 61 is restricted to a length L2 illustrated in FIG. 17. This length L2 is the maximum amount of protrusion of the loop part 73 allowed by the distal end member 67.

The loop part 73 is formed by bending a wire 73a. Both ends of the wire 73a bent, which are such that the bent part becomes a distal side, are fixed to the diameter-enlarged part 72.

The coupling member 63 has a hook part 77 at a distal end of the coupling part body 76, and is configured such that a through-hole 76a is formed in a proximal end of the coupling part body 76. An inclined surface 76b is formed on the surface of the coupling part body 76 that faces the hook part 77. By inserting a bent part of the wire 73a of the loop part 73 through the through-hole 76a, the coupling member 63 is connected to so as to be rotationally movable (rotationally movable about in the direction of an arrow D of FIG. 4) about the axis parallel to the facing direction X with respect to the loop part 73.

The width (an external diameter in a direction orthogonal to the central axis C1 of the coupling part body 76 in a case where the hook part 77 is disposed to be on the distal side) of the coupling member 63 is slightly smaller than the internal diameter of the helical spring 36, the internal diameter of the coiled sheath 66, and the internal diameter of the distal end member 67. That is, the coupling member 63 cannot be rotationally moved with respect the loop part 73 within the retaining pipe 31 and the sheath part 61 from a state where the hook part 77 is disposed to be on the distal side. In other words, the relative movement of the clip body 11 and the hook part 77 in the radial direction is restricted by the retaining pipe 31 and the sheath part 61. Additionally, the width of the coupling member 63 is slightly smaller than the internal diameter of the opening part 32a of the locking part 32. Therefore, in a case where the coupling member 63 is moved to the proximal side, the coupling member 63 passes through the opening part 32a, and is moved from the inside of the retaining pipe 31 to the outside thereof on the proximal side, that is, the insides of the coiled sheath 66 and the distal end member 67.

By disposing the central part 14 between the hook part 77 and the inclined surface 76b of the coupling member 63, the hook part 77 can be engaged with the central part 14. In a case where the hook part 77 has been rotationally moved in the direction D (refer to FIG. 4) with respect to the loop part 73, the engagement between the hook part 77 and the central part 14 is released. In this way, the coupling member 63 is attachably and detachably coupled to the clip body 11.

(Configuration of Operating Part 100)

As illustrated in FIG. 3, the operating part 100 comprises an operating part body 101 and a slider 102.

The operating part body 101 is attached to a proximal end of the coiled sheath 66, in other words, a proximal end of the sheath part 61. The slider 102 is externally fitted to the operating part body 101, and is provided so as to be slidable in the axial direction Y with respect to the operating part body 101. A proximal end of the operating wire 62 is connected to the slider 102.

(Operation of Treatment Tool Body 40)

Since the slider 102 is connected to the operating wire 62, in a case where the slider 102 is pulled to the proximal side with respect to the operating part body 101, the operating wire 62 can be pulled to the proximal side and can pull back the clip body 11 with respect to the retaining pipe 31. That is, by operation the operating part 100, the arms 12 and 13 can be brought into the closed state as the arms 12 and 13 protruded from the distal end of the retaining pipe 31 are housed within the retaining pipe 31.

On the other hand, the operating wire 62 is moved to the distal side by being operated so as to move the slider 102 to the distal side with respect to the operating part body 101. That is, by operating the operating part 100, the arms 12 and 13 can be brought into the open state as the clip body 11 is moved to the distal side with respect to the retaining pipe 31 and the arms 12 and 13 is protruded from the distal end of the retaining pipe 31.

That is, by sliding the slider 102 in the axial direction Y with respect to the operating part body 101, the operating wire 62 can be moved forward and backward in the axial direction Y, and the arms 12 and 13 can be opened and closed.

Next, the second treatment tool will be described.

The second treatment tool constitutes a clip removal part of the invention, the clip 10 in which the arms 12 and 13 are locked to the closed state is separated from the sheath part 61 and indwelled in the treatment part T (refer to FIG. 19) by the operation of the operating part 100 of the first treatment tool, and then, the locking of the arms 12 and 13 of the clip 10 indwelled in the treatment part T and locked to the closed state is released by the operation of the operating part of the second treatment tool. Additionally, as the locking is released, the arms 12 and 13 are brought into the open state, and the clip 10 removed from the treatment part T is maintained and taken out (refer to FIGS. 21 to 23).

Figure 22:
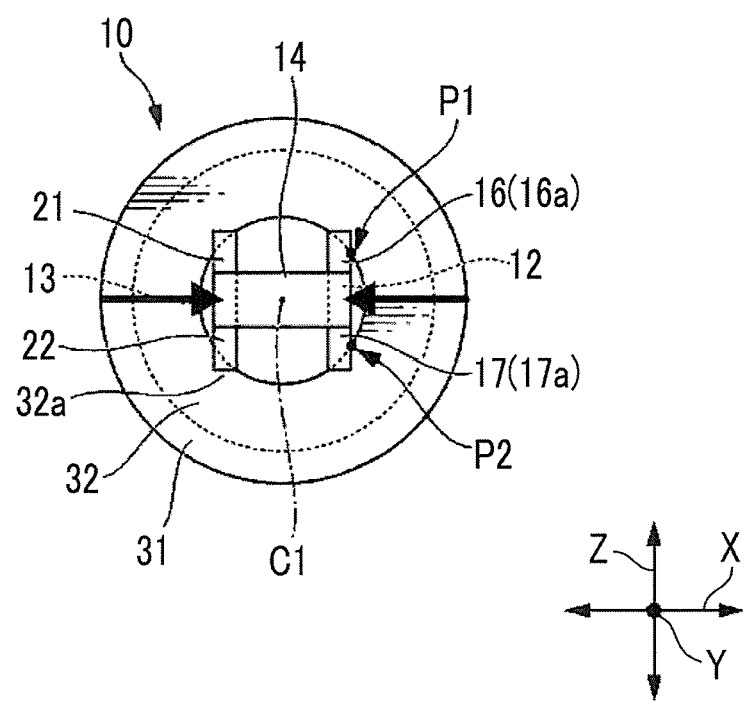
FIG. 22 is a conceptual diagram view illustrating a direction in which a first locked part and a second locked part of the arm of the clip in the locked state is presses by a claw member of the second treatment tool.
Figure 23:
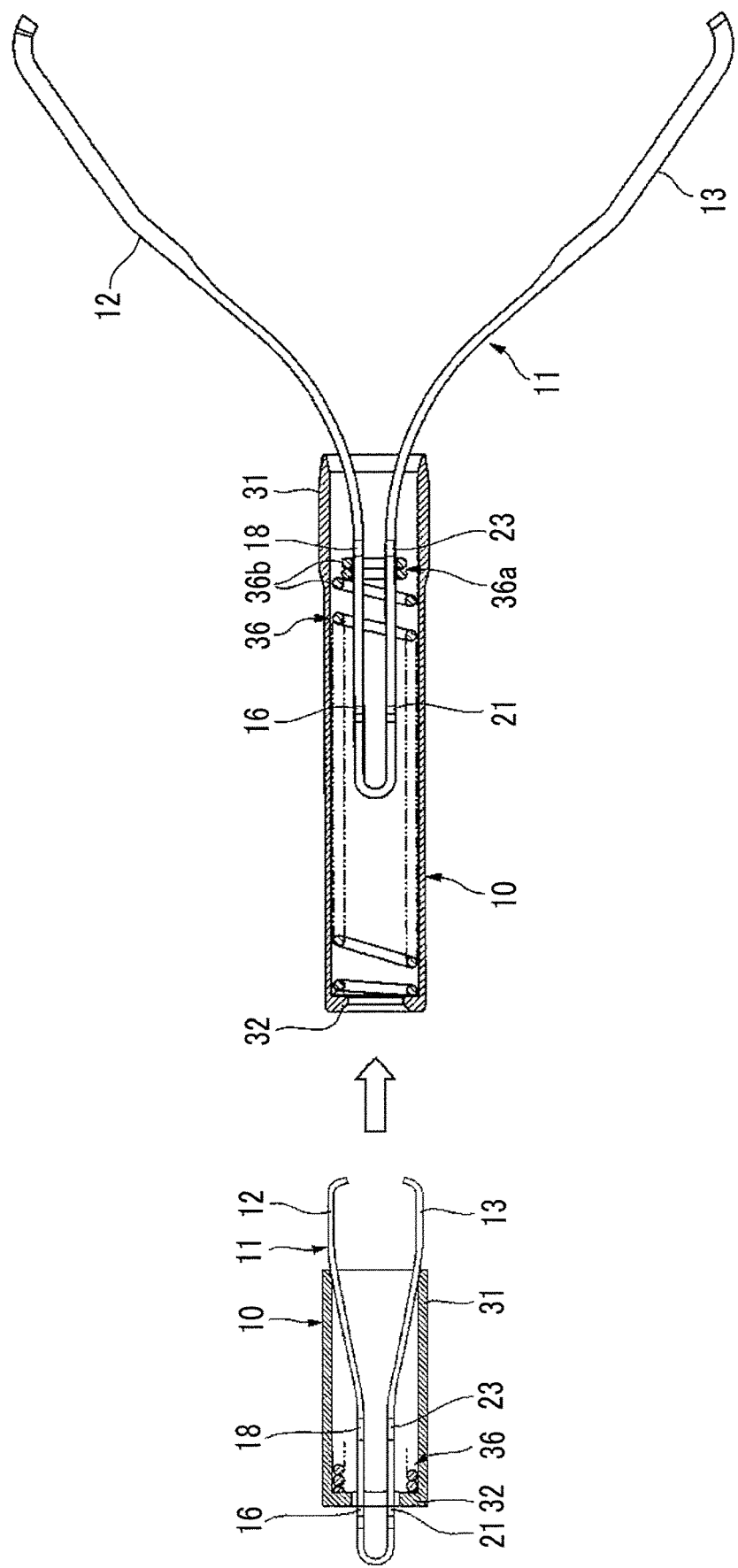
FIG. 23 is a cross-sectional view illustrating the plane of the first treatment tool in which the first arm and the second arm are brought into an open state.

The second treatment tool reduces the external diameter of the protruding parts of the clip 10, that is, the first locked parts 16 and 17 of the first arm 12 and the second locked parts 21 and 22 of the second arm 13 to be equal to or less than the internal diameter of the opening part 32a of the retaining pipe 31, and releases the locking of the arms 12 and 13 by releasing the engagement between the protruding parts and the opening part 32a (refer to FIGS. 22 to 23). In a case where the locking of the arms 12 and 13 is released, the helical spring 36 is extended to relatively move the clip body 11 to the distal side of the retaining pipe 31, and is brought into the open state as the arms 12 and 13 are protruded from the distal end of the retaining pipe 31 (refer to FIG. 23).

Figure 6:
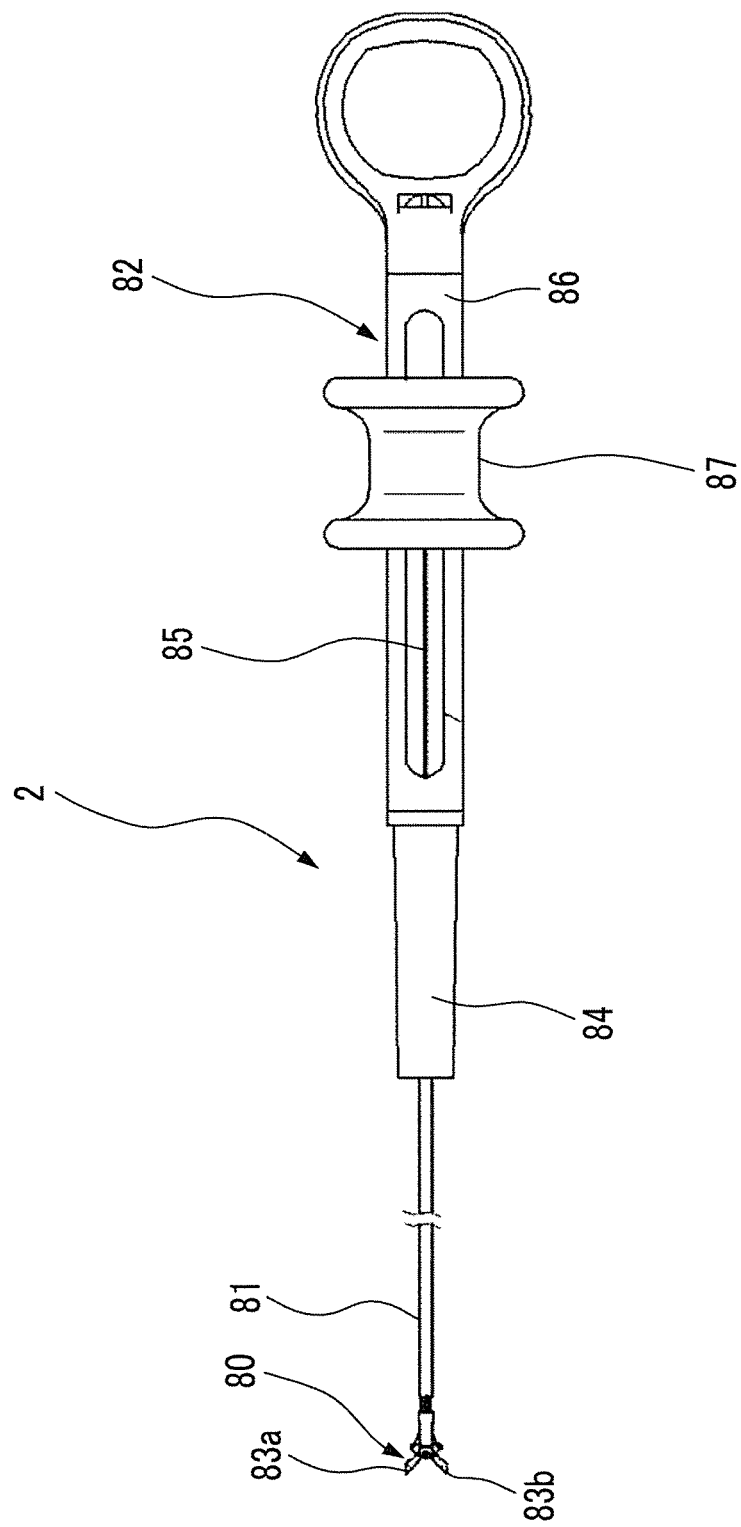
FIG. 6 is a side view illustrating the configuration of a first embodiment of a second treatment tool of the clip treatment tool related to the invention.

FIG. 6 is a side view illustrating the configuration of a first embodiment of the second treatment tool related to the invention. A second treatment tool 2 illustrated in FIG. 6 is gripping forceps that are inserted into the patient's body from the treatment tool insertion port 136 of the endoscope 114 illustrated in FIG. 1 and are protruded from the treatment tool delivery port 144 illustrated in FIG. 2 to hold and remove the clip indwelled within the patient's body, and comprises a distal end gripping part 80, an insertion part 81, and an operating part 82 (a second operating part of the invention). The distal end gripping part 80 is attached to a distal end of the insertion part 81, and the operating part 82 is attached to a proximal end of the insertion part 81.

(Configuration of Distal End Gripping Part 80)

The distal end gripping part 80 comprises a pair of claw members 83a and 83b. The claw members 83a and 83b constitute a gripping part, and are opened and closed by the operation of the operating part 82. The claw members 83a and 83b extend from the proximal side toward the distal side, and are disposed such that gripping surfaces therefor face each other in a closed state.

(Configuration of Insertion Part 81)

The insertion part 81 comprises a sheath 84 and an operating wire 85.

The operating wire 85 is inserted through the sheath 84 so as to be movable forward and backward. The distal end gripping part 80 is attached to a distal end of the sheath 84, and is connected to a distal end of the operating wire 85.

(Configuration of Operating Part 82)

The operating part 82 comprises an operating part body 86 and a slider 87.

The operating part body 86 is attached to a proximal end of the sheath 84. The slider 87 is externally fitted to the operating part body 86, and is provided so as to slide in an extending direction of the insertion part 81 with respect to the operating part body 86. A proximal end of the operating wire 85 is connected to the slider 87.

(Operation of Gripping Forceps)

The opening and closing operation of the claw members 83a and 83b is performed by the operating part 82. By moving the slider 87 to the proximal side with respect to the operating part body 86, the operating wire 85 is moved to the proximal side, and thereby, the pair of claw members 83a and 83b is brought into the closed state (gripped state). On the other hand, by moving the slider 87 to the distal side with respect to the operating part body 86, the operating wire 85 is moved to the distal side, and thereby, the pair of claw members 83a and 83b is brought into an open state (a non-gripped state).

The second treatment tool 2 reduces the external diameter of the protruding parts to be equal to or less than the internal diameter of the opening part 32a of the retaining pipe 31 by sandwiching and pressing the first locked parts 16 and 17 of the first arm 12 and the second locked parts 21 and 22 of the second arm 13, which are the protruding parts of the clip 10, with the pair of claw members 83a and 83b.

Figure 7:
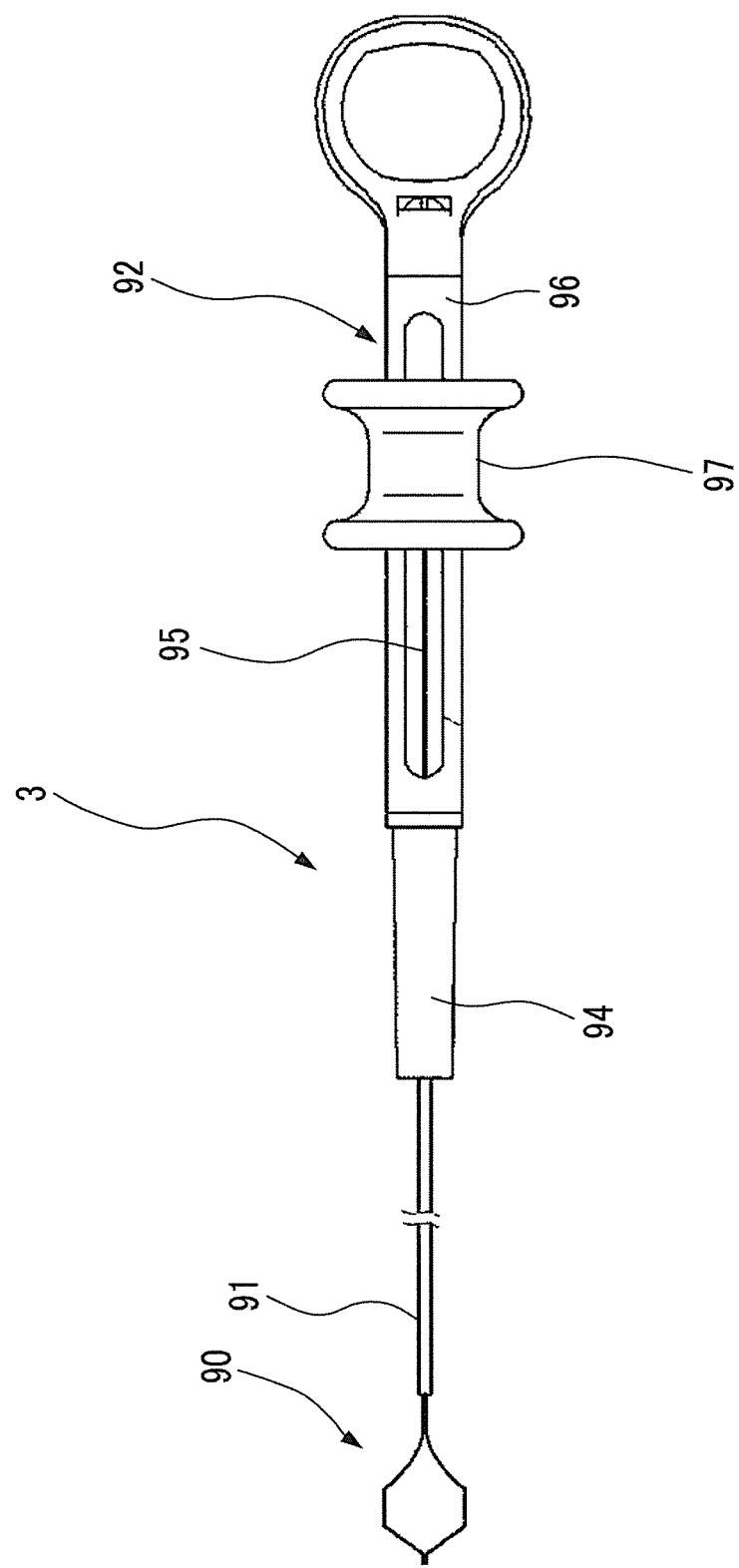
FIG. 7 is a side view illustrating the configuration of a second embodiment of the second treatment tool of the clip treatment tool related to the invention.

FIG. 7 is a side view illustrating the configuration of a second embodiment of the second treatment tool related to the invention. The second treatment tool 3 illustrated in FIG. 7 is a snare-like member that are inserted into the patient's body from the treatment tool insertion port 136 of the endoscope 114 illustrated in FIG. 1 and are protruded from the treatment tool delivery port 144 illustrated in FIG. 2 to hold and remove the clip indwelled within the patient's body, and comprises a loop part 90, an insertion part 91, and an operating part (a second operating part of the invention) 92. The loop part 90 is attached to a distal end of the operating wire 95 inserted through the insertion part 91 to be described below, and the operating part 92 is attached to a proximal end of the insertion part 91.

(Configuration of Loop Part 90)

The loop part 90 is formed by bending a wire. The bent part of the wire is directed to the distal side. The diameter of a loop of the loop part 90 is increased by the operation of the operating part 92.

(Configuration of Insertion Part 91)

The insertion part 91 comprises a sheath 94 and an operating wire 95.

The operating wire 95 is inserted through the sheath so as to be movable forward and backward. Both ends of the wire of the loop part 90 are attached to a distal end of the sheath 94, and are connected to a distal end of the operating wire 95.

(Configuration of Operating Part 92)

The configuration of the operating part 92 is the same as that of the operating part 82 illustrated in FIG. 6, and comprises an operating part body 96 and a slider 97.

(Function of Snare-Like Member)

The increasing and reducing operation of the diameter of the loop of the loop part 90 is performed by the operating part 92. By moving the slider 97 to the proximal side with respect to the operating part body 96, the operating wire 95 is moved to the proximal side, and thereby, the loop part 90 is housed within the sheath 94 and the diameter of the loop of the loop part 90 is reduced. On the other hand, by moving the slider 97 to the distal side with respect to the operating part body 96, the operating wire 95 is moved to the distal side, and thereby, the loop part 90 is protruded from the distal end of a sheath 94 and the diameter of the loop of the loop part 90 is increased.

The second treatment tool 3 reduces the external diameter of the protruding parts to be equal to or less than the internal diameter of the opening part 32a of the retaining pipe 31 by surrounding and clamping the first locked parts 16 and 17 of the first arm 12 and the second locked parts 21 and 22 of the second arm 13, which are the protruding parts of the clip 10, with the loop of the loop part 90.

Next, the operation in a case where the treatment part T within the patient's body is ligated by a clip and bleeding thereof is stopped will be described.

(Operation of Endoscope 114)

Figure 8A:
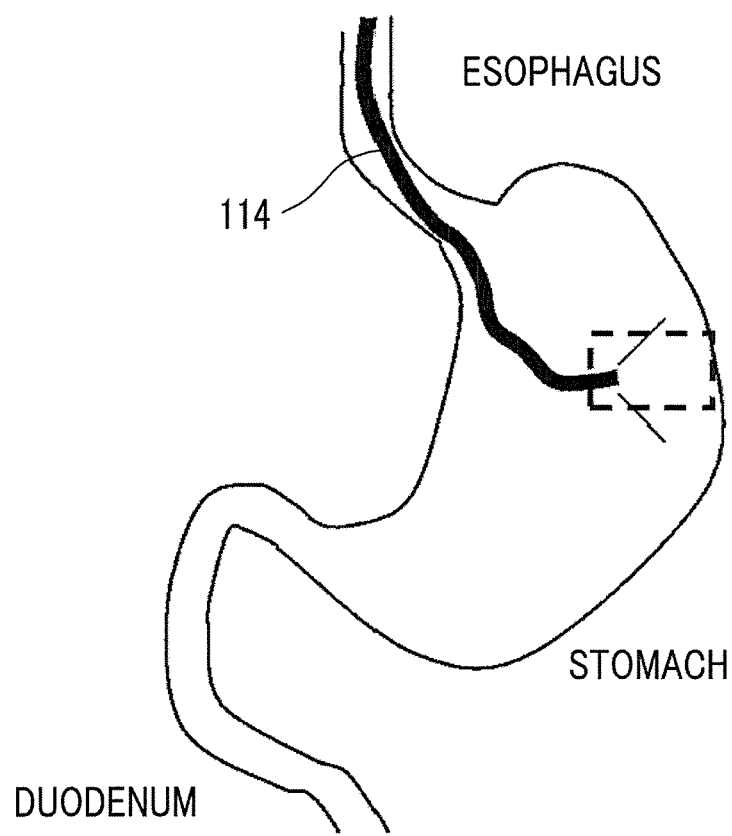
FIG. 8A is a conceptual diagram illustrating an aspect in which the distal end of the insertion part of the endoscope is brought close to a treatment part.
Figure 8B:
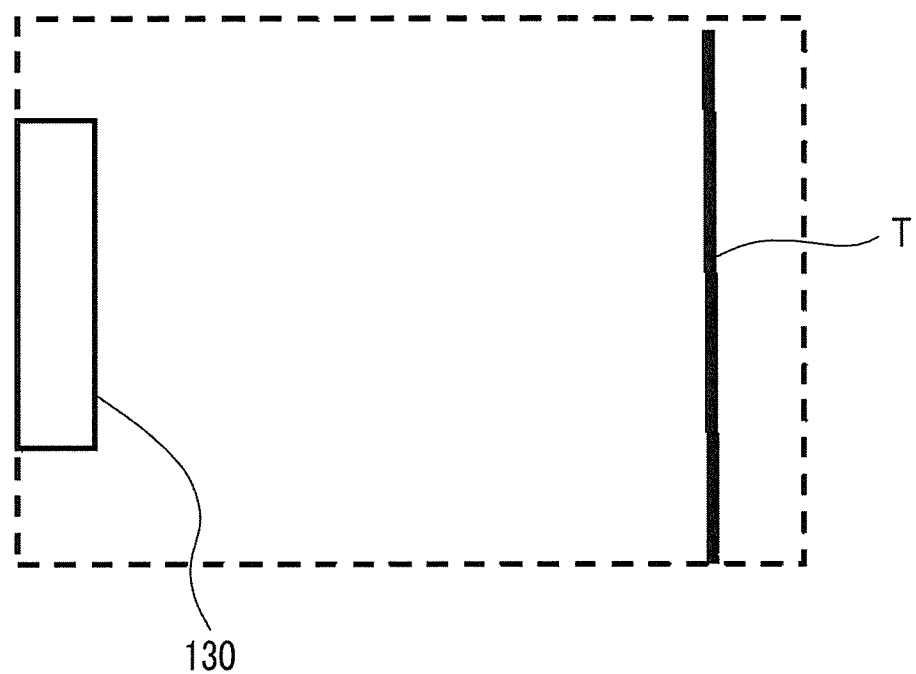
FIG. 8B is an enlarged view of a portion surrounded by a broken line in FIG. 8A.

First, the distal end 130 of the insertion part 124 is brought close to the treatment part T by inserting the insertion part 124 of the endoscope 114 illustrated in FIG. 1 into the patient's body, advancing the insertion part to the vicinity of the treatment part T while observing the appearance of the patient's body, and operating the angle knob 134 to bend the bending part 128. For example, as illustrated in FIGS. 8A and 8B, the distal end 130 of the insertion part 124 is moved forward to the vicinity of the treatment part T that is in a stomach side wall through an esophagus. FIG. 8B is an enlarged view of a portion surrounded by a broken line in FIG. 8A.

(Operation of Treatment Tool Body 40)

Next, the first treatment tool 1 will be described.

(Initial State)

Figure 9:
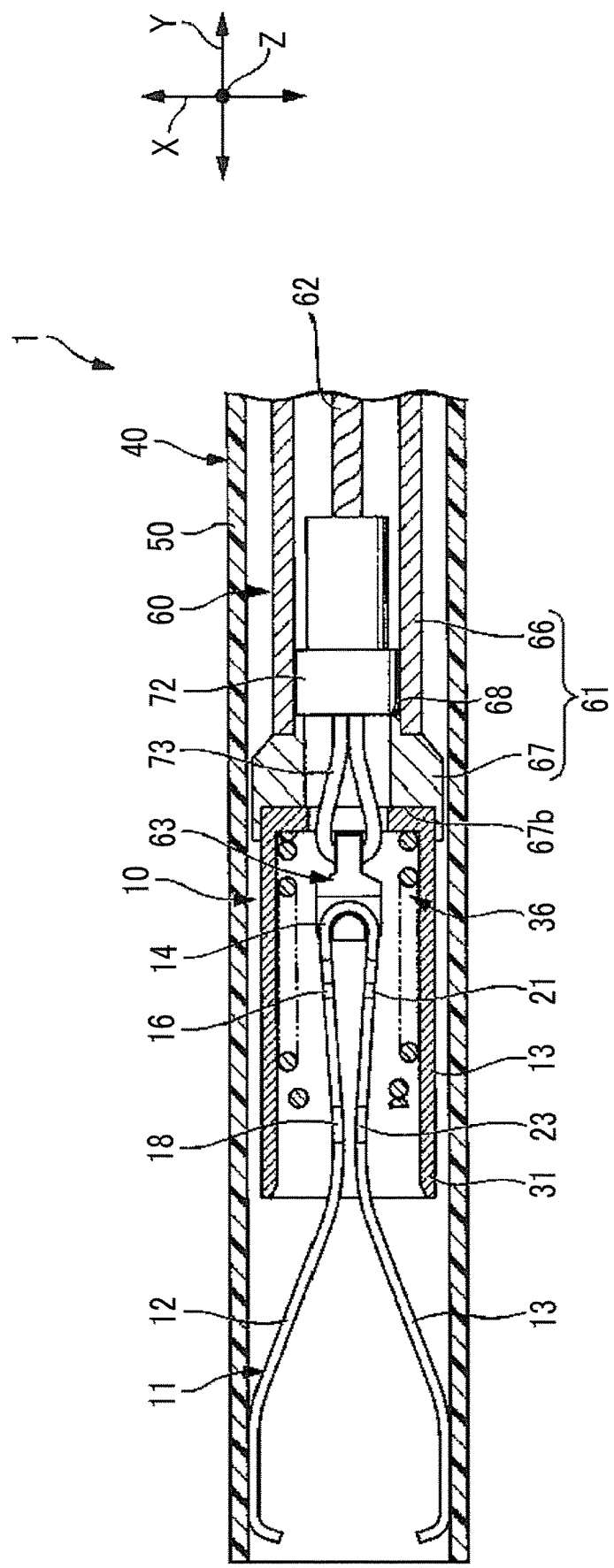
FIG. 9 is a cross-sectional view illustrating a side surface of the first treatment tool in an initial state.

In the first treatment tool 1, as illustrated in FIG. 9, in the initial state, the overtube 50 is pushed into the insertion part 60 such so as to cover the clip 10 in the state of being attached to the treatment tool body 40. The proximal end surface of the retaining pipe 31 abuts against the distal end support surface 67b. A distal end surface of the diameter-enlarged part 72 abuts against the stepped part 68, and the loop part 73 protrudes to the maximum amount of protrusion with respect to the distal end member 67.

Since the coupling member 63 is disposed within the retaining pipe 31, the coupling member 63 cannot be rotationally moved with respect to the loop part 73, and the engagement between the hook part 77 and the central part 14 is maintained.

Figure 10:
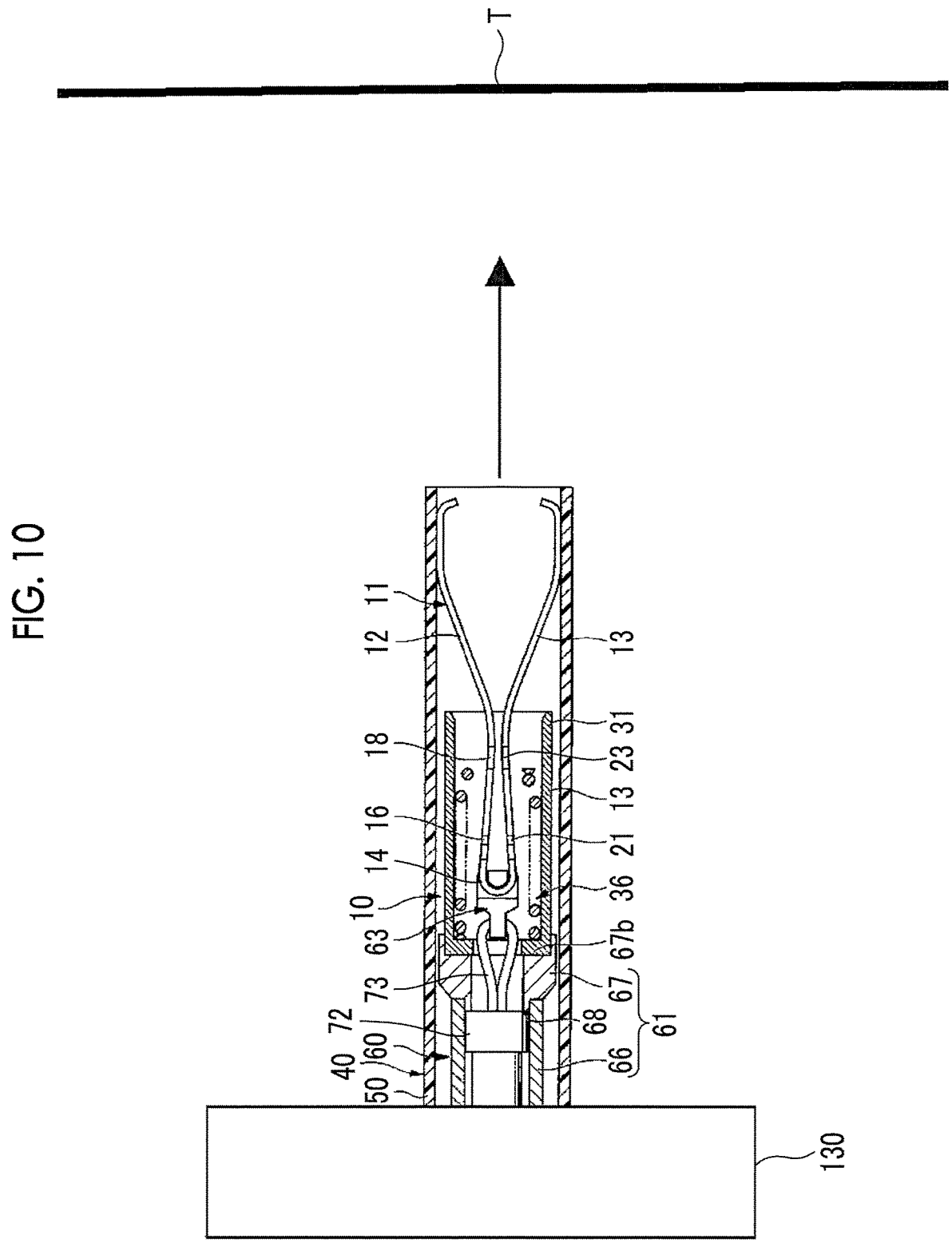
FIG. 10 is a conceptual diagram illustrating a state where a distal end of an overtube of the first treatment tool is protruded from a treatment tool delivery port of the endoscope.
Figure 11:
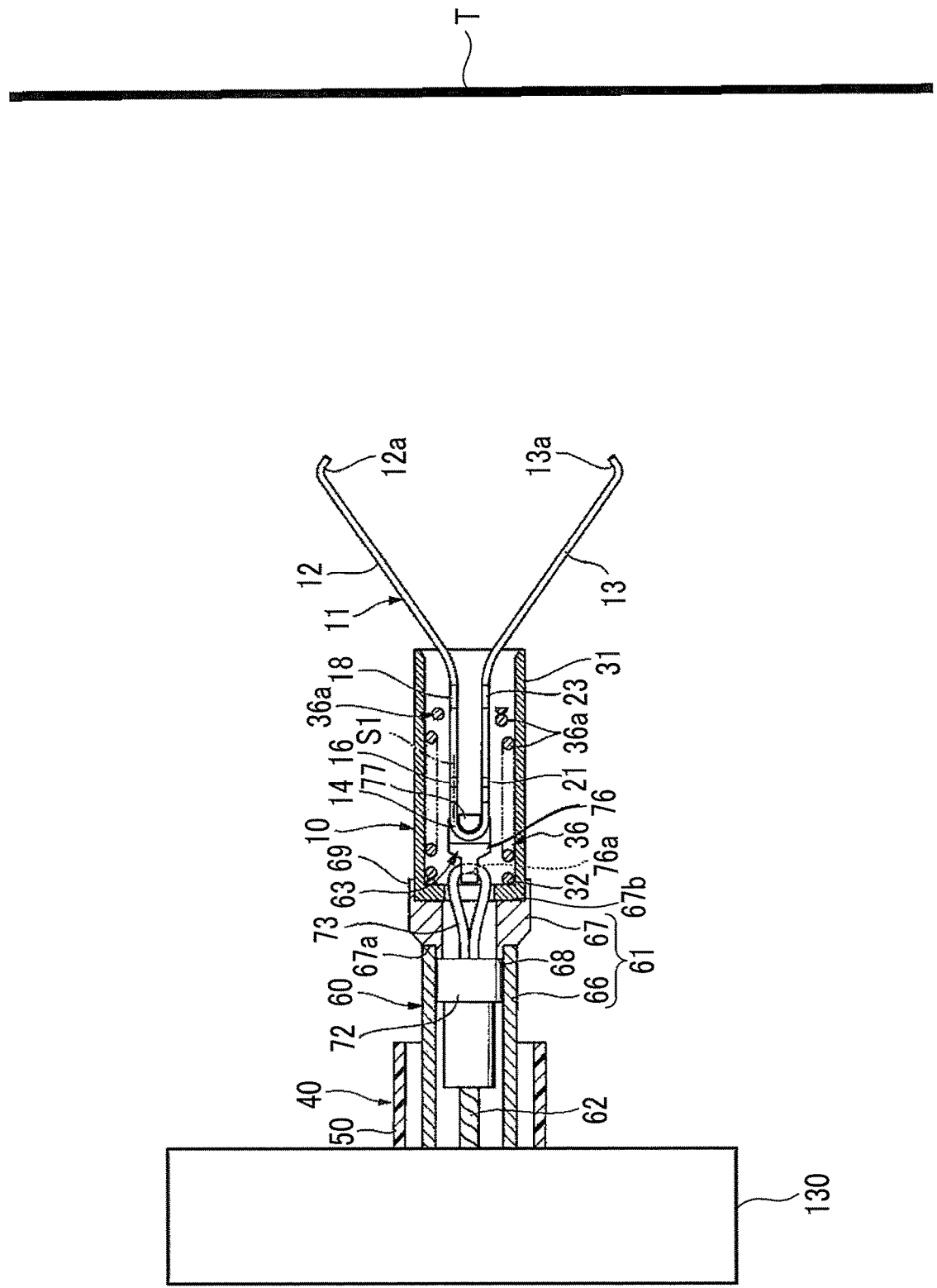
FIG. 11 is a conceptual diagram illustrating a state where the clip is protruded from the distal end of the overtube of the first treatment tool and an arm is brought into an open state.

At the time of use of the first treatment tool 1, the overtube 50 of the first treatment tool 1 is inserted from the treatment tool insertion port 136 of the endoscope 114 inserted into the patient's body, and the distal end of the overtube 50 is protruded from the treatment tool delivery port 144 of the endoscope 114 as illustrated in FIG. 10. Subsequently, as illustrated in FIG. 11, the clip 10 is protruded from a distal end of the overtube 50 by pulling back the overtube 50 with respect to the insertion part 60. In this way, by operating the operating part 100, the arms 12 and 13 of the clip 10 can be brought into the open state as the arms are protruded from the distal end of the sheath.

From the initial state illustrated in FIG. 3, the slider 102 is moved (pulled back) to the proximal side with respect to the operating part body 101. In accordance with the operation of pulling back the slider 102, the state of the clip 10 changes from the initial state to a contact state, a ride-over state, and a locked state as will be described below.

Subsequently, the clip 10 is made to face the treatment part T in the living body, for example, by bending the bending part provided in the insertion part 124 of the endoscope 114 while observing the inside of the patient's body with the endoscope 114. In addition, the orientation of the clip 10 can be adjusted by rotating the operating wire 62 with respect to the sheath part 61. By pushing the first treatment tool 1 into the endoscope 114, the distal ends of the arms 12 and 13 are pressed against the treatment part T.

Figure 12:
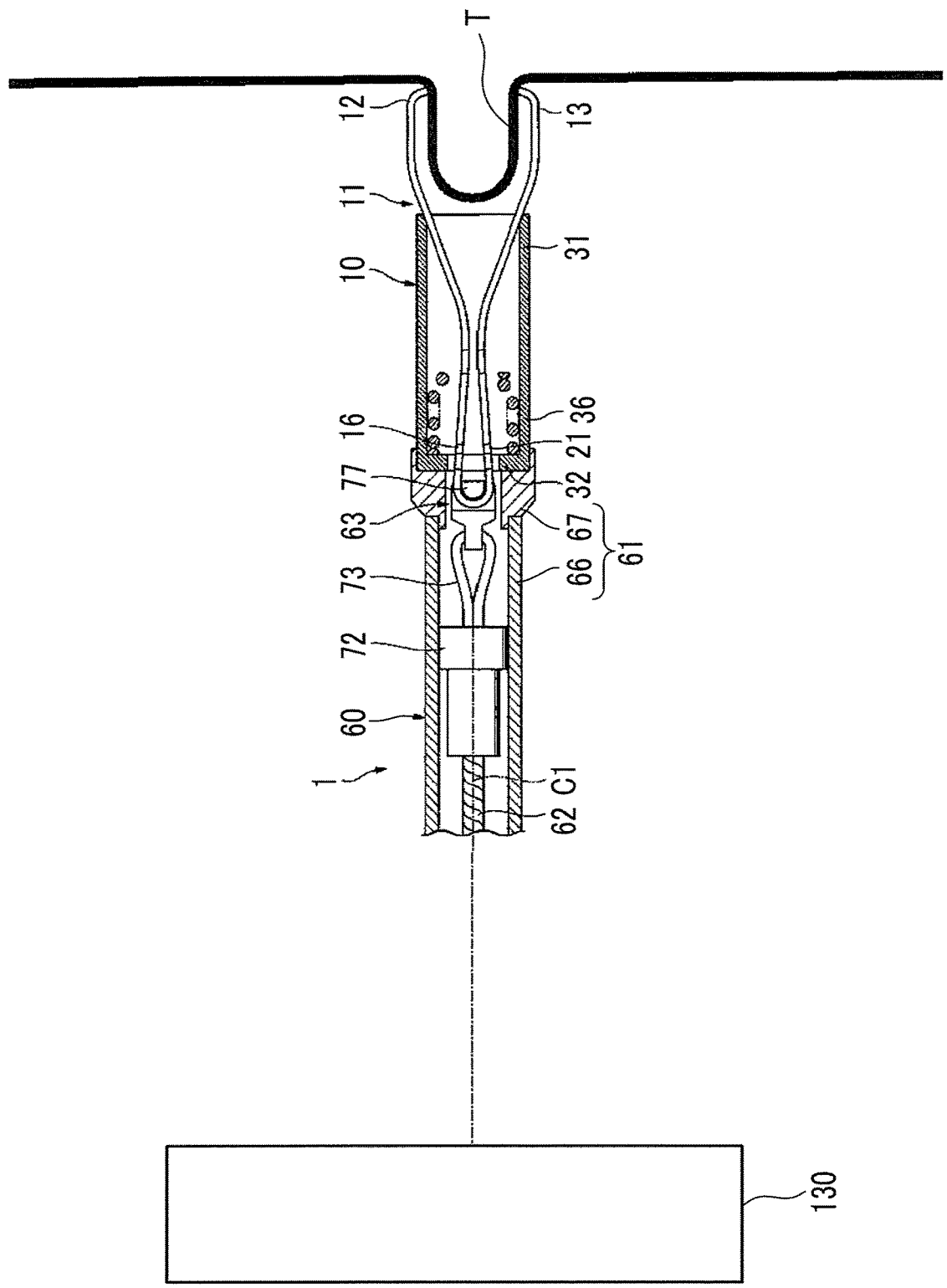
FIG. 12 is a conceptual diagram illustrating a state where the arm of the clip is brought into a closed state and a treatment part is ligated.

In a case where the distal ends of the arms 12 and 13 brought into the open state in the clip 10 grip the operating part 100 in a state where the distal ends are pressed against the treatment part T, and pull back the slider 102, the first arm 12 and the second arm 13 are biased to an inner peripheral surface of the distal end of the retaining pipe the 31. As a result, the first arm 12 is resiliently deformed to the second arm 13 side, the second arm 13 is elastically resiliently to the first arm 12 side, and as illustrated in FIG. 12, the distal end of the first arm 12 and the distal end of the second arm 13 approach each other. That is, by operating the operating part 100, the arms 12 and 13 of the clip 10 are brought into the closed state as the arms are housed within the retaining pipe 31, and the treatment part T is ligated by the claws 12a and 13a of the distal ends of the arms 12 and 13 that are brought into the closed state. Additionally, the helical spring 36 is compressed in the axial direction Y.

(Contact State from Initial State)

In a case where the slider 102 is further pulled back, the contact state where the first locked parts 16 and 17 and the second locked parts 21 and 22 come into contact with the locking part 32 of the retaining pipe 31 is brought about. In this case, as illustrated in FIG. 5, the first locked part 16 comes into contact with the position P1 in the edge part 32a of the retaining pipe 31, and the first locked part 17 comes into contact with the position P2.

The arms 12 and 13 of the clip 10 change from the open state to the closed state. Since the coupling member 63 is disposed within the retaining pipe 31 or the sheath part 61, the coupling member 63 cannot be rotationally moved with respect to the loop part 73, and the engagement between the hook part 77 and the central part 14 is maintained.

(Contact State from Ride-Over State)

The proximal end surfaces 16a and 17a of the first locked parts 16 and 17 are inclined as described above, and the edge part 32a has a circular shape. For this reason, in a case where the slider 102 is further pulled back, as seen in the axial direction Y illustrated in FIG. 13, the first locked part 16 receives a vertical drag from the edge part 32a in parallel with a normal line N orthogonal to a tangent line theta of the edge part 32a at the position P1 where the first locked part comes into contact with the edge part 32a of the locking part 32. By this vertical drag, the first locked part 16 of the first arm 12 moves in the facing direction X so as to approaches the second arm 13.

Figure 13:
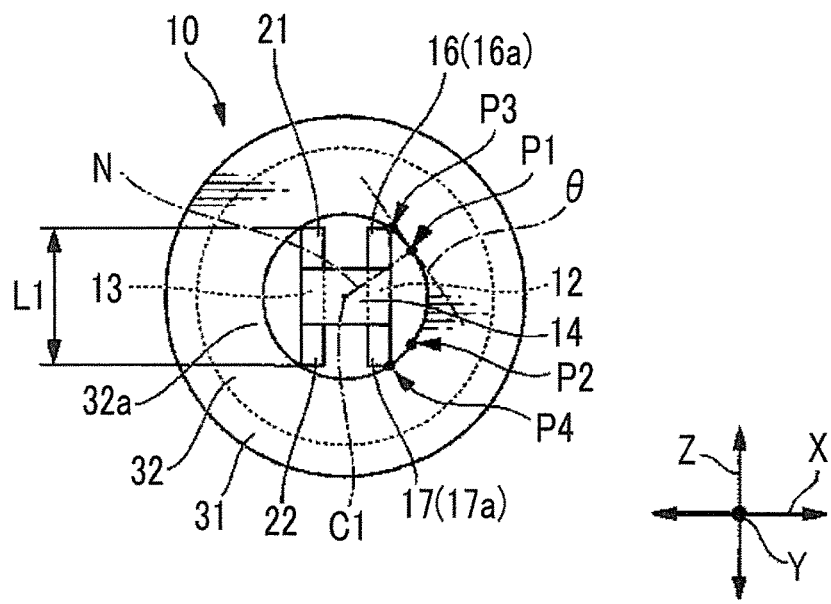
FIG. 13 is a front view of a proximal end surface of the clip in a ride-over state.
Figure 14:
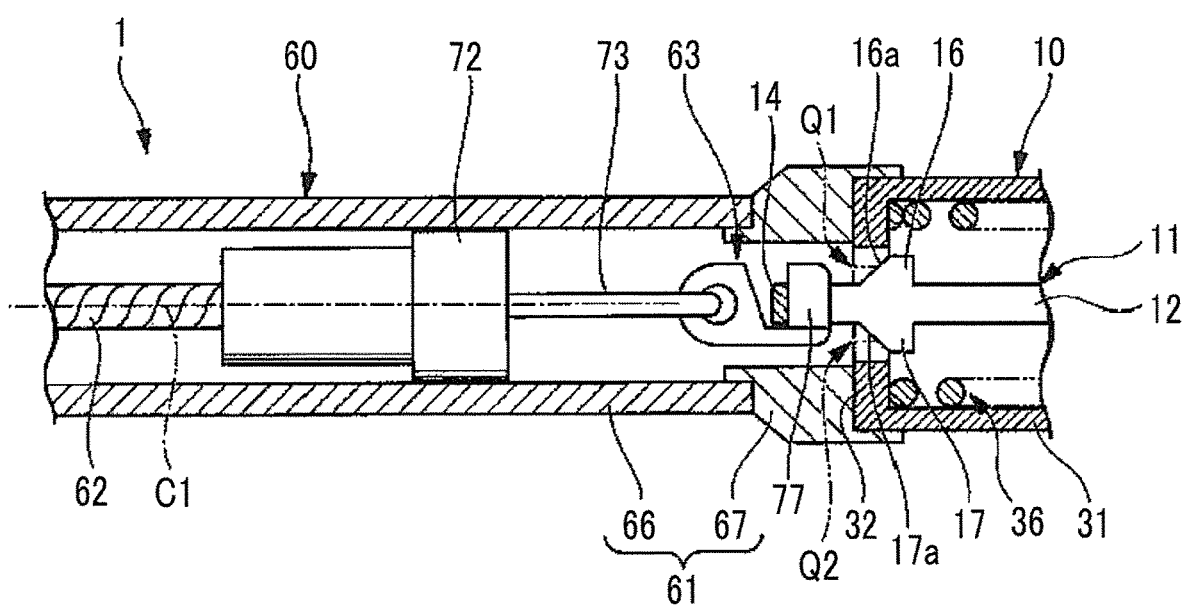
FIG. 14 is a cross-sectional view illustrating a plane of the first treatment tool in the ride-over state.

In a case where the pull-back operation is further continued, as illustrated in FIGS. 13 and 14, the edge part 32a of the locking part 32 with which the first locked part 16 comes in contact moves from the position P1 to the position P3 while the first locked parts 16 and 17 come into point contact with the locking part 32. Simultaneously with this, the edge part 32a of the locking part 32 with which the first locked part 17 comes into contact moves from the position P2 to the position P4. In addition, in FIGS. 13 and 14, the ride-over state where a distal end of the proximal end surface 16a of the first locked part 16 and a distal end of the proximal end surface 17a of the first locked part 17 have come into contact with the edge part 32a of the locking part 32 is illustrated.

Similarly, the second arm 13 receives a vertical drag from the edge part 32a of the locking part 32, and moves in the facing direction X so as to approach the first arm 12. In this case, the central part 14 is elastically deformed such that both ends thereof move to the axis C1 side.

The arms 12 and 13 of the clip 10 maintain the closed state. Since the coupling member 63 is disposed within the sheath part 61, the engagement between the hook part 77 and the central part 14 is maintained.

As illustrated in FIG. 13, in the ride-over state, a distance between a position P3 and a position P4 of the edge part 32a becomes equal to the length L1 of the above-mentioned first locked parts 16 and 17.

(Re-Gripping)

In addition, the clip 10 is elastically deformed. For this reason, in a case where the slider 102 is pushed in in a case where the clip 10 is not in the locked state, the compressed helical spring 36 is extended. The clip body 11 moves to the distal side with respect to the retaining pipe 31 in a state where the retaining pipe 31 has abutted against the distal end support surface 67b, and the clip 10 returns to the initial state illustrated in FIG. 11. By operating the endoscope 114, such as by bending the bending part 128, the clip 10 is made to face another treatment parts T again. By performing the aforementioned procedure after this, the treatment part T can be re-grabbed by the clip 10.

(Locked State from Ride-Over State)

In a case where the slider 102 is further pulled back from the ride-over state, the first arm 12 in which the first locked parts 16 and 17 are provided and the second arm 13 in which the second locked parts 21 and 22 are provided are inserted through the locking part 32 in a state where the positions of the first arm 12 and the second arm 13 in the facing direction X and the orthogonal direction Z with respect to the retaining pipe 31 are maintained. Then, the first locked parts 16 and 17 and the second locked parts 21 and 22 move to the proximal side beyond the locking part 32.

Figure 15:
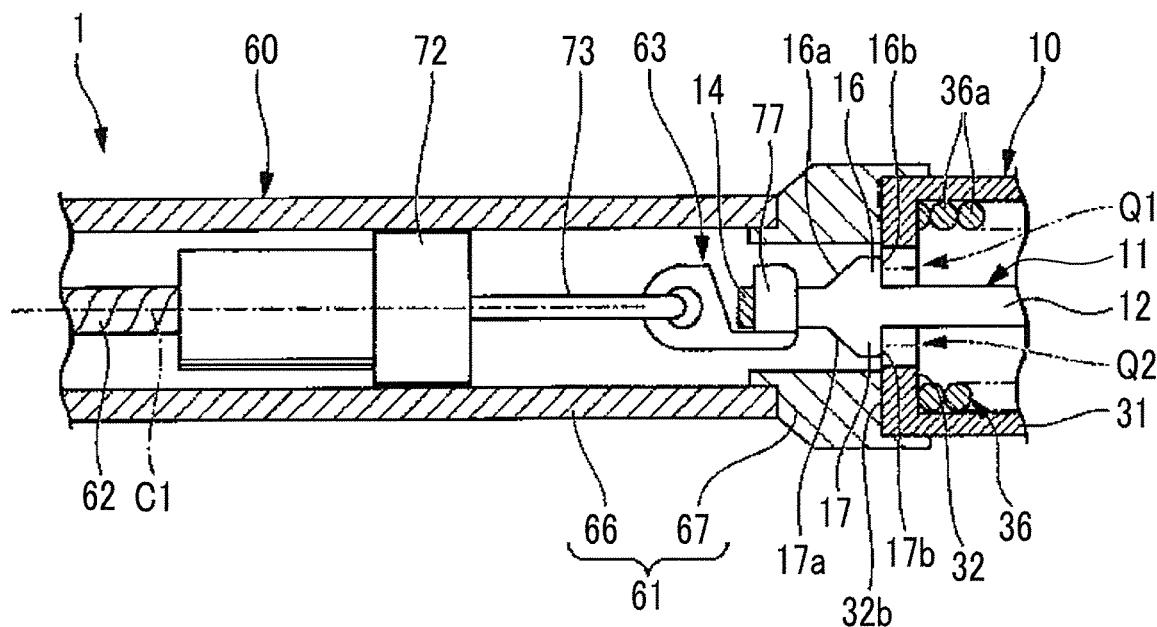
FIG. 15 is a cross-sectional view illustrating the plane of the first treatment tool in a locked state.
Figure 16:
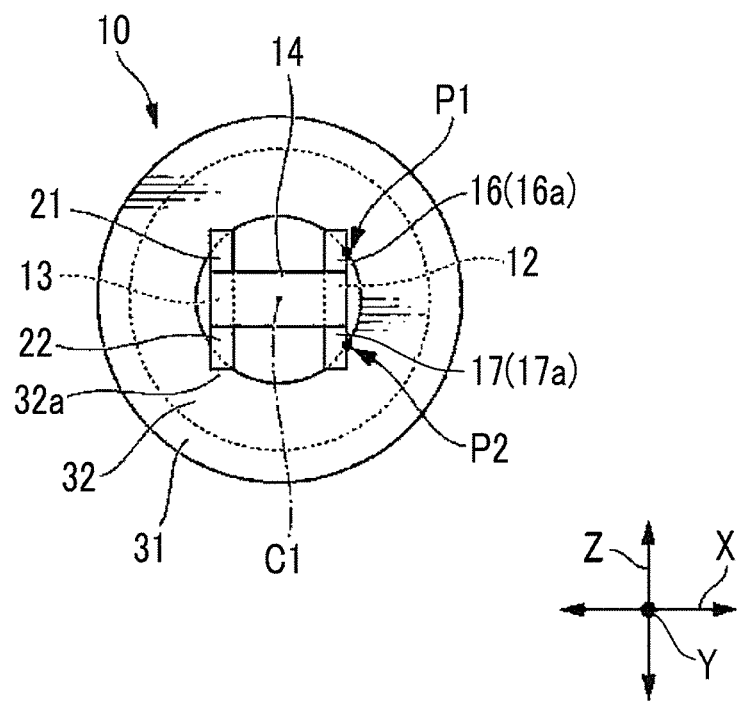
FIG. 16 is a front view of the proximal end surface of the clip in the locked state.

In this case, the arms 12 and 13 and the central part 14 do not receive the biasing from the locking part 32. For this reason, as illustrated in FIGS. 15 and 16, the elastic force of the central part 14 causes a proximal side of the first arm 12 and a proximal side of the second arm 13 to move in the facing direction X so as to be separated apart from each other. Here, in a case where the force to move the clip body 11 to the proximal side of the retaining pipe 31 is released, the locked state where the distal end surfaces 16b and 17b of the first locked parts 16 and 17 are locked to the distal side of the proximal end surface 32b of the locking part 32 is brought about.

Portion of resilient deformation of the arms 12 and 13 and the central part 14 is released from the ride-over state to the locked state. In the locked state, the closed state of the arms 12 and 13 of the clip 10 is maintained. Since the coupling member 63 is disposed within the sheath part 61, the engagement between the hook part 77 and the central part 14 is maintained.

In a case where the clip 10 is brought into the locked state, as illustrated in FIG. 15, the helical spring 36 compressed in the axial direction Y is brought into a densely wound state in which the bare wires 36a adjacent to each other in the axial direction Y are substantially in close contact with each other. Since the distal end surfaces 16b and 17b of the first locked parts 16 and 17 are locked to the proximal end surface 32*b* of the locking part 32 in a case where the clip 10 are brought into the locked state, the movement of the clip body 11 to the distal side with respect to the retaining pipe 31 is restricted. That is, a state where the clip 10 has ligated the treatment part T is maintained, and a return to the initial state where the arms 12 and 13 are brought into the open state is not performed. That is, the arms 12 and 13 of the clip 10 are locked to the closed state. The central part 14 protrudes further toward the proximal side than the retaining pipe 31.

Since the helical spring 36 is in the densely wound state, even in a case where the slider 102 is further pulled back, the clip body 11 cannot move to the proximal side with respect to the retaining pipe 31. The locked state of the clip 10 is maintained and does not change. The closed state of the arms 12 and 13 of a clip 10 is maintained. Since the coupling member 63 is disposed within the sheath part 61, the engagement between the hook part 77 and the central part 14 is maintained.

(Separation of Clip 10)

After this, the clip 10 is separated from the treatment tool body 40.

Figure 17:
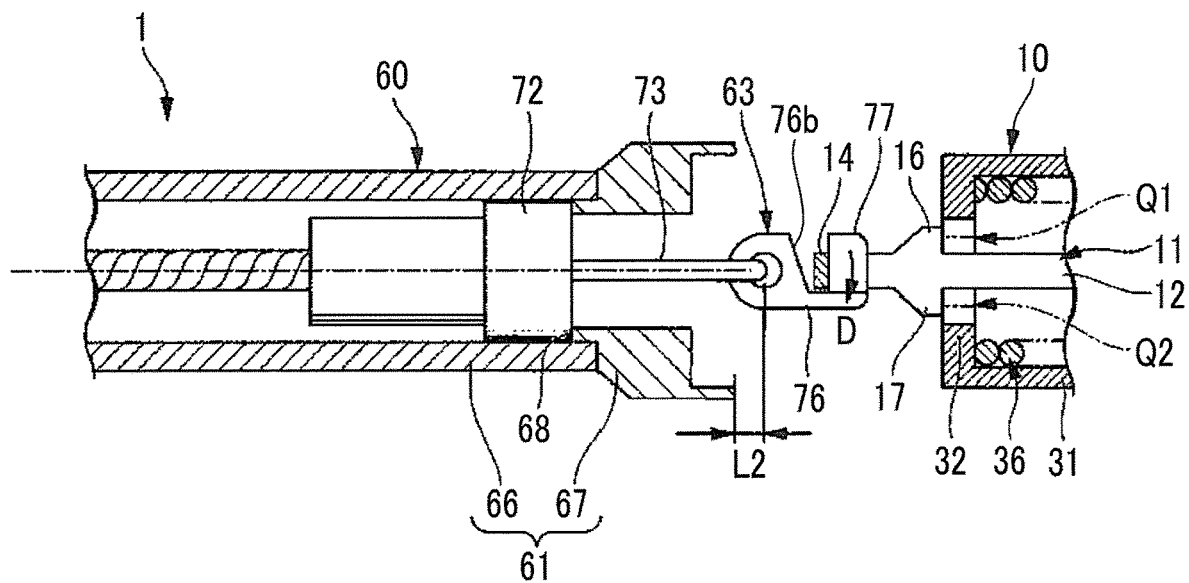
FIG. 17 is a cross-sectional view illustrating the plane of the first treatment tool in a state where the clip is protruded from a treatment tool body.

A procedure of separating the clip 10 from the treatment tool body 40 is as follows. In a case where the slider 102 is pushed in, the operating wire 62 moves to the distal side with respect to the coiled sheath 66. As illustrated in FIG. 17, a distal end surface of the diameter-enlarged part 72 abuts against the stepped part 68, and the loop part 73 protrudes up to a length L2 that is the maximum amount of protrusion with respect to the distal end member 67.

Figure 18:
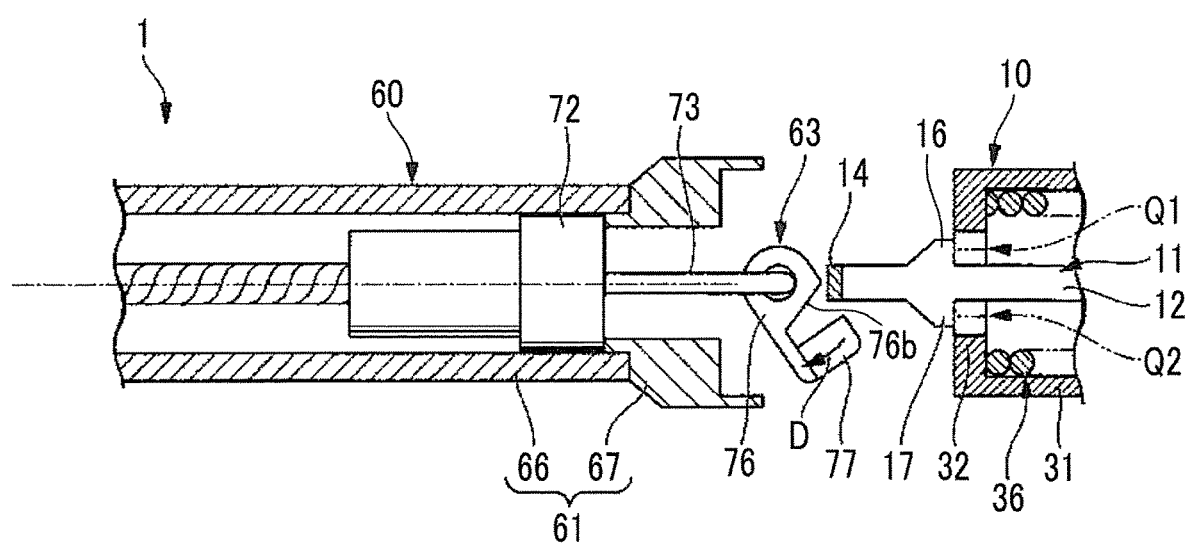
FIG. 18 is a cross-sectional view illustrating the plane of the first treatment tool in a state where the clip is separated from the treatment tool body.

In a case where the coupling member 63 protrudes further toward the distal side than the distal end member 67, the clip body 11 and the retaining pipe 31 integrally moves to the distal side. Since the coupling member 63 is located outside the retaining pipe 31, the coupling member 63 cannot be rotationally moved with respect to the loop part 73. In a case where the slider 102 is pushed in and the operating wire 62 is moved to the distal side, the inclined surface 76*b* of the coupling member 63 comes into contact with a proximal end surface of the central part 14 of the clip 10 that has ligated the treatment part T. As illustrated in FIG. 18, the hook part 77 is rotationally moved in the direction D together with the coupling part body 76 while being guided by the inclined surface 76*b*, and the engagement between the hook part 77 and the central part 14 is released. Accordingly, as illustrated in FIG. 19, the clip 10 in which the arms 12 and 13 are locked to the closed state is separated from the sheath part 61 and indwelled in the treatment part T.

That is, the closed state of the arms 12 and 13 of the clip 10 is maintained in a state where the slider 102 is pushed in and the coupling member 63 is protruded further to the distal side than the distal end member 67 as illustrated in FIG. 17. It is possible to release the engagement between the hook part 77 and the central part 14.

(Take-Out of First Treatment Tool 1)

As illustrated in FIG. 19, the slider 102 is pulled back, the coupling member 63 is housed within the sheath part 61, and the first treatment tool 1 is pulled out and taken out from the treatment tool insertion port 136 of the endoscope 114. In addition, in tying up a plurality of treatment parts, the above-mentioned operation is repeated and it performs it.

Finally, the insertion part 124 of the endoscope 114 is taken out from the inside of the patient's body.

Next, the operation in a case where the clip 10 indwelled within the patient's body is taken out after hemostasis of a ligation point is sufficiently completed will be described.

(Operation of Endoscope 114)

Figure 20:
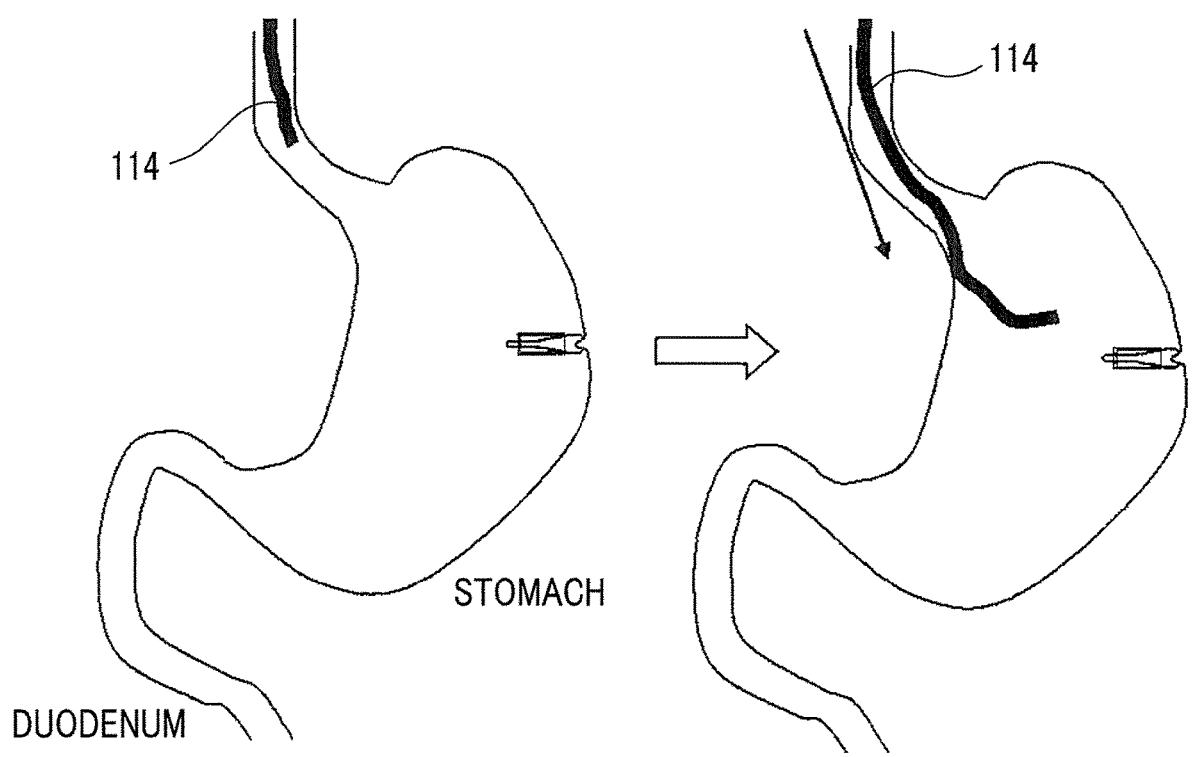
FIG. 20 is a conceptual diagram view of one embodiment illustrating an aspect in which the distal end of the insertion part of the endoscope is brought close to the clip in the treatment part.

The operation of the endoscope 114 is the same as that in a case where the treatment part T is ligated. For example, as illustrated in FIG. 20, the distal end 130 of the insertion part 124 is moved forward to the vicinity of the clip 10 that is in the treatment part T of the stomach side wall through the esophagus.

(Operation of Second Treatment Tool 2)

Next, the operation of the second treatment tool 2 (gripping forceps) illustrated in FIG. 6 will be described.

At the time of use of the second treatment tool, the insertion part 81 of the second treatment tool is inserted from the treatment tool insertion port 136 of the endoscope 114 inserted into the patient's body, and the distal end of the insertion part 81 is protruded from the treatment tool delivery port 144 of the endoscope 114 as illustrated in FIG. 21. Subsequently, the slider 87 is moved to the distal side with respect to the operating part body 86. Accordingly, the operating wire 85 is moved to the distal side, and the pair of claw members 83*a* and 83*b* is brought into the open state.

Subsequently, the claw members 83*a* and 83*b* are made to face to the clip 10, for example, by bending the bending part 128 provided in the insertion part 124 of the endoscope 114 while observing the inside of the patient's body by the endoscope 114. In addition, the orientation of the claw members 83*a* and 83*b* can be adjusted by rotating the operating wire 85 with respect to the sheath 84. By pushing in the second treatment tool 2 with respect to the endoscope 114, the gripping surfaces of the pair of claw members 83*a* and 83*b* are brought into contact with the first locked parts 16 and 17 and the second locked parts 21 and 22 of the clip 10 in the facing direction X.

Subsequently, in a case where the slider 87 is moved to the proximal side with respect to the operating part body 86, the operating wire 85 is moved to the proximal side, and the pair of claw members 83*a* and 83*b* is brought into the closed state. Accordingly, the first locked parts 16 and 17 and the second locked parts 21 and 22 are gripped by the gripping surfaces of the pair of claw members 83*a* and 83*b* in the facing direction X. In addition, the gripping force resulting from the pair of claw members 83*a* and 83*b* can be increased by increased the movement distance of the slider 87 with respect to the operating part body 86.

As illustrated in FIG. 16, in the locked state of the clip 10, the proximal side of the first arm 12 and the proximal side of the second arm 13 are biased by the elastic force of the central part 14 in the facing direction X in which the arms are spaced apart from each other. In a case where the slider 87 continues moving to the proximal side, the first locked parts 16 and 17 and the second locked parts 21 and 22 are pressed from both sides in the facing direction X depending on the gripping force resulting from the pair of claw members 83*a* and 83*b*, and move in a direction in which the locked parts approach each other in the facing direction X as indicated by an arrow in FIG. 22.

As illustrated in FIG. 15, in the locked state, the clip body 11 is biased to the distal side by the compressed helical spring 36. As illustrated in FIG. 13, in a case where the first locked parts 16 and 17 and the second locked parts 21 and 22 move to a position where the distance between the position P3 and the position P4 of the edge part 32*a* of the locking part 32 becomes equal to the length L1 of the first locked parts 16 and 17, the first locked parts 16 and 17 and the second locked parts 21 and 22 move to the distal side beyond the locking part 32.

In this case, the clip body 11 is relatively moved to the distal side with respect to the retaining pipe 31 by the biasing force of the helical spring 36, and as illustrated in FIG. 23, the first arm 12 and the second arm 13 are brought into the open state. Accordingly, the clip 10 is disengaged from the treatment part T. That is, the locking of the arms 12 and 13 of the clip indwelled in the treatment part T and locked to the closed state is released, and as the locking is released, the arms 12 and 13 of the clip 10 are brought into the open state and are removed from the treatment part T.

Thereafter, the endoscope 114 is pulled out and taken out from the inside of the patient's body in a state where the clip 10 is maintained by the pair of claw members 83a and 83b and the second treatment tool 2 is inserted inside the endoscope 114. In addition, in a case where the clip 10 ligated to a plurality of treatment parts is taken out, the aforementioned operation is repeatedly performed.

(Operation of Second Treatment Tool 3)

Next, the operation of the second treatment tool (snare-like member) 3 illustrated in FIG. 7 will be described.

At the time of use of the second treatment tool, the insertion part 91 of the second treatment tool is inserted from the treatment tool insertion port 136 of the endoscope 114 inserted into the patient's body, and the distal end of the insertion part 91 is protruded from the treatment tool delivery port 144 of the endoscope 114. Subsequently, the slider 97 is moved to the distal side with respect to the operating part body 96. As a result, the operating wire 95 is moved to the distal side, the loop part 90 is protruded from the distal end of the sheath 94, the diameter of the loop of the loop part 90 is widened and becomes larger.

Subsequently, the loop part 90 is made to face to the clip 10, for example, by bending the bending part 128 provided in the insertion part 124 of the endoscope 114 while observing the inside of the patient's body by the endoscope 114. In addition, the orientation of the loop part 90 can be adjusted by rotating the operating wire 95 with respect to the sheath 94. By pushing in the second treatment tool 3 with respect to the endoscope 114, the first locked parts 16 and 17 and the second locked parts 21 and 22 of the clip 10 are housed within the loop of the loop part 90.

Subsequently, in a case where the slider 97 is moved to the proximal side with respect to the operating part body 96, the operating wire 95 is moved to the proximal side, and the diameter of the loop of the loop part 90 is reduced and becomes smaller. Accordingly, the first locked parts 16 and 17 and the second locked parts 21 and 22 are surrounded by the loop of the loop part 90 in the facing direction X. In addition, by increasing the movement distance of the slider 97 with respect to the operating part body 96, the diameter of the loop of the loop part 90 can be reduced and made still smaller.

In a case where the slider 97 continues moving to the proximal side, the first locked parts 16 and 17 and the second locked parts 21 and 22 are clamped by the loop of the loop part 90, are pressed from both sides in the facing direction X depending on the clamping force, and move in the direction in which the locked parts approach each other in the facing direction X.

The operation of the second treatment tool (snare-like member) 3 after this is the same as that in the case of the second treatment tool (gripping forceps) 2.

In the clip treatment tool, the treatment part T can be re-grabbed by the clip 10 until the clip 10 is ligated to the treatment part T, and a state where the arms 12 and 13 of the clip 10 are locked to the closed state and the clip 10 is ligated to the treatment part can be reliably maintained, once the clip is ligated to the treatment part T. Additionally, after the clip 10 is indwelled in the treatment part T within the living body, the locking of the arms 12 and 13 of the indwelled clip 10 can be released at any timing, and the clip 10 can be removed.

In addition, in the above embodiment, after the ligation of the treatment part T, the insertion part 124 of the endoscope 114 is once taken out from the inside of the patient's body. However, the invention is not limited to this.

For example, in a case where the position of the ligation by the clip 10 is shifted from a position to be ligated due to an operation error or the like, not only the clip 10 ligated to a shifted position is unnecessary but also there is a hindrance even in a case where the next clip is ligated to the position to be ligated in a case where the clip 10 is left behind immediately adjacent to the position to be ligated.

In this case, the clip 10 may be taken out by pulling out the first treatment tool 1 from the treatment tool insertion port 136 of the endoscope 114, pulling out the second treatment tool 2 or 3 without pulling out the insertion part 124 of the endoscope 114, and releasing the locking of the arms 12 and 13 of the clip 10 ligated to the shifted position.

As in the above embodiment, the first treatment tool 1 and the second treatment tools 2 and 3 may be separately configured, or the first treatment tool 1 and the second treatment tools 2 and 3 may be integrally configured.

In this case, one operating part can be used by making the operating part 100 of the first treatment tool 1 and the operating parts 82 and 92 of the second treatment tools 2 and 3 common. Additionally, in a case where the clip 10 ligated to the shifted position is taken out as described above and in a case where the first treatment tool 1 and the second treatment tools 2 and 3 are separate, it is necessary to replace the first treatment tool and the second treatment tools 2 and 3. However, in a case where the treatment tools are integral, there is a merit that it is not necessary to replace the treatment tools.

The clip of the clip treatment tool of the invention is not limited to the one described above. As illustrated in FIGS. 24 to 28, in a case where the clip removal part of the invention releases the locking of the clip body to the retaining pipe and the spring member is extended to relatively move the clip body to the distal side of the retaining pipe, a movement regulating part of the structure in which jump-out of the clip body is prevented from the retaining pipe to the distal side may be provided.

Figure 24:
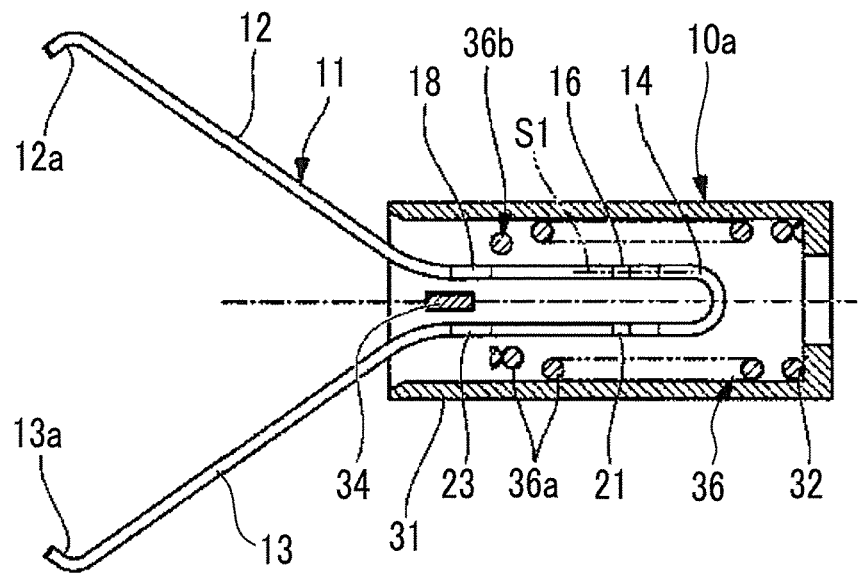
FIG. 24 is a cross-sectional view illustrating a side surface of another embodiment of the clip of the clip treatment tool related to the invention.
Figure 25:
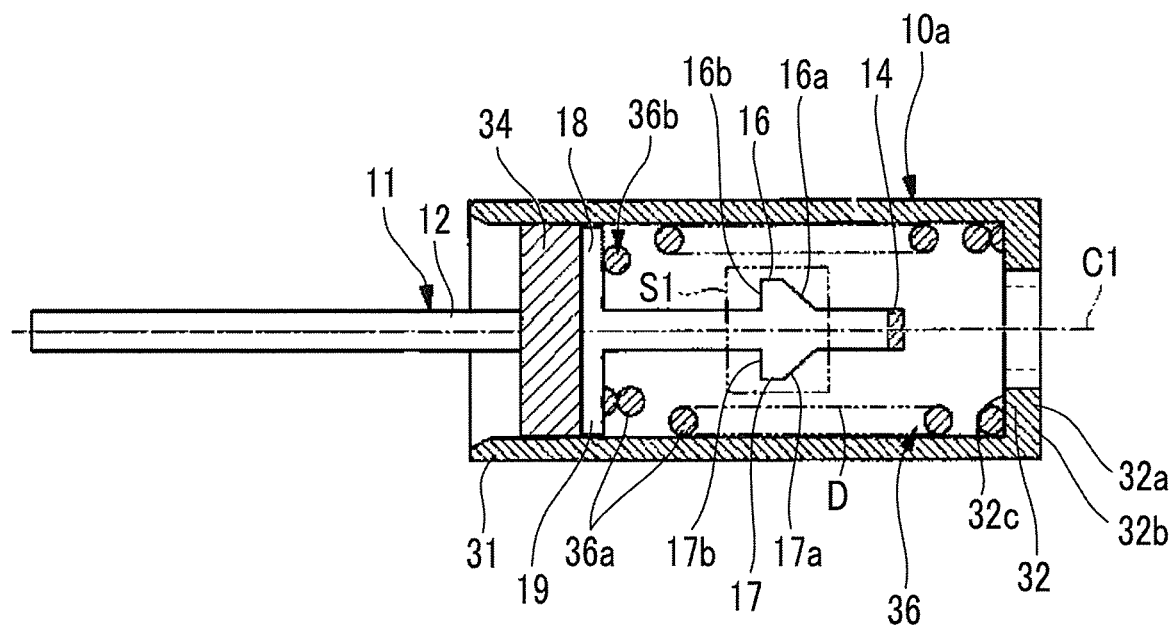
FIG. 25 is a cross-sectional view illustrating a plane of the clip illustrated in FIG. 24.

A clip 10a illustrated in FIGS. 24 and 25 comprises the clip body 11, the retaining pipe 31, the helical spring 36, and a pin-shaped member 34 that is the movement regulating part of the invention.

Since the clip 10a has the same configuration as the clip 10 illustrated in FIGS. 3 and 4 except for the pin-shaped member 34, the same constituent elements will be designated by the same numbers, and the detailed description thereof will be omitted.

The pin-shaped member 34 prevent jump-out of the clip body 11 to the front by the helical spring 36 that is a spring member of the invention in a case where the locking of the clip body 11 by the locking part 32 in the retaining pipe 31 is released by the second treatment tool 2 or 3 that constitutes the clip removal part of the invention, in the clip 10 illustrated in FIGS. 3 and 4.

The pin-shaped member 34 is a member that is inserted between the arms 12 and 13 of the clip body 11 and extends in the direction orthogonal (perpendicular) to an opening/closing direction of the two arms 12 and 13. Both ends of the pin-shaped member 34 are fixed to an inner peripheral part of the retaining pipe 31. The pin-shaped member 34 is in an initial state illustrated in FIGS. 24 and 25, and is provided at a position slightly closer to the distal side than the protrusions 18 and 19 of the first arm 12 and the protrusions 23 and 24 of the second arm 13 in the clip body 11 within the retaining pipe 31, in a case where the arms 12 and 13 of the clip body 11 are in the open state.

In the clip 10a of the present embodiment, by having the pin-shaped member 34 within the retaining pipe 31, the locking of the clip body 11 by the locking part 32 of the retaining pipe 31 is released, and the clip body 11 moves to the distal side of the retaining pipe 31. As a result, in a case where the locking between a seat winding 36b of the helical spring 36 and the protrusions 18 and 19 of the first arm 12 and the protrusions 23 and 24 of the second arm 13 in the clip body 11 is released, and the clip body 11 tries to jump out from the retaining pipe 31 to the distal side, the pin-shaped member 34, and the central part 14 that is a connecting part between the first arm 12 and the second arm 13 abut against each other. In this way, the clip body 11 restricts the jump-out of the distal end of the retaining pipe 31.

Figure 26:
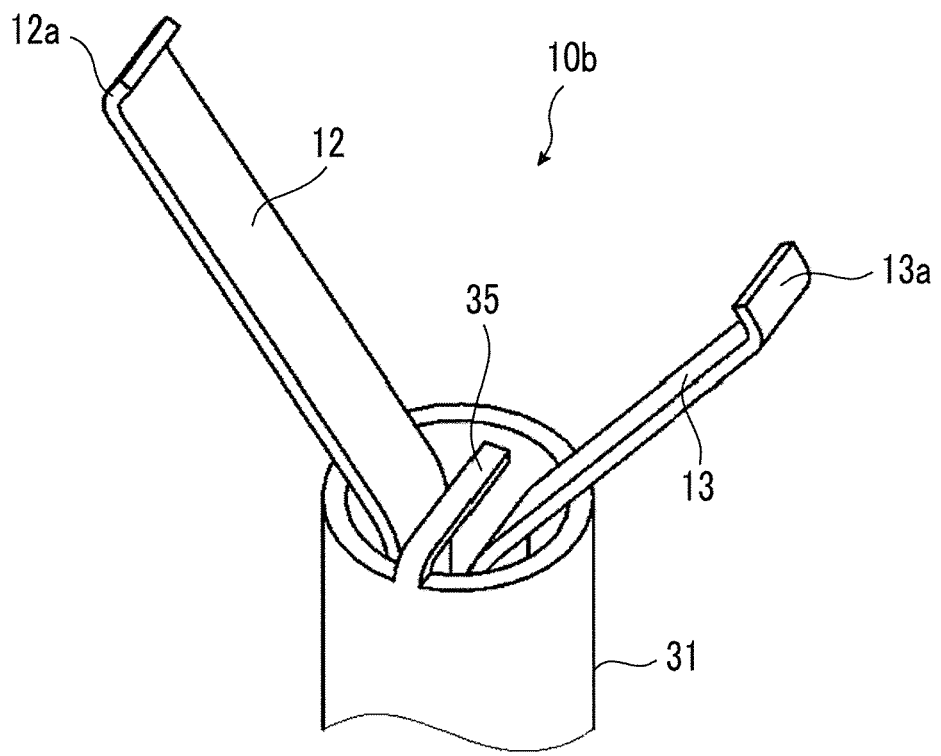
FIG. 26 is a fragmentary perspective view illustrating still another embodiment of the clip of the clip treatment tool related to the invention.

Additionally, as in a clip 10b illustrated in FIG. 26, instead of the pin-shaped member 34 of the clip 10a illustrated in FIGS. 24 and 25, one having a cantilever beam member 35 may be provided as the movement regulating part of the invention.

The clip 10b comprises the clip body 11, the retaining pipe 31, the helical spring 36, and the cantilever beam member 35 that is the movement regulating part of the invention.

Since the clip 10b has the same configuration as the clip 10a illustrated in FIGS. 24 and 25 except that the cantilever beam member 35 is provided instead of the pin-shaped member 34, the same constituent elements will be designated by the same numbers, and the detailed description thereof will be omitted.

The cantilever beam member 35 has one end fixed to the distal end of the retaining pipe 31. The cantilever beam member 35 is a member that is inserted between the arms 12 and 13 of the clip body 11 and extends in the direction orthogonal (perpendicular) to the opening/closing direction of the two arms 12 and 13, similarly to the pin-shaped member 34 illustrated in FIGS. 24 and 25.

Additionally, the cantilever beam member 35 illustrated in FIG. 26 abuts against the central part 14, which is the connecting part between the first arm 12 and the second arm 13, to restrict the jump-out of the clip body 11 from the distal end of the retaining pipe 31, in a case where the locking of the clip body 11 by the locking part 32 of the retaining pipe 31 is released and the clip body 11 tries to jump out from the retaining pipe 31 to the distal side, similarly to the pin-shaped member 34 of the clip 10a illustrated in FIGS. 24 and 25.

In addition, in the example illustrated in FIGS. 24 and 25, the pin-shaped member 34 of which both ends are fixed to an inner peripheral surface of the retaining pipe 31 is used as the movement regulating part. However, the invention is not limited to this. A pin-shaped member of which both ends are fixed to the distal end of the retaining pipe 31 may be used.

Additionally, in the example illustrated in FIG. 26, the cantilever beam member 35 of which one end is fixed to the distal end of the retaining pipe 31 is used as the movement regulating part. However, the invention is not limited to this. A cantilever beam member of which one end is fixed to the inner peripheral surface of the retaining pipe 31 may be used.

Additionally, in the invention, a pin-shaped member in which an intermediate part is cut, or two cantilever beam members in which distal ends face each other may be used instead of such a pin-shaped member and such a cantilever beam member.

Additionally, in the invention, in a case where the clip body has two or more arms, a pin-shaped member, which is inserted between at least two arms of the two or more arms, extends in a direction orthogonal to an opening/closing direction of the at least two arms of the two or more arms, and has both ends fixed to the inner peripheral surface or the distal end of the retaining pipe, or a cantilever beam member of which one end is fixed to the distal end or the inner peripheral surface of the retaining pipe may be used as the movement regulating part.

Figure 27:
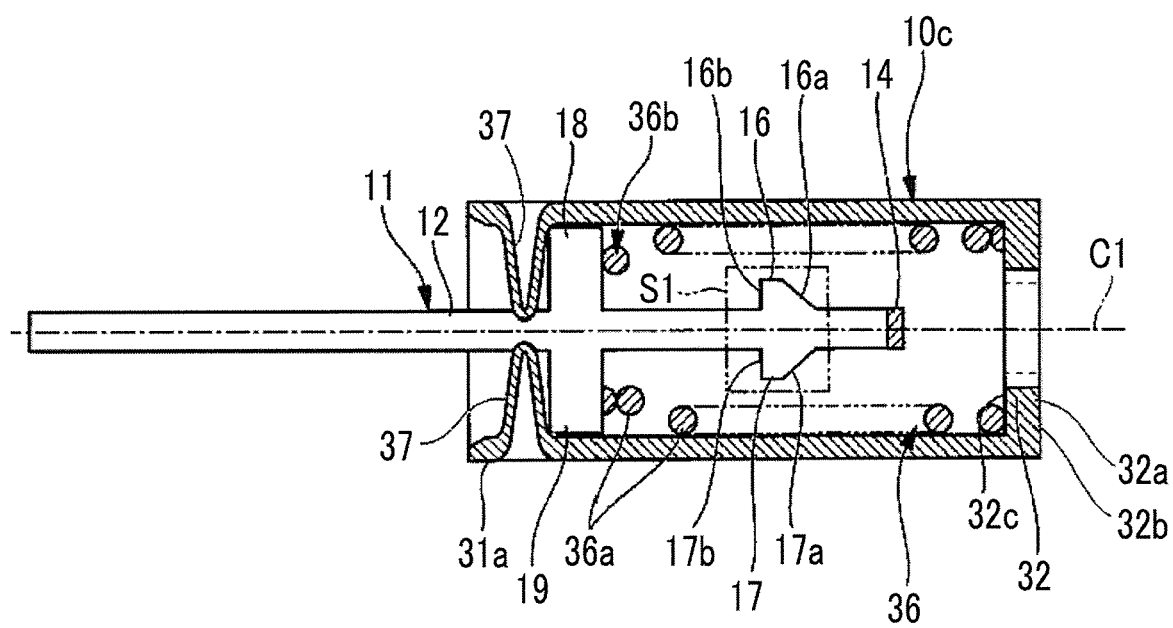
FIG. 27 is a cross-sectional view illustrating a plane of a still further embodiment of the clip of the clip treatment tool related to the invention.

Additionally, as in the clip 10c illustrated in FIG. 27, the protrusion 37 resulting from deep drawing or the like may be provided on the distal side of the retaining pipe 31a as the movement regulating part of the invention.

The clip 10c comprises the clip body 11, the retaining pipe 31, the helical spring 36, and the protrusion 37 that is the movement regulating part of the invention.

Since the clip 10c has the same configuration as the clip 10b illustrated in FIG. 6 except that the protrusion 37 is provided instead of the cantilever beam member 35, the same constituent elements will be designated by the same numbers, and the detailed description thereof will be omitted.

The protrusion 37 is formed at the distal end of the retaining pipe 31, and similarly to the pin-shaped member 34 illustrated in FIGS. 24 and 25, is inserted between the arms 12 and 13 of the clip body 11 and protrudes in the direction orthogonal (perpendicular) to the opening/closing direction of the two arms 12 and 13.

The protrusion 37 illustrated in FIG. 27 abuts against the central part 14, which is the connecting part of the first arm 12 and the second arm 13, to restrict the jump-out of the clip body 11 from the distal end of the retaining pipe 31, in a case where the clip body 11 tries to jump out from the retaining pipe 31 to the distal side similarly to the pin-shaped member 34.

Figure 28:
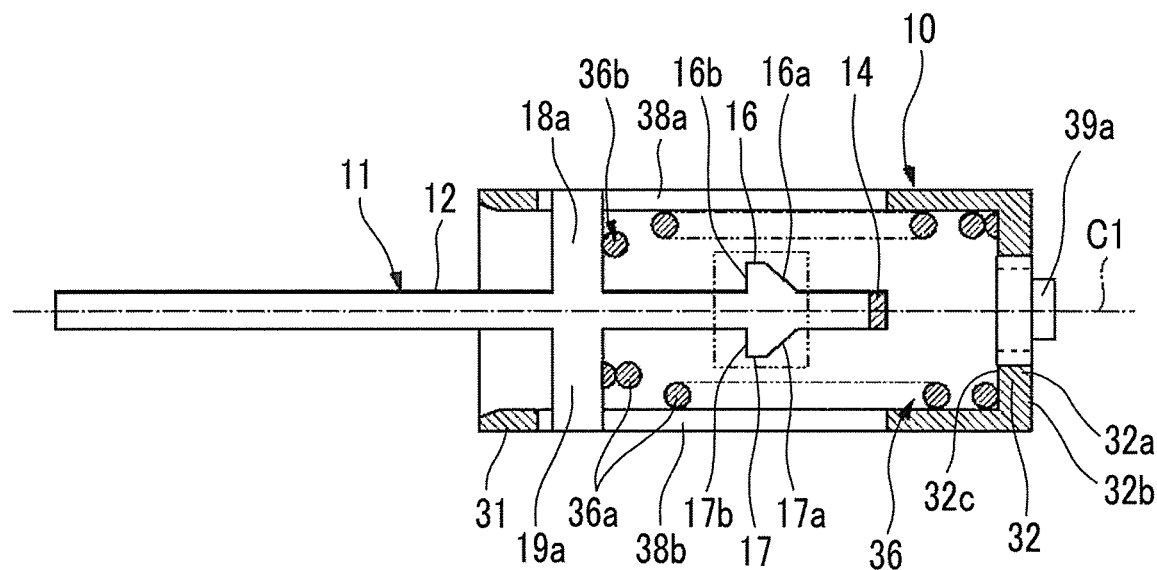
FIG. 28 is a cross-sectional view illustrating a plane of a still further embodiment of the clip of the clip treatment tool related to the invention.
Figure 29:
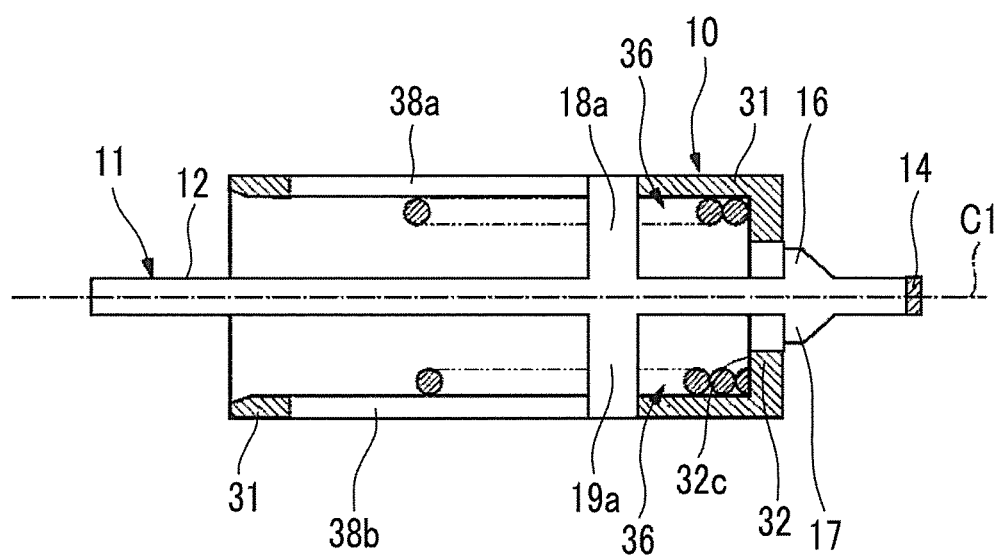
FIG. 29 is a cross-sectional view illustrating a plane of another form of the clip illustrated in FIG. 28.
Figure 30:
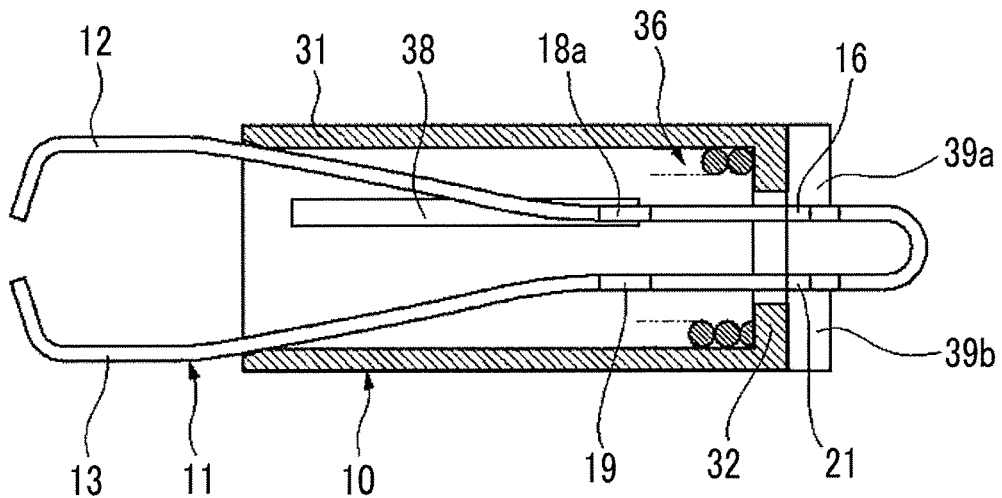
FIG. 30 is a cross-sectional view illustrating a side surface of the clip illustrated in FIG. 29.

Additionally, as in a clip 10d illustrated in FIGS. 28, 29, and 30, protrusions 18a and 19a provided in the first arm 12 and slits 38a and 38b to be respectively engaged with the protrusions 18a and 19a may be used as the movement regulating part of the invention.

The clip 10d comprises the clip body 11, the retaining pipe 31, the helical spring 36, and the protrusions 18a and 19a and the slits 38a and 38b that are the movement regulating parts of the invention, and pressed parts 39a and 39b.

Since the clip 10d has the same configuration as the clip 10a illustrated in FIGS. 24 and 25 except that the protrusions 18a and 19a, the slits 38a and 38b, and pressed parts 39 are provided instead of the pin-shaped member 34, the same constituent elements will be designated by the same numbers, and the detailed description thereof will be omitted.

The protrusions 18a and 19a protrude on both sides from the first arm 12 toward a peripheral wall surface of the retaining pipe 31. In addition, the protrusions 18a and 19a may be formed by extending distal ends of the protrusions 18 and 19 of the first arm 12 of the clip body 11 of the clip 10a illustrated in FIG. 25.

Additionally, the slits 38a and 38b are formed in the peripheral wall surface of the retaining pipe 31 in correspondence with the protrusions 18a and 19a, respectively, and are engaged with the protrusions 18a and 19a, respectively.

In the example illustrated in FIG. 28, in a case where the locking of the clip body 11 by the locking part 32 of the retaining pipe 31 is released and the clip body 11 tries to jump out from the retaining pipe 31 to the distal side, the protrusions 18a and 19a of the first arm 12 are engaged with the slits 38a and 38b, respectively, and restricts the jump-out of the clip body 11 from the distal end of the retaining pipe 31.

In addition, two protrusions, which protrude on both sides from the second arm 13 toward the peripheral wall surface of the retaining pipe 31, and two slits, which are formed in the peripheral wall surface of the retaining pipe 31 in correspondence with the two protrusions, respectively, and are engaged with the two protrusions, respectively, may be used as the movement regulating part of the invention. Here, the two protrusions may be formed by extending the distal ends of the protrusions 23 and 24 of the second arm 13 of the clip body 11 of the clip 10a illustrated in FIG. 25.

In addition, the pressed parts 39a and 39b illustrated in FIGS. 28 and 30 are provided outside the locking part 32 on the proximal side of the retaining pipe 31 so as to face each other, and are pressed from both sides and moved or deformed inward toward each other to thereby press the first arm 12 and the second arm 13 of the clip body 11 inward toward each other and release the locked state of the clip body 11 illustrated in FIGS. 29 and 30.

The pressed parts 39a and 39b are provided to face each other on both sides of the protruding parts in a pressing direction in which the first locked parts 16 and 17 of the first arm 12 and the second locked parts 21 and 22 of the second arm 13 that are the protruding parts of the invention are pressed against the proximal end surface 32b of the locking part 32 of the retaining pipe 31, and are both moved or deformed themselves inward by the second treatment tool (not illustrated) to press the portion of the first arm 12 between the first locked parts 16 and 17 of the clip body 11 and the portion of the second arm 13 between the second locked parts 21 and 22 inward toward each other to reduce the external diameter of the protruding parts, which is the diameter of the circumscribed circle of the first locked parts 16 and 17 and the second locked parts 21 and 22, to be smaller than the internal diameter of the opening part 32a of the locking part 32. As a result, the first locked parts 16 and 17 and the second locked parts 21 and 22 pass through the opening part 32a, and release the locking of the clip body 11 by the locking part 32 of the retaining pipe 31.

Figure 31:
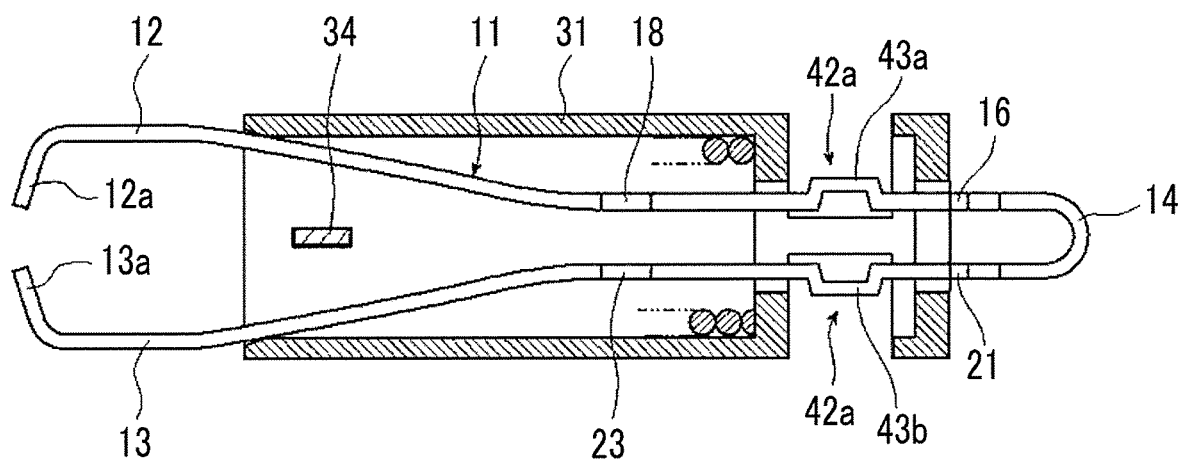
FIG. 31 is a cross-sectional view illustrating a side surface of a still further embodiment of the clip of the clip treatment tool related to the invention.
Figure 32:
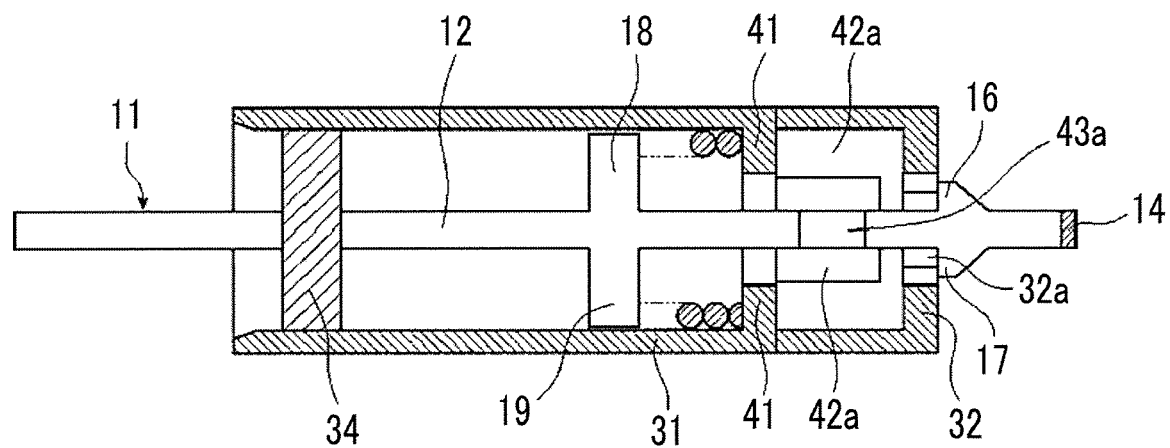
FIG. 32 is a cross-sectional view illustrating a plane of the clip illustrated in FIG. 31.

Additionally, in order to release the locking of the clip body 11 by the locking part 32 of the retaining pipe 31 as in the clip 10e illustrated in FIGS. 31 and 32, the opening parts 42a and 42b that allow the pressing by the second treatment tool (not illustrated) may be provided on the proximal side of the retaining pipe 31.

The clip 10e comprises the clip body 11, the retaining pipe 31, the helical spring 36, the pin-shaped member 34, the opening parts 42a and 42b provided on the proximal side of the retaining pipe 31, and protrusions 43a and 43b provided on the proximal side of the clip body 11.

Since the clip 10e has the same configuration as the clip 10a illustrated in FIGS. 24 and 25 except that the clip 10e comprises the opening parts 42a and 42b and the protrusions 43a and 43b, the same constituent elements will be designated by the same numbers, and the detailed description thereof will be omitted.

Here, the opening parts 42a and 42b are peripheral wall surfaces on the proximal side of the retaining pipe 31, and are provided on the distal side of the locking part 32 so as to face each other. In a case where the two arms 12 and 13 are locked to the closed state, the opening parts 42a and 42b are for exposing a portion of each of the two arms 12 and 13, and are located on the proximal sides of the peripheral wall surfaces that face the two arms 12 and 13, respectively. The locked state of the clip body 11 by the locking part 32 of the retaining pipe 31 is released by pressing the two arms 12 and 13 of the clip body 11 exposed from the two opening parts 42a and 42b of the side surfaces of the retaining pipe 31 inward toward each other by the second treatment tool (not illustrated).

Specifically the opening parts 42a and 42b of the side surfaces of the retaining pipe 31 exposes portions between the first locked parts 16 and 17 and the protrusions 18 and 19 in the first arm 12 of the clip body 11 and between the second locked parts 21 and 22 and the protrusions 23 and 24 in the second arm 13, in the locked state (the closed state between the first arm 12 and the second arm 13 of the clip body 11) of the clip body 11 by the locking part 32 of the retaining pipe 31. The external diameter of the protruding parts that is the diameter of the circumscribed circle of the first locked parts 16 and 17 and the second locked parts 21 and 22 is reduced to be smaller than the internal diameter of the opening part 32a of the locking part 32 by pressing exposed portions of the first arm 12 and the second arm 13 inward toward each other from the opening parts 42a and 42b by the second treatment tool (not illustrated). As a result, the first locked parts 16 and 17 and the second locked parts 21 and 22 can pass through the opening part 32a, and release the locking of the clip body 11 by the locking part 32 of the retaining pipe 31.

Additionally, the protrusions 43a and 43b are provided so as to face each other from the central axis of the retaining pipe 31 and protrude toward the outer opening parts 42a and 42b between the first locked parts 16 and 17 and the protrusions 18 and 19 in the first arm 12 of the clip body 11 and between the second locked parts 21 and 22 and the protrusions 23 and 24 in the second arm 13, in the locked state (the closed state of the first arm 12 and the second arm 13 in the clip body 11) of the clip body 11 by the locking part 32 of the retaining pipe 31.

In a case where the first arm 12 and the second arm 13 of the clip body 11 have the protrusions 43a and 43b as described above, the arms can be efficiently pressed by the second treatment tool (not illustrated).

In addition, in the clip 10e, the retaining pipe 31 has a circular protrusion 41 on an inner peripheral surface on the distal side adjacent to the opening parts 42a and 42b. The protrusion 41 locks a proximal end of the helical spring 36.

In the above-described embodiments, the two arms 12 and 13 of the clip body 11 are integrally connected by the central part 14. However, the invention is not limited to this. Two arms of a clip body may be separately configured as in a clip treatment tool illustrated in FIGS. 33 to 35.

Figure 33:
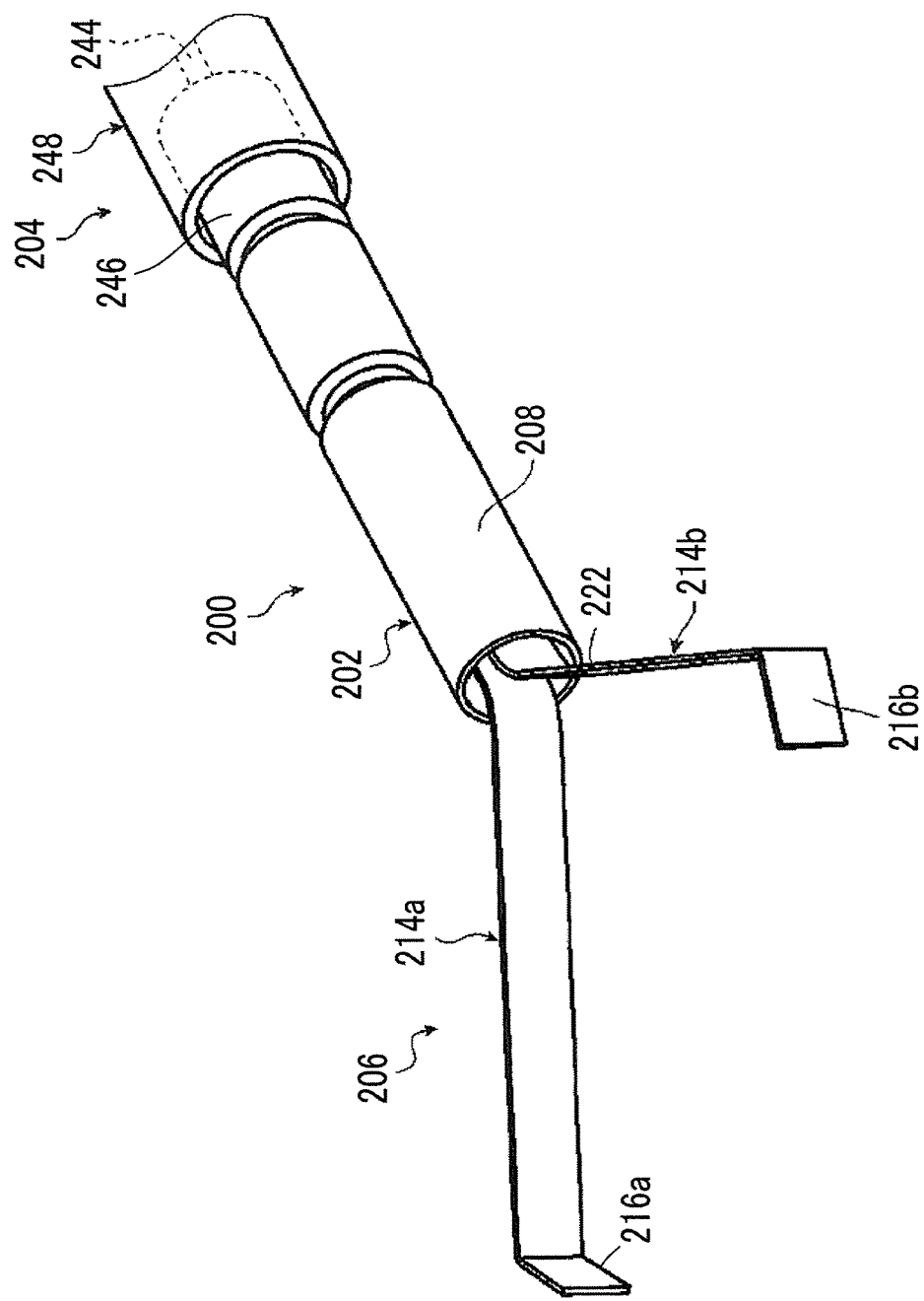
FIG. 33 is a partial transparent perspective view illustrating the appearance of the embodiment of the clip treatment tool of the invention.
Figure 34:
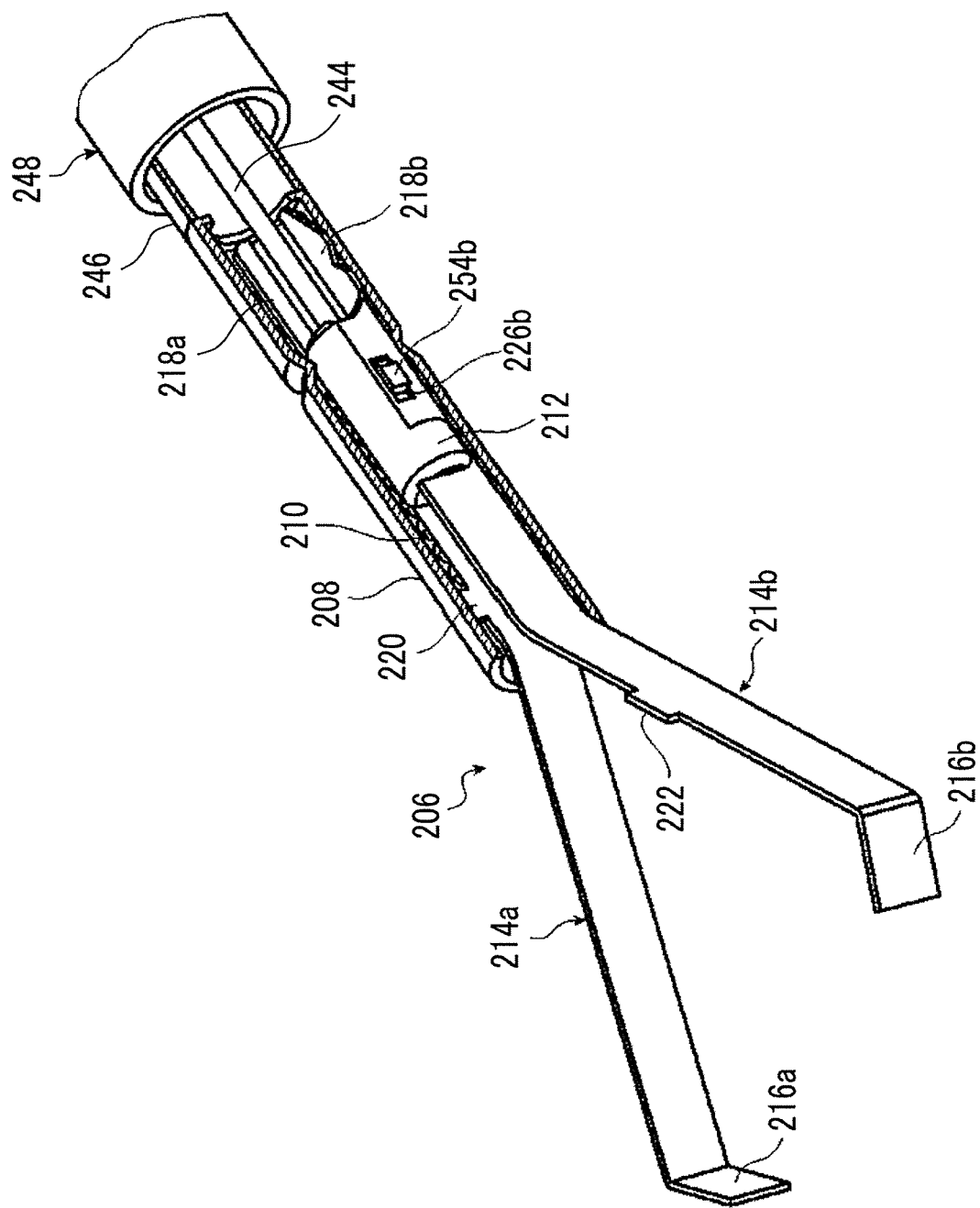
FIG. 34 is a partial cross-sectional perspective view illustrating the configuration of the inside of the clip treatment tool illustrated in FIG. 33.
Figure 35:
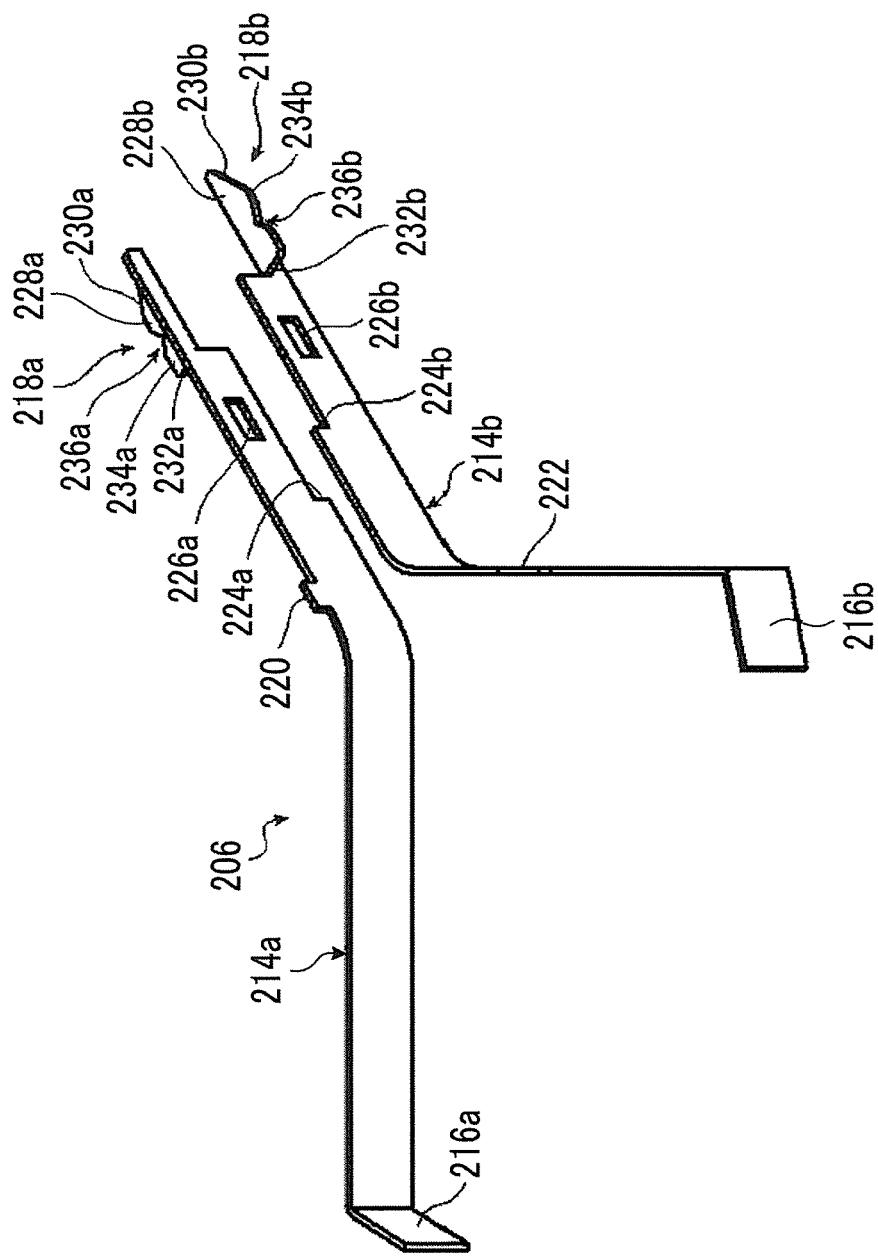
FIG. 35 is a perspective view of a clip body of the clip treatment tool illustrated in FIG. 34.
Figure 36:
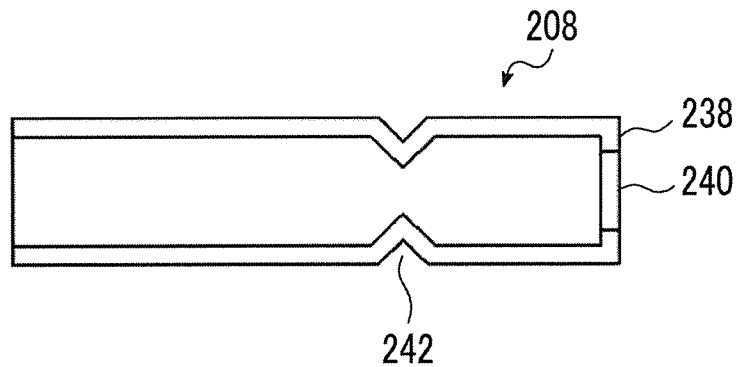
FIG. 36 is a cross-sectional view of a retaining pipe of the clip treatment tool illustrated in FIG. 33.
Figure 37:
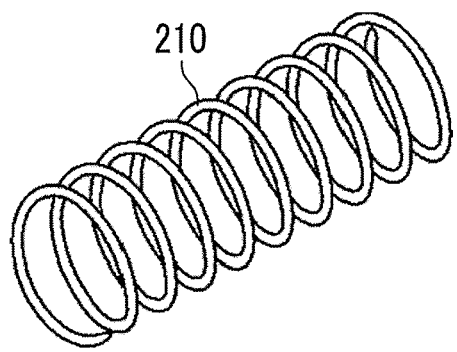
FIG. 37 is a perspective view of a biasing member of the clip treatment tool illustrated in FIG. 34.

FIG. 33 is a partial transparent perspective view illustrating the appearance of another embodiment of the clip treatment tool of the invention. FIG. 34 is a partial cross-sectional perspective view illustrating the configuration of the inside of the clip treatment tool illustrated in FIG. 33. FIG. 35 is a perspective view of a clip body of the clip treatment tool illustrated in FIG. 34. FIG. 36 is a cross-sectional view of a retaining pipe of the clip treatment tool illustrated in FIG. 33. FIG. 37 is a perspective view of a biasing member of the clip treatment tool illustrated in FIG. 34.

The clip treatment tool 200 illustrated in FIGS. 33 and 34 comprises a clip 202 and a treatment tool body 204. For example, as described above, the clip treatment tool 200 is inserted from the treatment tool insertion port provided in the operating part of the endoscope by an operator's operation, and is protruded from the treatment tool delivery port provided in the distal end surface of the insertion part of the endoscope inserted into the patient's body to ligate the treatment part with the clip 202.

The clip 202 comprises a clip body 206, a retaining pipe 208, and a biasing member 210. Also in the present embodiment, the clip 202 is configured as a clip unit in which the clip body 206, the retaining pipe 208, and the biasing member 210 are unitized.

As illustrated in FIG. 35, the clip body 206 has a first arm 214a and a second arm 214b that are separately configured in a plate shape, are disposed to face each other, and extend so as to be spaced apart each other from the proximal side toward the distal side in a state where an external force is not applied.

The distal sides of the first arm 214a and the second arm 214b move in mutually opening and closing directions, and have claws 216a and 216b provided at the distal ends thereof, respectively. The claws 216a and 216b are respectively formed in directions by being bent at a certain angle in directions in which the distal ends of the first arm 214a and the second arm 214b face each other, and are portions that sandwich and ligate a treatment part. Central parts of the first arm 214a and the second arm 214b reciprocate parallel to each other between the proximal side and the distal side. Locking parts 218a and 218b are provided on the proximal sides of the first arm 214a and the second arm 214b.

A protrusion 220 that protrudes upward in the drawing in a plate width direction is provided on a distal side of a central part of the first arm 214a. The protrusion 220 is for locking an end of the biasing member 210 on the distal side. In addition, the same protruding part as the protrusion 220 may also be provided at a central part of the second arm 214b.

On the other hand, a protrusion 222 that protrudes upward in the drawing in the plate width direction is provided on a proximal side of an opening/closing portion of the second arm 214b. The protrusion 222 is for locking the clip body 206 to the retaining pipe 208 in a case where the clip 202 is separated from the treatment tool body 204. In addition, the same protruding part as the protrusion 222 may also be provided on a proximal side of an opening/closing portion of the first arm 214a.

A stepped part 224a of which the plate width becomes narrow from the bottom of the drawing and an oblong hole part 226a in a portion of which the plate width becomes narrow are provided on a proximal side of the central part of the first arm 214a, and a stepped part 224b of which the plate width becomes narrow from the top of the drawing and an oblong hole part 226b in a portion of which the plate width becomes narrow are provided on the proximal side of the central part of the second arm 214b. In addition, it is preferable that the plate widths of the first arm 214a and the second arm 214b are also the same on the proximal side and are also the same on the narrow proximal side. Additionally, in a case where the first arm 214a and the second arm 214b are disposed to face each other, the hole parts 226a and 226b are provided so as to be at the same position.

The locking parts 218a and 218b on the proximal sides of the two arms 214a and 214b of the clip body 206 are constituted of two plate-shaped members 228a and 228b formed by bending portions, in the plate width direction, of respective proximal ends of the two arms 214a and 214b in the direction orthogonal to the opening/closing direction of the two arms 214a and 214b. The two plate-shaped members 228a and 228b respectively comprise inclined parts 230a and 230b that are respectively provided at ends on respective proximal sides of the two arms 214a and 214b, and top parts 234a and 234b that are respectively provided on the distal sides from the inclined parts 230a and 230b and include corners 232a and 232b at ends on the distal sides. Here, the two plate-shaped members 228a and 228b are respectively formed such that the top parts 234a and 234b face each other in the opening/closing direction of the two arms 214a and 214b and are parallel to each other at a distance.

It is preferable that the top parts 234a and 234b respectively have recesses 236a and 236b that are recessed in the opening/closing direction of the two arms 214a and 214b, and are pressed from both outsides in the opening/closing direction of the two arms by the second treatment tool (not illustrated) in a case where the respective recesses 236a and 236b of the two top parts release the locking of the clip body 206 by the locking parts 218a and 218b.

The two arms 214a and 214b having the configuration as described above have the same shape except for the protrusion 220 and the protrusion 222, and are disposed at point-symmetrical positions.

As illustrated in FIG. 36, the retaining pipe 208 is tubular, and has a locked part 238 provided on a proximal side thereof. The locked part 238 is a portion to which the locking parts 218a and 218b of the first and second arms 214a and 214b are locked, and is formed by reducing the diameter of the retaining pipe 208 on the proximal side. In other words, the locked part 238 has a proximal end surface formed on the proximal side of the retaining pipe 208, and a locking hole 240 is formed in the proximal end surface of the retaining pipe 208. The locking hole 240 has an internal diameter smaller than the length between the two facing top parts 234a and 234b of the locking parts 218a and 218b of the first and second arms 214a and 214b.

Additionally, the retaining pipe 208 has a narrowed part 242, having a smaller internal diameter than the internal diameter at both ends, at a central part thereof in the axial direction. The narrowed part 242 is for locking an end of the biasing member 210 on the proximal side.

The retaining pipe 208 functions to open the two arms 214a and 214b to expose the clip body 206 as the clip body 206 moves from the proximal side to the distal side, and to close the two arms 214a and 214b as the clip body 206 moves from the distal side to the proximal side to house the clip body 206 therein.

More specifically, as the clip body 206 moves from the distal side to the proximal side, the two arms 214a and 214b are pressed and elastically deformed by the distal end of the retaining pipe 208 in a direction in which the two arms approach each other, and the two arms 214a and 214b are gradually closed from the open state and are finally brought into the closed state. On the other hand, as the clip body 206 moves from the proximal side to the distal side, the two arms 214a and 214b are gradually opened from the closed state by an elastic force and are finally brought into an open state.

The locking parts 218a and 218b of the two arms 214a and 214b of the clip body 206 and the locked part 238 of the retaining pipe 208 constitute a clip locking part of the invention.

As illustrated in FIG. 34, the biasing member 210 is housed inside the retaining pipe 208. In the case of the present embodiment, as illustrated in FIG. 37, it is preferable that the biasing member 22 is a compression spring including a helical spring or the like.

The biasing member 210 is provided so as to cover outer surfaces of the two arms 214a and 214b, and disposed between the protrusion 220 of the first arm 214a of the clip body 206 and the narrowed part 242 of the retaining pipe 208. That is, an end of the biasing member 210 on the distal side abuts against a proximal end surface of the protrusion 220, and an end of the biasing member 210 on the proximal side abuts against an end surface of the narrowed part 242 of the retaining pipe 208 on the distal side.

As the clip body 206 moves from the distal side to the proximal side, with respect to the retaining pipe 208, the biasing member 210 is gradually compressed. On the other hand, the biasing member 210 is extended in accordance with the movement of the clip body 206 from the proximal side to the distal side with respect to the retaining pipe 208, and the elastic force causes the clip body 206 to be biased from the proximal side to the distal side with respect to the retaining pipe 208 and the clip body 206 to be moved from the proximal side to the distal side with respect to the retaining pipe 208.

As illustrated in FIGS. 33 and 34, the treatment tool body 204 comprises an insertion part including a coupling member 212, an operating wire 244, a coiled sheath 246, and a tube sheath 248, and an operating part that is not illustrated.

Figure 38:
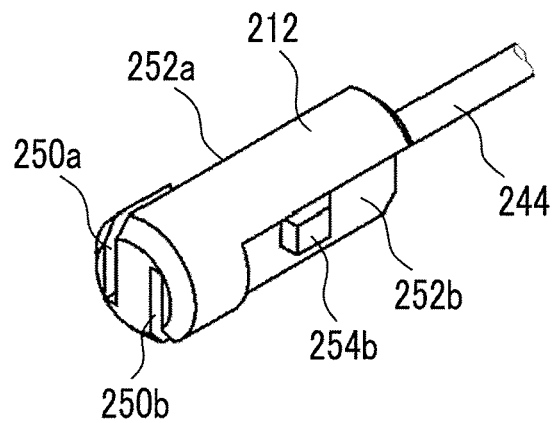
FIG. 38 is a perspective view of a coupling member and an operating wire of the clip treatment tool illustrated in FIG. 34.

As illustrated in FIG. 38, the coupling member 212 has a cylindrical distal end portion, and has an external diameter smaller than the internal diameter of the narrowed part 242 of the retaining pipe 208. The coupling member 212 is housed within the retaining pipe 208 until the coupling member is separated from the clip 202. The coupling member 212 has two recesses 250a and 250b provided in the cylindrical portion of the distal end, two notches 252a and 252b provided on a proximal end portion, and two protrusions 254a and 254b provided at the center of the two notches 252a and 252b, respectively.

The recess 250a is formed from the bottom to the top in the drawing, and a narrow portion closer to the proximal side than the stepped part 224a of the first arm 214a is inserted thereinto from the bottom and is movably engaged therewith. The stepped part 224a may abut against a distal end portion of the coupling member 212. On the other hand, the recess 250b is formed from the top to the bottom in the drawing, and a narrow portion closer to the proximal side than the stepped part 224b of the second arm 214b is inserted thereinto from the top and is movably engaged therewith. The stepped part 224b may abut against a distal end portion of the coupling member 212.

The notches 252a and 252b respectively have surfaces flush with surfaces on central axis sides of the recesses 250a and 250b.

The protrusions 254a and 254b are respectively fitted into the hole parts 226a and 226b provided in the arms 214a and 214b, and can be moved through the retaining pipe 208 to the distal side or the proximal side as an assembly in which the coupling member 212, and the arms 214a and 214b of the clip body 206 are integrated with each other.

In addition, it is preferable that side surfaces of the protrusions 254a and 254b on the proximal side have inclined surfaces that are inclined from the distal side to the proximal side. This is because, in a case where the coupling member 212 is strongly pulled to the proximal side as the protrusions 254a and 254b have the inclined surfaces, the protrusions 254a and 254b are likely to be disengaged from the hole parts 226a and 226b of the arms 214a and 214b, respectively.

As illustrated in FIG. 38, the operating wire 244 is fixed to an end of the coupling member 212 on the proximal side, and is formed of, for example, a single wire or a twisted wire made of metal. The operating wire 244 is inserted through the coiled sheath 246 and the tube sheath 248 so as to be movable in an axial direction of the coiled sheath 246 and the tube sheath 248.

The operating wire 244 moves to the distal side or the proximal side through the coiled sheath 246 and the tube sheath 248, and moves the integrated coupling member 212 and clip body 206 to the distal side or the proximal side inside the retaining pipe 208. That is, by pushing out the operating wire 244 from the proximal side to the distal side, thereby moving the integrated coupling member 212 and clip body 206 to the proximal side within the retaining pipe 208 and pulling the operating wire 244 from the distal side to the proximal side, the integrated coupling member 212 and clip body 206 can be moved to the distal side within the retaining pipe 208.

In addition, an end of the operating wire 244 on the proximal side is connected to the operating part that is not illustrated.

The coiled sheath 246 and the tube sheath 248 are both flexible and tubular. The coiled sheath 246 is inserted through the tube sheath 248. The internal diameter of the distal end of the coiled sheath 246 is formed so as to be slightly larger than the external diameter of the proximal end of the retaining pipe 208. The proximal end of the retaining pipe 208 is fitted to the distal end of the coiled sheath 246, and the retaining pipe 208 is attachably and detachably mounted on the coiled sheath 246. The coiled sheath 246 and the tube sheath 248 are formed of, for example, fluororesins, such as polytetrafluoroethylene (PTFE), or resin materials, such as high-density polyethylene (HDPE).

The clip treatment tool of the present embodiment is basically configured as described above.

Next, the operation of the clip treatment tool 200 will be described.

First, the operation in a case where a treatment part is ligated by the clip 202 will be described. In the following description, it is assumed that the insertion part of the endoscope that is not illustrated has already been inserted into the patient's body.

First, an operator's operation causes the insertion part of the clip treatment tool 200 to be inserted from the treatment tool insertion port of the endoscope that is not illustrated and causes the distal end of the insertion part of the clip treatment tool 200, more exactly, the distal end of the clip 202 to be protruded from the treatment tool delivery port of the endoscope.

Subsequently, the operating wire 244 is moved from the proximal side to the distal side by the operation of the operating part of the clip treatment tool 200 by the operator.

Figure 39:
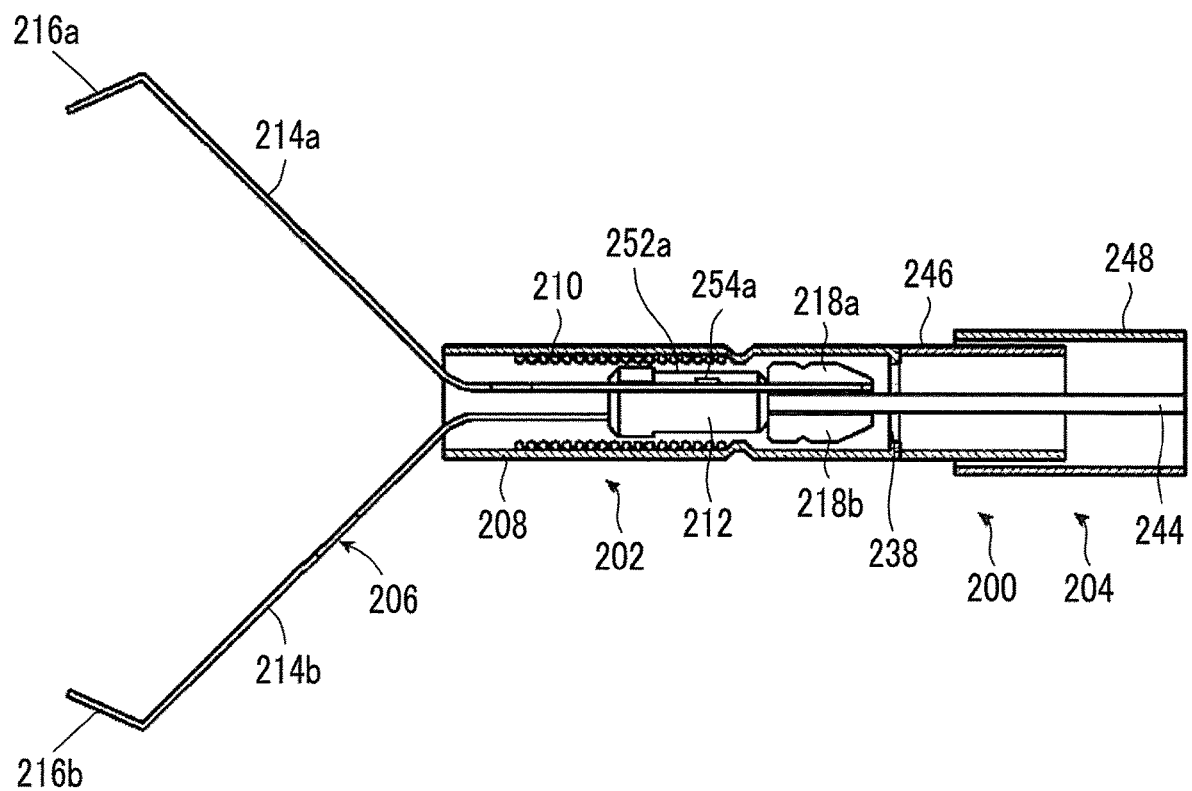
FIG. 39 is a cross-sectional view illustrating a side surface of an embodiment in which the clip body of the clip of the clip treatment tool illustrated in FIG. 33 is in an open state.
Figure 40:
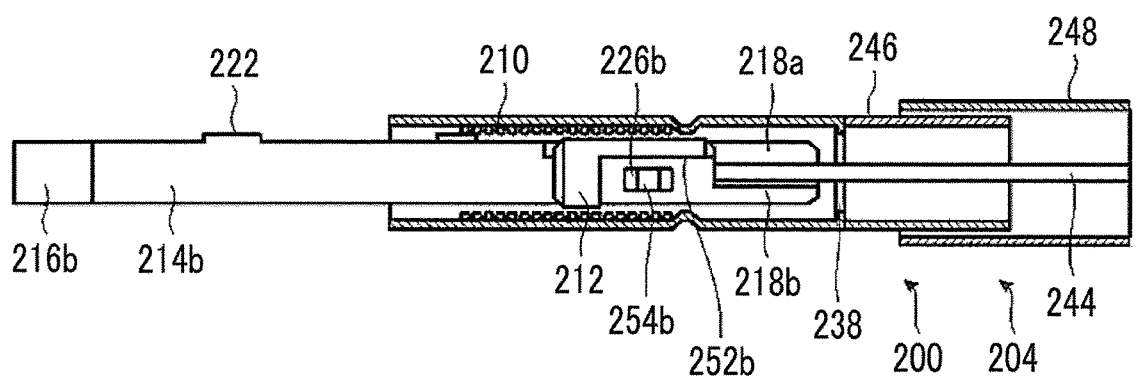
FIG. 40 is a cross-sectional view illustrating a plane of the clip illustrated in FIG. 39.

As the operating wire 244 moves from the proximal side to the distal side, the biasing member 210 is extended, and the coupling member 212 and the clip body 206 are biased by the biasing member 210 and move from the proximal side to the distal side. Accordingly, as illustrated in FIGS. 39 and 40, the two arms 214a and 214b of the clip body 206 is brought into the open state.

Subsequently, the insertion part is moved from the proximal side to the distal side by an operator's operation, and the distal ends of the two arms 214a and 214b in the open state are pressed against the treatment part.

Subsequently, the operating wire 244 is moved from the distal side to the proximal side by the operation of the operating part of the clip treatment tool 200 by the operator in a state where the distal ends of the two arms 214a and 214b in the open state are pressed against the treatment part.

As the operating wire 244 moves from the distal side to the proximal side, the biasing member 210 is compressed.

The coupling member 212 and the clip body 206 moves from the distal side to the proximal side against the biasing force of the biasing member 210, the two arms 214a and 214b are pressed and elastically deformed by the distal end of the retaining pipe 208 in the direction in which the arms approach each other, and the two arms 214a and 214b are gradually closed from the open state.

As the coupling member 212 and the clip body 206 move to the distal side or the proximal side in the state before the clip body 206 is locked to the retaining pipe 208, the two arms 214a and 214b is openable and closable.

Figure 41:
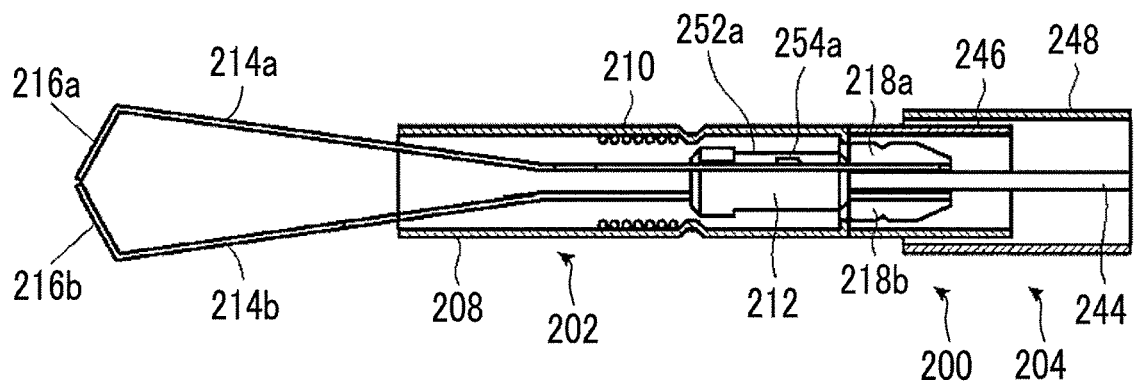
FIG. 41 is a cross-sectional view illustrating a side surface of an embodiment in which the clip body of the clip of the clip treatment tool illustrated in FIG. 33 is in a closed state.
Figure 42:
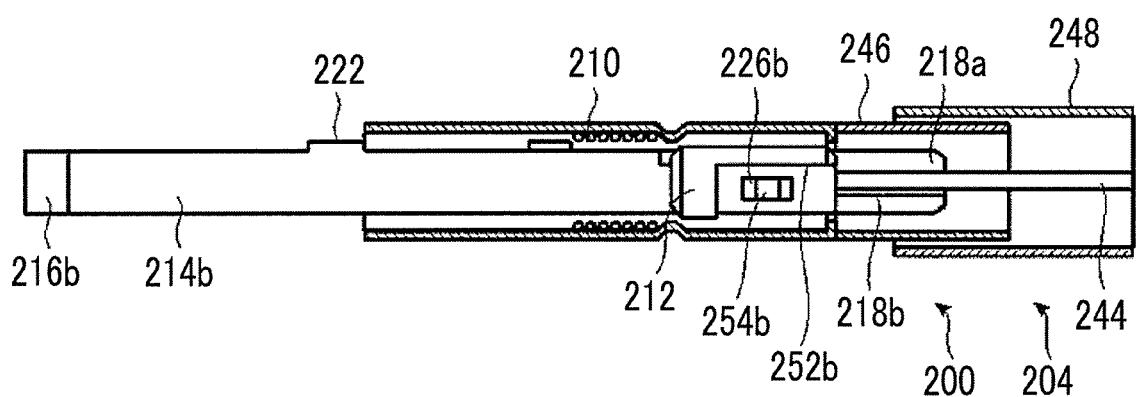
FIG. 42 is a cross-sectional view illustrating a plane of the clip illustrated in FIG. 41.

As the coupling member 212 and the clip body 206 move from the distal side to the proximal side, the biasing member 210 is compressed. The clip body 206 moves from the distal side to the proximal side together with the coupling member 212, and the two arms 214a and 214b are pressed and elastically deformed by the distal end of the retaining pipe 208 in the direction in which the arms approach each other, are gradually closed from the open state (full open state), and as illustrated in FIGS. 41 and 42, are finally brought into the closed state (fully closed state). Additionally, as the coupling member 212 and the clip body 206 move from the distal side to the proximal side, the locking parts 218a and 218b of the two arms 214a and 214b of the clip body 206 move from the distal side to the proximal side, and protrude from the proximal end surface of the retaining pipe 208 through the locking hole 240 of the retaining pipe 208.

On the other hand, as the coupling member 212 moves from the proximal side to the distal side, the biasing member 210 is extended, and the coupling member 212 is biased by the biasing member 210, and further moves from the proximal side to the distal side. The clip body 206 moves from the proximal side to the distal side, and the two arms 214a and 214b are gradually opened from the closed state by the elastic force and are finally brought into the open state. Additionally, as the coupling member 212 moves from the proximal side to the distal side, the locking parts 218a and 218b of the clip body 206 move from the proximal side to the distal side, and are housed within the retaining pipe 208 through the locking hole 240 of the retaining pipe 208.

In this way, in the state before the clip body 206 is locked to the retaining pipe 208, the two arms 214a and 214b can be opened and closed and a treatment part can be re-grabbed by the claws 216a and 216b of the two arms 214a and 214b. Thus, an intended treatment part can be accurately grabbed.

Subsequently, the operating wire 244 is further moved from the distal side to the proximal side in a state where the treatment part is grabbed by the claw 216a and the claw 216b of the two arms 214a and 214b.

According to this, the biasing member 210 is further compressed, the coupling member 212 and the clip body 206 further moves from the distal side to the proximal side against the biasing force of the biasing member 210, and the two arms 214a and 214b are further closed.

As the coupling member 212 and the clip body 206 further moves from the distal side to the proximal side, the locking parts 218a and 218b of the clip body 206 further move from the distal side to the proximal side, and the locking parts 218a and 218b protrude from the proximal end surface of the retaining pipe 208 through the locking hole 240 of the retaining pipe 208.

As the locking parts 218a and 218b further moves from the distal side to the proximal side, the inclined parts 230a and 230b of the locking parts 218a and 218b of the arms 214a and 214b of the clip body 206 are pressed by the distal end of the locking hole 240 in the direction in which the inclined parts approach each other, and the plate-shaped members 228a and 228b including the locking parts 218a and 218b bend in a direction in which the members approach each other. Accordingly, the spacing between the two inclined parts 230a and 230b and further the two more top parts 234a and 234b is reduced, and the locking parts 218a and 218b pass through the locking hole 240 of the retaining pipe 208.

In a case where the locking parts 218a and 218b of the clip body 206 move to the distal side or the proximal side, the inclined surfaces (outer surfaces) of the two inclined parts 230a and 230b and the inner peripheral surface of the distal end of the locking hole 240 of the retaining pipe 208 come into contact with each other, and the inclined surfaces of the two inclined parts 230a and 230b slide along the inner peripheral surface of the distal end of the locking hole 240. Since the inclined surfaces of the two inclined parts 230a and 230b have the two inclined parts 230a and 230b in a case where the locking parts 218a and 218b slide along the inner peripheral surface of the distal end of the locking hole 240, the inclined surfaces function to facilitate movement of the locking parts 218a and 218b to the distal side or the proximal side with respect to the locking hole 240.

As the locking parts 218a and 218b of the clip body 206 further moves from the distal side to the proximal side, the corners 232a and 232b of the two top parts 234a and 234b on the distal side move to a position exceeding the locking hole 240, and the two top parts 234a and 234b with reduced spacing are spaced apart from each other by the elastic force of the plate-shaped members 228a and 228b. Accordingly, the spacing in the corners 232a and 232b of the two top parts 234a and 234b on the distal side becomes larger than the internal diameter of the locking hole 240, and the corners 232a and 232b of the two top parts 234a and 234b on the distal side are locked to a proximal end surface of the locked part 238 of the retaining pipe 208. That is, the locking parts 218a and 218b are locked to the locked part 238.

Additionally, in a case where the corners 232a and 232b of the two top parts 234a and 234b on the distal side move to the position exceeding the locking hole 240, the two arms 214a and 214b are brought into the closed state, as illustrated in FIGS. 41 and 42.

Accordingly, in the retaining pipe 208 integrated with the coupling member 212, the two arms 214a and 214b is locked to the clip body 206 in the closed state, and the treatment part is ligated by the claw 216a and the claw 216b of the two arms 214a and 214b.

Subsequently, the operating wire 244 is further moved from the distal side to the proximal side in a state where the coupling member 212 and the clip body 206 are locked to the retaining pipe 208, that is, in a state where the treatment part is ligated, by the claw 216a and the claw 216b of the two arms 214a and 214b.

According to this, the coupling member 212 and the clip body 206 further move from the distal side to the proximal side, and an end of the protrusion 222 of the second arm 214b on the proximal side abuts against the distal end of the retaining pipe 208. Accordingly, the movement of the coupling member 212 and the clip body 206 from the distal side to the proximal side is restricted.

Subsequently, the operating wire 244 is further pulled and moved from the distal side to the proximal side, in a state where the coupling member 212 and the clip body 206 are locked to the retaining pipe 208 and the movement of the coupling member 212 and the clip body 206 from the distal side to the proximal side is restricted.

As the operating wire 244 is pulled and moved from the distal side to the proximal side, the two arms 214a and 214b of the clip body 206 ride on the protrusions 254a and 254b of the coupling member 212 fitted to the hole parts 226a and 226b, and the central parts of the two arms 214a and 214b are pushed apart and spaced apart from each other. As a result, the protrusions 254a and 254b of the coupling member 212 are disengaged from the hole parts 226a and 226b of the two arms 214a, 214b, and the recesses 250a and 250b of the coupling member 212 slide along the proximal sides of the two arms 214a and 214b and are disengaged from the ends of the two arms 214a and 214b on the proximal side. Accordingly, the coupling member 212 and the operating wire 244 are separated from the two arms 214a and 214b of the clip body 206.

Subsequently, the operating wire 244 is moved from the proximal side to the distal side in a state where the coupling member 212 and the operating wire 244 are separated from the clip body 206.

As the operating wire 244 moves from the proximal side to the distal side, the coupling member 212 also moves from the proximal side to the distal side, and the distal end of the coupling member 212 abuts against the proximal ends of the locking parts 218a and 218b of the clip body 206.

Figure 43:
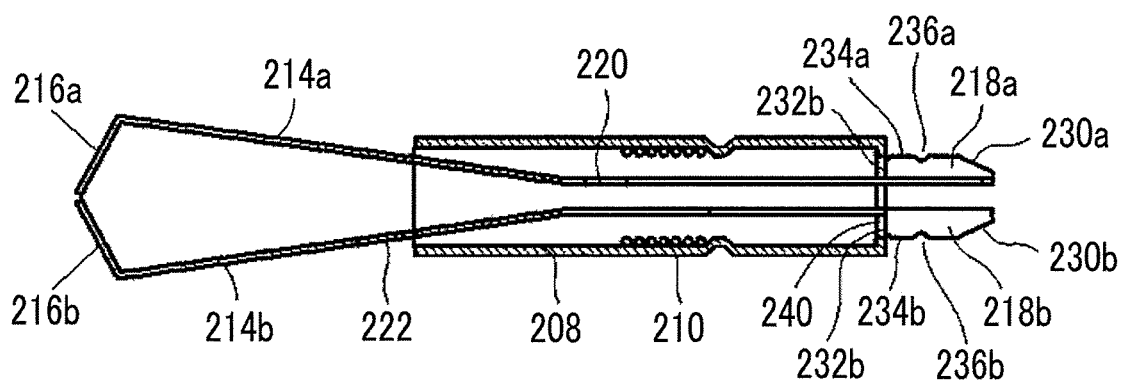
FIG. 43 is a cross-sectional view illustrating a side surface of the clip in a state where the clip is separated from the clip treatment tool illustrated in FIG. 41.
Figure 44:
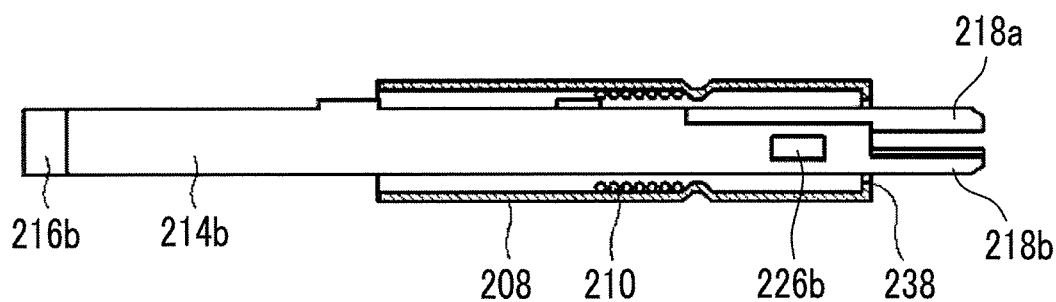
FIG. 44 is a cross-sectional view illustrating a plane of the clip illustrated in FIG. 43.

As the operating wire 244 further moves from the proximal side to the distal side, the locking parts 218a and 218b of the clip body 206, that is, the clip body 206 is pushed out to the distal side by the coupling member 212, and the retaining pipe 208 of the clip 202 is separated from the coiled sheath 246. Accordingly, as illustrated in FIGS. 43 and 44, the clip 202 is separated in the closed state. That is, the clip 202 is indwelled in the treatment part in a state where the treatment part is ligated by the clip 202.

Thereafter, the insertion part of the endoscope is pulled out and taken out from the inside of the patient's body by an operator's operation in a state where the insertion part of the clip treatment tool 200 is inserted into the endoscope. In addition, the above-mentioned operation is repeatedly performed in a case where a plurality of treatment parts are ligated.

Next, the operation in a case where the clip 202 is removed from the treatment part will be described.

First, the operation in a case where the clip 202 is removed using the second treatment tool by the operation of the operating part by then operator will be described.

In a case where the clip 202 is removed from the treatment part, the two facing top parts 234a and 234b of the locking parts 218a and 218b of the two arms 214a and 214b of the clip body 206 are sandwiched and pressed from both outsides in a direction of an arrow illustrated in FIG. 43 by the operation of the second treatment tool by the operator in a state where the clip 202 is indwelled in the treatment part.

Figure 45:
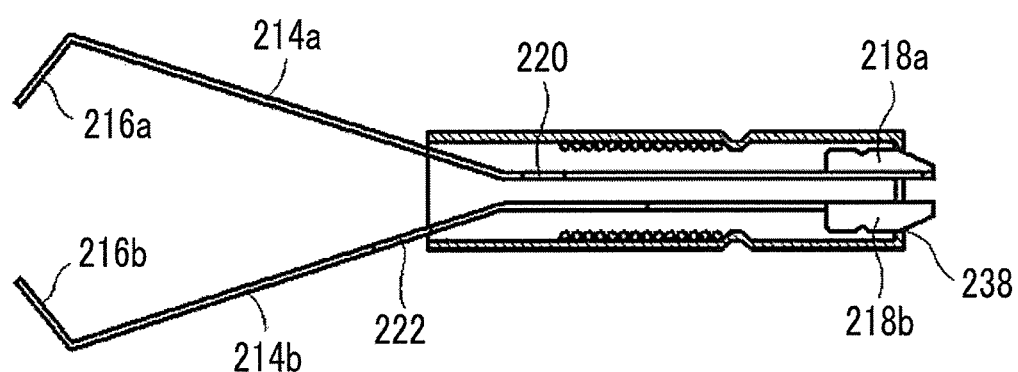
FIG. 45 is a cross-sectional view illustrating a side surface in a state where the clip body of the clip illustrated in FIG. 43 is unlocked.
Figure 46:
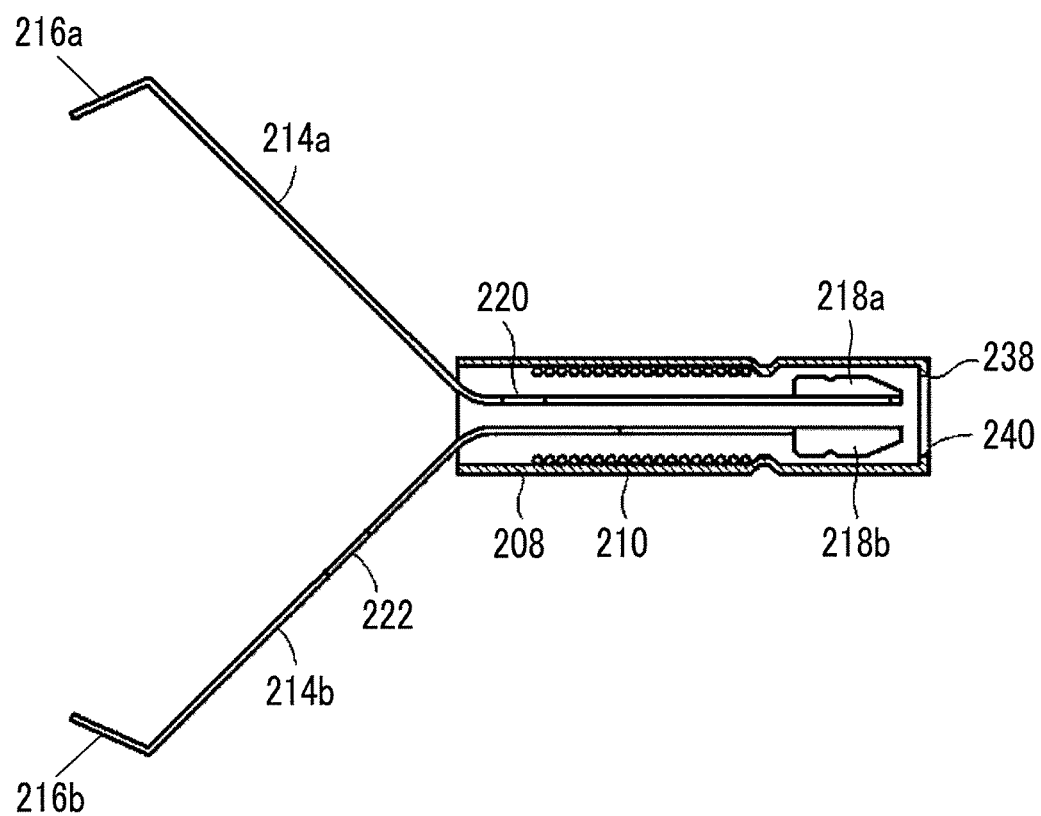
FIG. 46 is a cross-sectional view illustrating a side surface in the open state of the clip body of the clip illustrated in FIG. 45.

In a case where the two top parts 234a and 234b are pressed from both outsides and approach each other, the spacing in the corners 232a and 232b of the two top parts 234a and 234b on the distal side becomes smaller than the internal diameter of the locking hole 240 of the retaining pipe 208, and the locking between the clip body 206 and the retaining pipe 208 is released. In a case where the locking is released, as illustrated in FIG. 45, the clip body 206 moves from the proximal side to the distal side through the retaining pipe 208, and the two arms 214a and 214b are gradually opened from the closed state by the elastic force, and finally return to the open state as illustrated in FIG. 46. Accordingly, the clip 202 is removed from the treatment part.

Thereafter, the insertion part of the endoscope is pulled out and taken out from the inside of the patient's body in a state where the second treatment tool is inserted into the endoscope by an operator's operation. For example, in a state where any spot of the clip 202 is sandwiched by the second treatment tool, the insertion part of the endoscope is pulled out from the inside of the patient's body, and the clip 202 removed from the treatment part is also simultaneously taken out by the outside of the patient's body. In addition, the above-mentioned operation is repeatedly performed in a case where a plurality of the clips 202 are removed from the treatment part.

In the clip treatment tool 200, the treatment part can be re-grabbed by the two arms 214a and 214b until the treatment part is ligated by the clip 202. Additionally, since the clip body 206 and the retaining pipe 208 are locked after the treatment part is ligated by the clip 202, a state where the treatment part is ligated by the clip 202 can be reliably maintained. Additionally, after the clip 202 is indwelled in the treatment part, the locking between the clip body 206 and the retaining pipe 208 can be released at any timing, and the clip 202 can be removed from the treatment part.

Additionally, specific configurations of the first treatment tool 1 and the second treatment tool as the clip treatment tool are not limited to those of the above embodiments, and separate configurations that exhibit the same function may be used. For example, the clip 10 may include two or more arms, such as including three arms.

Although the invention has been described above in detail, the invention is not limited to the above embodiments, and various improvements and modifications may be made without departing from the scope of the invention.

EXPLANATION OF REFERENCES

1: first treatment tool
2, 3: second treatment tool
10, 10a, 10b, 10c, 10e, 202: clip (clip unit)
11, 206: clip body
12, 214a: first arm
12a, 13a, 216a, 216b: claw
13, 214b: second arm
14: central part
16, 17: first locked part
16a, 17a, 32b: proximal end surface
16b, 17b, 32c: distal end surface
18, 18a, 19, 19a, 23, 24: protrusion
21, 22: second locked part
31, 208: retaining pipe
32, 218a, 218b: locking part
32a: edge part (opening part)
34: pin-shaped member
35: cantilever beam member
36: helical spring (spring member)
36a: bare wire
36b: seat winding part
37: protrusion
38a, 38b: slit
39a, 39b: pressed part
40, 204: treatment tool body
41, 43a, 43b, 220, 222, 254a, 254b: protrusion
42a, 42b: opening part
50: overtube
60, 81, 91, 124: insertion part
61: sheath part
62, 85, 95, 244: operating wire
63, 212: coupling member
66, 246: coiled sheath
67: distal end member (stopper part)
67a: recess
67b: distal end support surface (distal end surface)

68: stepped part
69: supporting member
72: diameter-enlarged part
73, 90: loop part
73a: wire
76: coupling part body
76a: through-hole
76b: inclined surface
77: hook part
80: distal end gripping part
82, 92, 100, 126: operating part
83a, 83b: claw member
84, 94: sheath
86, 96, 101: operating part body
87, 97, 102: slider
110: endoscope system
112: light source device
114: endoscope
116: processor device
118: monitor (display device)
120: console (input device)
122: universal cord
128: bending part
130: distal end
132: button
134: angle knob
136: treatment tool insertion port
138a, 138b: illumination window
140: observation window
142: air/water supply port
144: treatment tool delivery port
200: clip treatment tool
210: biasing member
224a, 224b: stepped part
226a, 226b: hole part
228a, 228b: plate-shaped member
230a, 230b: inclined part
232a, 232b: corner
234a, 234b: top part
236a, 236b, 250a, 250b: recess
238: locked part
240: locking hole
242: narrowed part
248: tube sheath
252a, 252b: notch

What is claimed is:

1. A clip treatment tool comprising:
an operating part;
a clip;
a sheath part; and
a clip removal part,
wherein the clip is attachably and detachably disposed at a distal end of the sheath part and the operating part is attached to a proximal end of the sheath part,
wherein the clip includes
a clip body having two or more arms that are opened and closed,
a clip locking part that locks the two or more arms to a closed state after the two or more arms of the clip body are brought into an open state by an operation of the operating part, the two or more arms are brought into the closed state in a state where distal ends of the two or more arms brought into the open state are pressed against a treatment part, and the treatment part is ligated by the distal ends of the two or more arms brought into the closed state,
a tubular retaining pipe that houses a proximal end of the clip body,
a spring member that biases the clip body housed within the retaining pipe to a distal side of the retaining pipe, and
a movement regulating part that restricts the clip body from jumping out of a distal end of the retaining pipe in a case where the clip removal part releases the locking and the spring member is extended to relatively move the clip body to the distal side of the retaining pipe,
wherein the clip removal part releases the locking to the closed state of the two or more arms of the clip indwelled in the treatment part after the clip of which the two or more arms are locked to the closed state by the clip locking part are separated from the sheath part and indwelled in the treatment part by the operation of the operating part, to bring the two or more arms into the open state as the locking is released, and holds and removes the clip removed from the treatment part,
wherein the two or more arms are protruded from the distal end of the retaining pipe to be in the open state and the two or more arms protruded from the distal end of the retaining pipe are housed within the retaining pipe to be in the closed state by the operation of the operating part,
wherein the clip locking part has protruding parts provided in the two or more arms, and an opening part provided in a proximal end of the retaining pipe,
wherein, in a case where the clip body is relatively moved to a proximal side of the retaining pipe, and an external diameter of the protruding parts that is a diameter of a circumscribed circle circumscribed on distal ends of the protruding parts of the two or more arms becomes smaller than an internal diameter of the opening part that is a diameter of an inscribed circle inscribed on an opening of the opening part, so that the protruding parts exceeds the opening part, the external diameter of the protruding parts becomes larger than the internal diameter of the opening part, and the protruding parts and the opening part are engaged with each other, so that the two or more arms are locked to the closed state,
wherein the spring member is compressed as the clip body is relatively moved to the proximal side of the retaining pipe, and the two or more arms are locked to the closed state in a state where the clip body is biased to the distal side of the retaining pipe by the spring member,
wherein the spring member is extended to relatively move the clip body to the distal side of the retaining pipe in a case where the locking is released, and the two or more arms are protruded from the distal end of the retaining pipe to be in the open state,
wherein the clip removal part reduces the external diameter of the protruding parts to be equal to or less than the internal diameter of the opening part, releases the locking by releasing the engagement between the protruding parts and the opening part, and the spring member is extended to relatively move the clip body to the distal side of the retaining pipe in a case where the locking is released, and the two or more arms are protruded from the distal end of the retaining pipe to be in the open state.

2. The clip treatment tool according to claim 1,
wherein the clip removal part has a snare-like member including a loop that is enlarged or reduced in diameter by the operation of the operating part, and reduces the external diameter of the protruding parts to be equal to or less than the internal diameter of the opening part by surrounding and clamping the protruding parts by the loop.

3. The clip treatment tool according to claim 1,
wherein the clip removal part has gripping forceps including a gripping part that is opened and closed by the operation of the operating part, and reduces the external diameter of the protruding parts to be equal to or less than the internal diameter of the opening part by sandwiching and pressing the protruding parts by the gripping part.

4. The clip treatment tool according to claim 1,
wherein the clip body has a connecting part that connects proximal ends of the two or more arms to each other,
wherein the movement regulating part has a pin-shaped member, and the pin-shaped member has both ends fixed to an inner peripheral surface of the retaining pipe and is inserted between the two or more aims, to extend in a direction orthogonal to an opening/closing direction of the two or more arms, and
wherein, in a case where the locking is released and the clip body has relatively moved to the distal side of the retaining pipe, the pin-shaped member and the connecting part abut against each other to restrict the clip body from jumping out of the distal end of the retaining pipe.

5. The clip treatment tool according to claim 1,
wherein the clip body has a connecting part that connects proximal ends of the two or more arms to each other,
wherein the movement regulating part has one or more cantilever beam members, and the one or more cantilever beam members have one end fixed to the distal end of the retaining pipe, and is inserted between the two or more arms, to extend in a direction orthogonal to an opening/closing direction of the two or more arms from the distal end of the retaining pipe, and
wherein, in a case where the locking is released and the clip body has relatively moved to the distal side of the retaining pipe, the cantilever beam member and the connecting part abut against each other to restrict the clip body from jumping out of the distal end of the retaining pipe.

6. The clip treatment tool according to claim 1,
wherein the clip body has a connecting part that connects proximal ends of the two or more arms to each other,
wherein the movement regulating part has a pin-shaped member, and the pin-shaped member has both ends fixed to the distal end of the retaining pipe, and is inserted between the two or more aims, to extend in a direction orthogonal to an opening/closing direction of the two or more arms, and
wherein, in a case where the locking is released and the clip body has relatively moved to the distal side of the retaining pipe, the pin-shaped member and the connecting part abut against each other to restrict the clip body from jumping out of the distal end of the retaining pipe.

7. The clip treatment tool according to claim 1,
wherein the clip body has a connecting part that connects proximal ends of the two or more arms to each other,
wherein the movement regulating part has two or more protrusions that are provided on an inner peripheral surface of the retaining pipe, are inserted between the two or more arms, and protrude in a direction orthogonal to an opening/closing direction of the two or more arms from the inner peripheral surface of the retaining pipe, and
wherein, in a case where the locking is released and the clip body has been relatively moved to the distal side of the retaining pipe, the two or more protrusions and the connecting part abut against each other to restrict the clip body from jumping out of the distal end of the retaining pipe.

8. The clip treatment tool according to claim 1,
wherein the movement regulating part has a second protrusion that protrudes from each of the two or more aims toward a wall face of the retaining pipe and two or more slits that are formed in the wall face of the retaining pipe in correspondence with the second protrusion of each of the two or more arms and are engaged with the second protrusion of each of the two or more arms, and
wherein, in a case where the locking is released and the clip body has relatively moved to the distal side of the retaining pipe, the second protrusion of each of the two or more arms abuts against a distal end of each of the two or more slits of the retaining pipe to restrict the clip body from jumping out of the distal end of the retaining pipe.

9. The clip treatment tool according to claim 1, further comprising:
pressed parts that are provided on both sides of the protruding parts in a pressing direction in which the protruding parts are pressed, in an outer end surface of the proximal end of the retaining pipe, and are moved toward the protruding parts by being pressed from the both sides in the pressing direction,
wherein the clip removal part moves the pressed parts toward the protruding parts by pressing the pressed parts from the both sides in the pressing direction, reduces the external diameter of the protruding parts to be equal to or less than the internal diameter of the opening part by pressing the protruding parts, and releases the locking by releasing the engagement between the protruding parts and the opening part.

10. The clip treatment tool according to claim 1,
wherein the retaining pipe has two or more second opening parts that respectively expose portions of the two or more arms in a case where the arm is locked to the closed state, at proximal-side positions of side surfaces that respectively face the two or more arms, and
wherein the clip removal part presses the two or more arms exposed from the two or more second opening parts of the side surfaces of the retaining pipe to reduce the external diameter of the protruding parts to be equal to or less than the internal diameter of the opening part, and releases the locking by releasing the engagement between the protruding parts and the opening part.

11. The clip treatment tool according to claim 10,
wherein each of the two or more arms has a third protrusion that protrudes from a central axis of the retaining pipe toward each of the two or more second opening parts in a case where the two or more arms are locked to the closed state.

12. The clip treatment tool according to claim 1, further comprising:

an operating wire that is inserted so as to be movable forward and backward within the sheath part by the operation of the operating part; and a coupling member that couples the clip body and the operating wire to each other, wherein the clip further includes a biasing member, wherein the clip body has two arms, and the two arms face each other, and extend so as to be separated from each other from the proximal side toward the distal side, wherein as the clip body moves to the distal side or the proximal side, the retaining pipe functions to open and close the two arms, and houses the clip body therein by the movement of the clip body from the distal side to the proximal side, wherein the clip locking part has a locking part provided on proximal sides of the two arms, and a locked part provided on the proximal side of the retaining pipe, wherein the coupling member is housed inside the retaining pipe, and is attachably and detachably engaged with the two arms, and couples the clip body and the operating wire to each other by connecting a distal end of the operating wire to a proximal end thereof, wherein the biasing member is housed inside the retaining pipe, and biases the clip body from the proximal side to the distal side with respect to the retaining pipe, and wherein as the operating wire moves from the distal side to the proximal side by the operation of the operating part, the coupling member moves from the distal side to the proximal side, the clip body moves from the distal side to the proximal side, the locking part is locked to the locked part, and the clip body is locked to the retaining pipe.

13. The clip treatment tool according to claim 12, wherein each of the two arms has a projection part that protrudes in a width direction, wherein the retaining pipe has a narrowed part having an internal diameter narrower than an internal diameter at both ends, at a central part thereof in an axial direction, and wherein the biasing member is disposed between the projection part and the narrowed part, and the locking part is movable nearer to the proximal side than the narrowed part.

14. The clip treatment tool according to claim 12, wherein as the coupling member moves from the distal side to the proximal side, the two arms are pressed by the distal end of the retaining pipe in a direction in which the two arms approach each other, and the two arms are gradually closed from the open state and brought into the closed state.

15. The clip treatment tool according to claim 14 wherein the locking part includes two plate-shaped members which are provided at each end on the proximal side of the two arms, wherein the two plate-shaped members have, in order along a direction from the proximal side to the distal side, two inclined parts whose width gradually widen in the direction from the proximal end toward the distal end, two top parts formed so as to face each other in an opening/closing direction of the two arms, and two corner parts, wherein the locked part has a locking part that is formed as an end of the retaining pipe on the proximal side is reduced in diameter and has an internal diameter smaller than a length between the two top parts that face each other, and wherein as the coupling member moves from the distal side to the proximal side, the two inclined parts are pressed by a distal end of the locking hole in a direction in which the inclined parts approach each other and pass through the locking hole, the corners of the two top parts move to positions exceeding the locking hole of the locked part, the corners of the two top parts are locked to a proximal end surface of the locked part by separating the two inclined parts from each other by an elastic force, and the coupling member is locked to the retaining pipe in a state where the two arms are in the closed state.

16. The clip treatment tool according to claim 15, wherein an external diameter of the coupling member is smaller than an internal diameter of the locking hole, and wherein as the operating wire moves from the distal side to the proximal side in a state where the coupling member is locked to the retaining pipe, the engagement between the two arms and the coupling member is released, the coupling member passes through the locking hole, a distal end of the coupling member moves to a position exceeding a proximal end of the locking part, and the clip body and the coupling member are separated from each other.

17. The clip treatment tool according to claim 16, wherein in a case where the two top parts are pressed from both outsides and an external diameter in the corners of the two top parts on the distal side becomes smaller than the internal diameter of the locking hole in a state where the clip body and the coupling member are separated from each other, the clip body is biased by the biasing member, to be moved from the proximal side to the distal side, and the two arms are gradually opened from the closed state and returns to the open state as the clip body moves from the proximal side to the distal side.

18. The clip treatment tool according to claim 15, wherein each of the two plate-shaped members is formed such that a portion, in a width direction, of a proximal end of each of the two arms is bent in the direction orthogonal to the opening/closing direction of the two arms, wherein each of the two top parts has a recess that is recessed in the opening/closing direction of the two arms, and wherein the recess of each of the two top parts is pressed from both outsides in the opening/closing direction of the two arms.

19. The clip treatment tool according to claim 1, comprising:

a first treatment tool that has at least a first operating part serving as the operating part, and the sheath part; and a second treatment tool that has at least a second operating part serving as the operating part, and the clip removal part, wherein the first treatment tool and the second treatment tool are separately configured.

* * * * *